US008021841B1

(12) United States Patent
Schatz

(10) Patent No.: US 8,021,841 B1
(45) Date of Patent: Sep. 20, 2011

(54) METHODS AND APPARATUSES FOR SPATIALLY SEPARATING MOLECULES ATTACHED TO A SUPPORT AND USES IN BIOTECHNOLOGY

(76) Inventor: Kenneth David Schatz, Los Altos, CA (US)

(*) Notice: Subject to any disclaimer, the term of this patent is extended or adjusted under 35 U.S.C. 154(b) by 64 days.

(21) Appl. No.: 12/313,763

(22) Filed: Nov. 24, 2008

Related U.S. Application Data

(63) Continuation-in-part of application No. 11/827,588, filed on Jul. 11, 2007, now Pat. No. 7,745,129.

(60) Provisional application No. 61/004,137, filed on Nov. 23, 2007.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .......... 435/6; 536/22.1; 536/23.1; 536/24.3

(58) Field of Classification Search ..... 435/6; 536/22.1, 536/23.1, 24.3
See application file for complete search history.

(56) References Cited

U.S. PATENT DOCUMENTS

| 5,714,330 | A | 2/1998 | Brenner | |
|---|---|---|---|---|
| 6,322,968 | B1 | 11/2001 | Head | |
| 7,745,129 | B1* | 6/2010 | Schatz | 435/6 |
| 2010/0261615 | A9* | 10/2010 | Park et al. | 506/9 |
| 2010/0268478 | A1* | 10/2010 | Andregg et al. | 702/20 |

OTHER PUBLICATIONS

Aston et al., Optical Mapping : An approach for fine mapping. Methods in Enzymology 303 :55-end (1999).*
Braslaysky et al., Sequence information can be obtained from single DNA molecules. PNAS 100(7) : 3960-3964 (2003).*
Bockelmann et al., Molecular Stick-Slip Motion Revealed by Opening DNA with Piconewton Forces. Physical Review Letters 79(22) : 4489-4492 (1997).*
Chan et al., DNA Mapping Using Microfluidic Stretching and Single-Molecule Detection of Fluorescent Site-Specific Tags. Genome Research 14 : 1137-1146 (2004).*
Chan et al., A simple DNA stretching method for fluorescence imaging of single DNA molecules. Nucleic acids Research 34 (17) e113 6 pages (Sep. 2006).*
Ferree et al., Electrokinetic Stretching of tethered DNA. Biophysical Journal 85 : 2539-2546 (2003).*
Baumann et al., Stretching of single collapsed DNA molecules. Biophysical Journal 78 : 1965-1978 (2000).*
Demers et al. Direct Patterning of modified oligonucleotide on metals and insulators by Dip-pen nanolithography. Science 296 : 1836—end (2002).*
Gueroui et al. Observation by fluorescence microscopy of transcription on single combed DNA. PNAS 99(9) 6065-6010 (2002).*
Klein et al.,Ordered stretching of single molecules of deoxyribose nucleic acid between microfabricated polystyrene lines. Applied Physics Letters 78(16) :2396-end (2001).*
Nakao et al., Useful technique for DNA-stretching and fixation. Nucleic Acids Research Supplement 2 :289-290 (2002).*
Strick et al., Review : Twisting and stretching single DNA molecules. Progress in Biophysics & Molecular Biology 74 : 115-140 (2000).*
Xiao et al. Rapid DNA mapping by fluorescent single molecule detection. Nucleic Acids Research 35(3) e16 (2007).*
Zimmermann et al., DNA stretching on functionalized gold surfaces. Nucleic Acids Research 22 (3): 492-497 (1994).*
Goss, WFM The Railway Age 41 : 1195-1198 (1906).*
Wang et al , Stretching DNA with optical Tweezers. Biophysical Journal 72 : 1335-1346 (1997).*
Washizu M., DNA manipulation in electrostatic fields 7th Internal conference on Miniaturized chemical and biochemical analysis systems (Oct. 2003).*
Wenner et al., Salt Dependence of the Elasticity and Overstretching Transition of Single DNA Molecules Biophysical Journal 82 : 3160-3169 (2002).*
Williams et al., The effect of pH on the ovestretching transition on dsDNA: Evidence of force-induced DNA melting, Biophysical Journal 80 : 874-881 (2001).*
Rouzina et al.. Force-induced melting of the DNA double helix. 1 Thermodynamic Analysis. Biophysical Journal 80 :882-893 (2001).*
Rouzina et al., Force-induced melting of the DNA double helix. 2. Effect of solution conditions Biophysical Journal 96 : 1248-1255 (2008).*
Shokri et al., DNA Overstretching in the Presence of Glyoxal: Structural Evidence of Force-Induced DNA Melting Biophysical Journal 96 : 1248-1255 (2008).*
Smith et al., Overstretching B-DNA: The Elastic Response of. Individual Double-Stranded and Single-Stranded. DNA Molecules Science 271 : 795-799 (1996).*
Noy et al., Strectching and breaking duplex DNA by chemical force microscopy. Chemistry & Biology 4 : 519-527 (1997).*
Parra et al., High resolution visual mapping of stretched DNA by flourescent hybridization. Nature Genetics 5 : 17-21 (1993).*
Perkins et al., Stretching of a sungle tethered polymer in a uniform flow. Science 268 : 83-87 (1995).*
Phillips et al., Application of single molecule technology to rapidly map long DNA and study the conformation of stretched DNA Nucleic Acids Research 33 (18) : 5829-5837 (2005).*
Chan et al., A simple DNA stretching method for flourescence imaging of single DNA molecules. Nucleic acids Research 34 (17) e113 6 pages (Sep. 2006).*
Heng et al., Stretching DNA using the Electric Field in a Synthetic Nanopore Nano Letters 5(10) : 1883-1888 (2005).*

(Continued)

*Primary Examiner* — Ethan C Whisenant

(57) ABSTRACT

Methods and apparatuses for analyzing biomolecules are presented. The methods include dividing of sample molecules into multiple fragments, spatially separating these fragments while maintaining knowledge of their original ordering, and analyzing individual fragments. Apparatuses and methods detailed provide for the spatial separation of sample fragments while maintaining their original ordering. In one embodiment, a sample molecule (2902) is attached to a top surface (2804) of a layer (2802). Layer (2802) is extended such that sample molecule (2902) is divided into fragments (3002), and fragments (3002) are spatially separated. Other embodiments are described and shown.

28 Claims, 22 Drawing Sheets

OTHER PUBLICATIONS

Leuba et al., Assembly of single chromatin fibers depends on the tension in the DNA molecule. Magnetic tweezers study. PNAS 100(2) : 495-500 (2003).*

Marko et al. Stretching DNA.Macromolecules 28 : 8759-8770 (1995).*

Sanger, F., Nicklen, S., Coulson, A.R., DNA sequencing with chain-terminating inhibitors, Proc. Natl. Acad. Sci. USA, Dec. 1977, pp. 5463-5467, vol. 74, No. 12.

Hyman, E.D., A new method of sequencing DNA, Analytical Biochemistry, Nov. 1, 1988, pp. 423-436, vol. 174, No. 2, Academic Press Inc., San Diego.

Ronaghi, M., Uhlen, M., Nyren, P., A sequencing method based on real-time pyrophosphate, Science, Jul. 17, 1998, pp. 363-365, vol. 281, AAAS, Washington DC.

Strezoska, Z., et al., DNA sequencing by hybridization: 100 bases read by a non-gel-based method, Proc. Natl. Acad. Sci. USA, Nov. 1991, pp. 10089-10093, vol. 88.

Chee, M., et al., Accessing genetic information with high-density DNA arrays, Science, Oct. 25, 1996, pp. 610-614, vol. 274; AAAS, Washington DC.

Hansma, H.G., et al., Reproducible imaaging and dissection of plasmid DNA under liquid with the atomic force microscope, Science, May 22, 1992, pp. 1180-1184, vol. 256.

Fried, M.G., et al., Role of hydration in the binding of lac repressor to DNA, Journal of Biological Chemistry, Dec. 27, 2002, pp. 50676-50682, vol. 277, No. 52.

Parra, I., Windle, B., High resolution visual mapping of stretched DNA by fluorescent hybridization, Nature Genetics, Sep. 1993, pp. 17-21, vol. 5, No. 1.

Weier, H-U.G., et al., Quantitative DNA fiber mapping, Human Molecular Genetics, 1995, pp. 1903-1910, vol. 4, No. 10, Oxford University Press, Oxford, England.

Chu, B.C.F., Wahl, G.M., Orgel, L.E., Derivatization of unprotected polynucleotides, Nucleic Acids Research, 1983, pp. 6513-6529, vol. 11, No. 18, IRL Press Ltd, Oxford, England.

Inman, R.B., Schnos, M., Partial Denaturation of Thymine- and 5-Bromouracil-containing DNA in alkali, Journal of Molecular Biology, 1970, pp. 93-98, vol. 49, Elsevier Ltd, UK.

Bensimon, A., et al., Alignment and sensitive detection of DNA by a moving interface, Science, Sep. 30, 1994, pp. 2096-2098, vol. 265, AAAS, Washington DC.

* cited by examiner

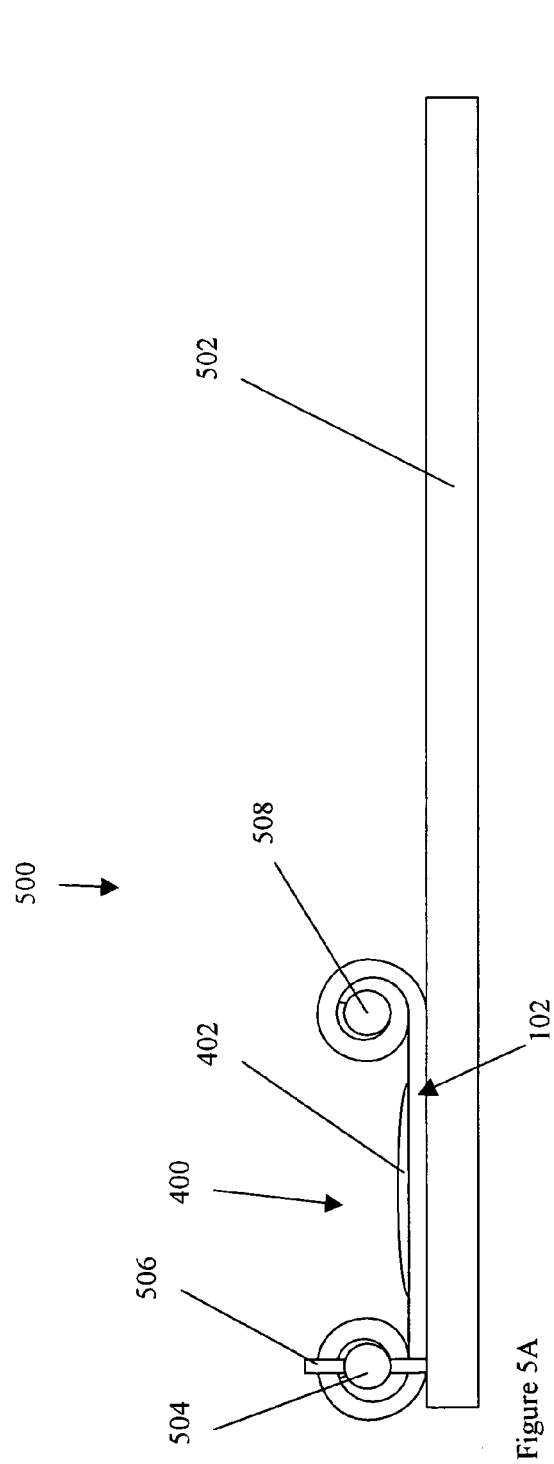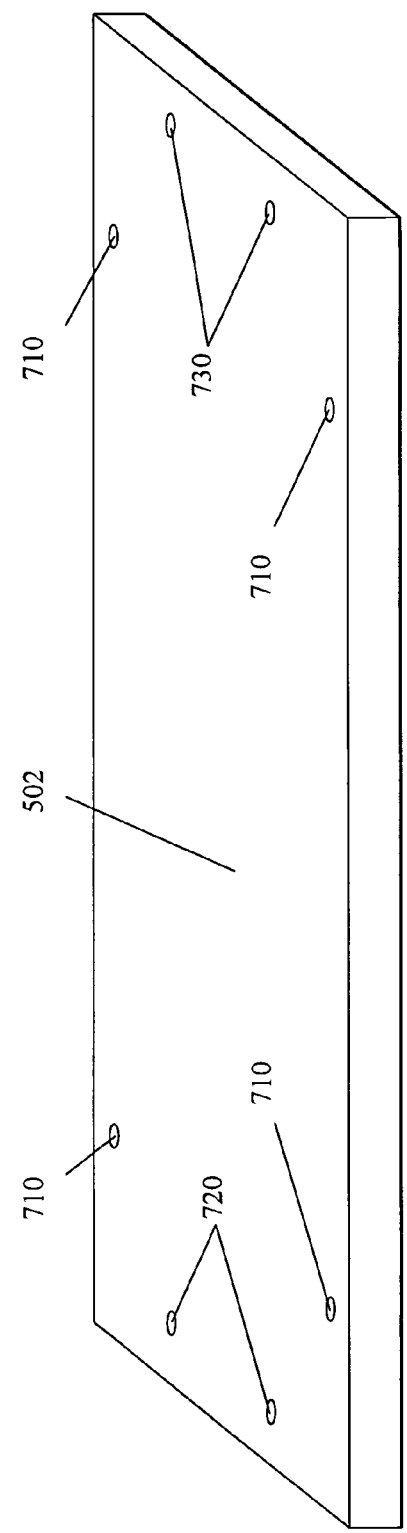

Figure 11

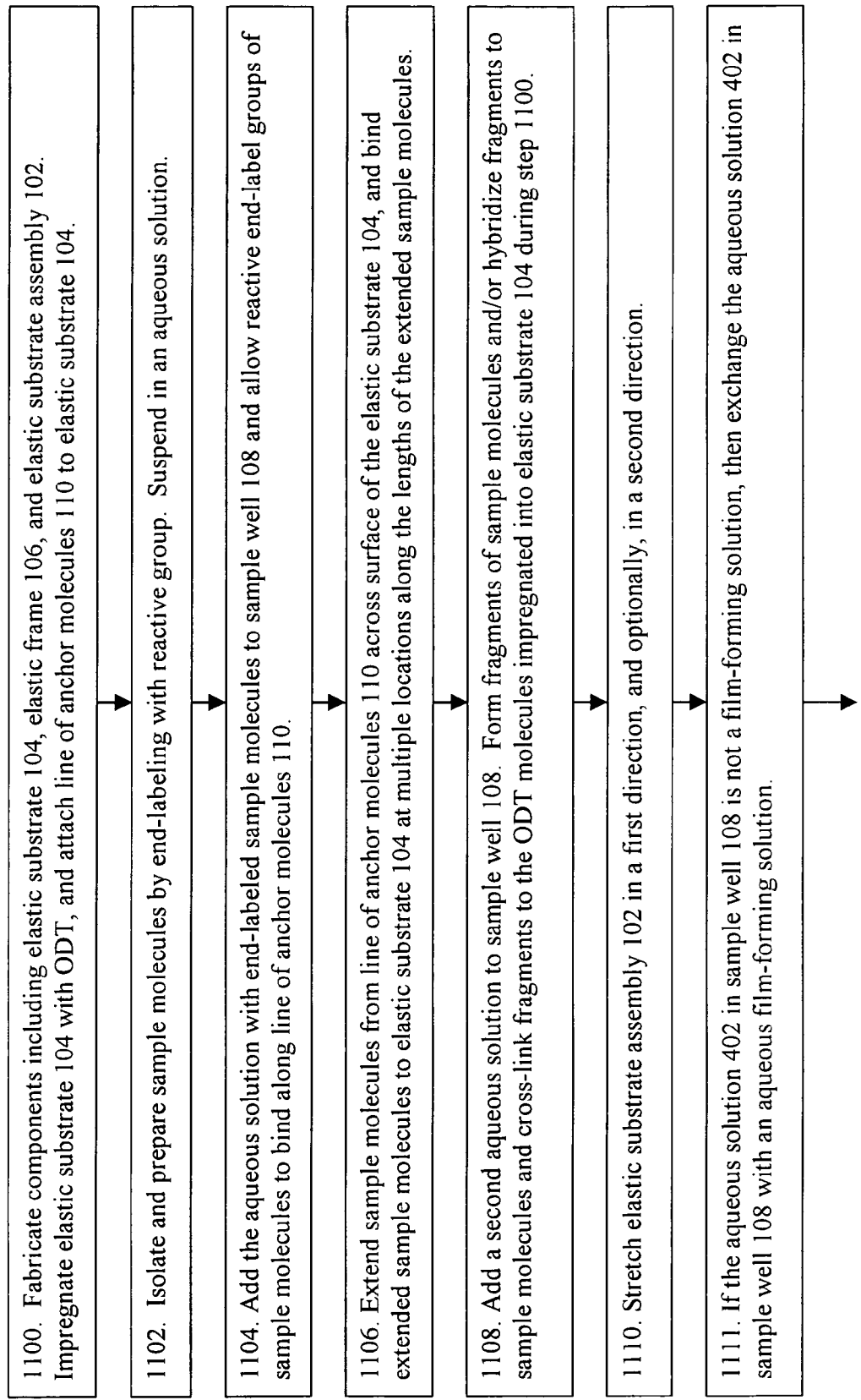

1100. Fabricate components including elastic substrate 104, elastic frame 106, and elastic substrate assembly 102. Impregnate elastic substrate 104 with ODT, and attach line of anchor molecules 110 to elastic substrate 104.

1102. Isolate and prepare sample molecules by end-labeling with reactive group. Suspend in an aqueous solution.

1104. Add the aqueous solution with end-labeled sample molecules to sample well 108 and allow reactive end-label groups of sample molecules to bind along line of anchor molecules 110.

1106. Extend sample molecules from line of anchor molecules 110 across surface of the elastic substrate 104, and bind extended sample molecules to elastic substrate 104 at multiple locations along the lengths of the extended sample molecules.

1108. Add a second aqueous solution to sample well 108. Form fragments of sample molecules and/or hybridize fragments to sample molecules and cross-link fragments to the ODT molecules impregnated into elastic substrate 104 during step 1100.

1110. Stretch elastic substrate assembly 102 in a first direction, and optionally, in a second direction.

1111. If the aqueous solution 402 in sample well 108 is not a film-forming solution, then exchange the aqueous solution 402 in sample well 108 with an aqueous film-forming solution.

Figure 11 - continued

Figure 12
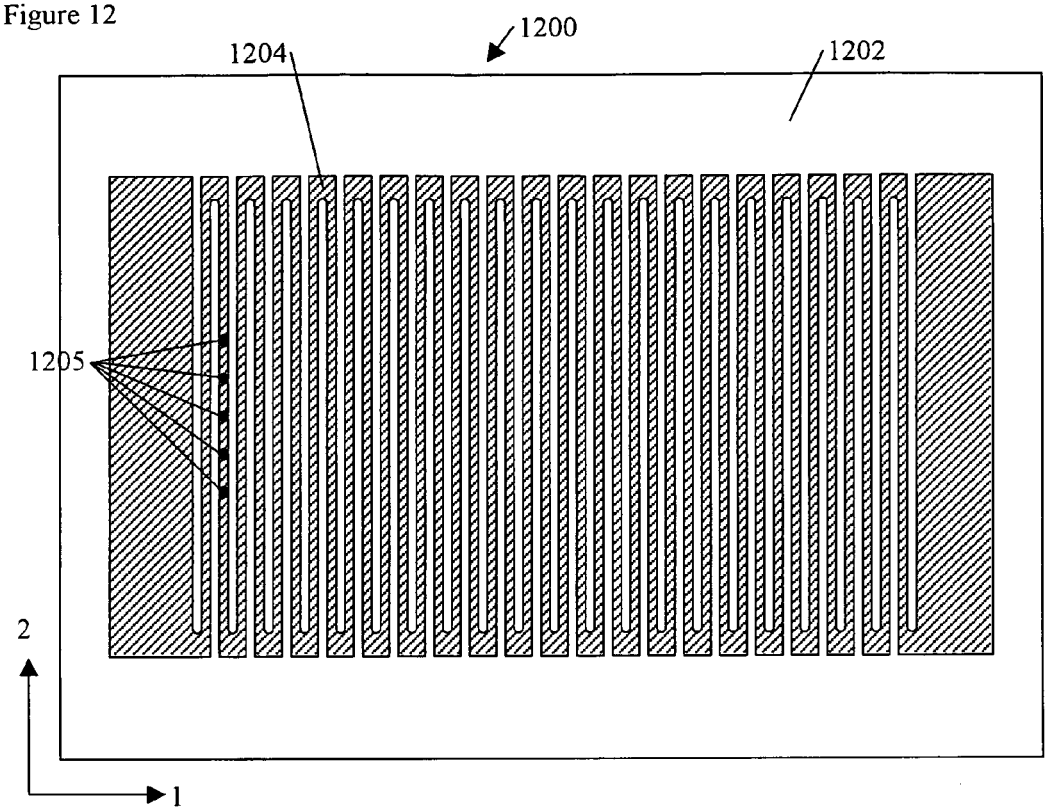
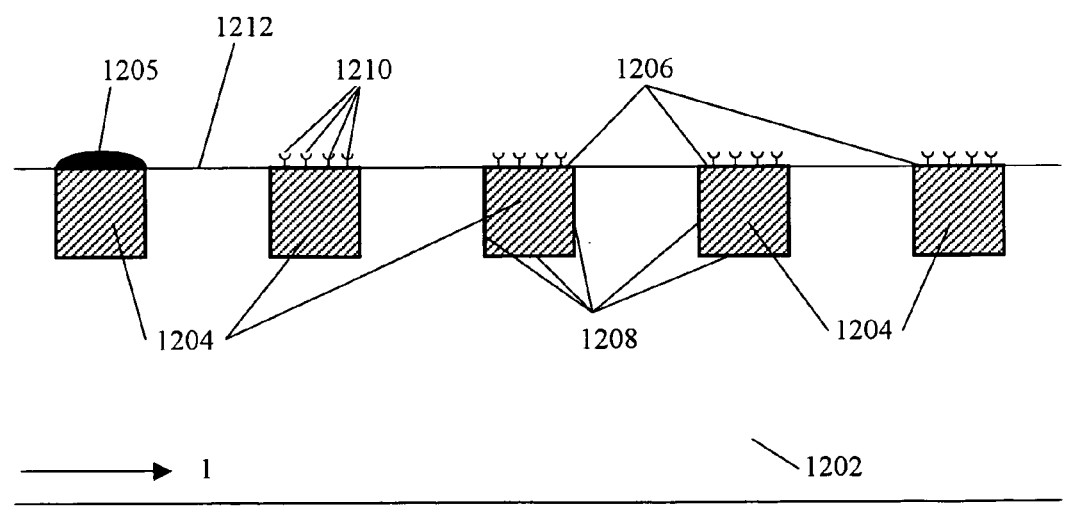
Figure 13

Figure 18

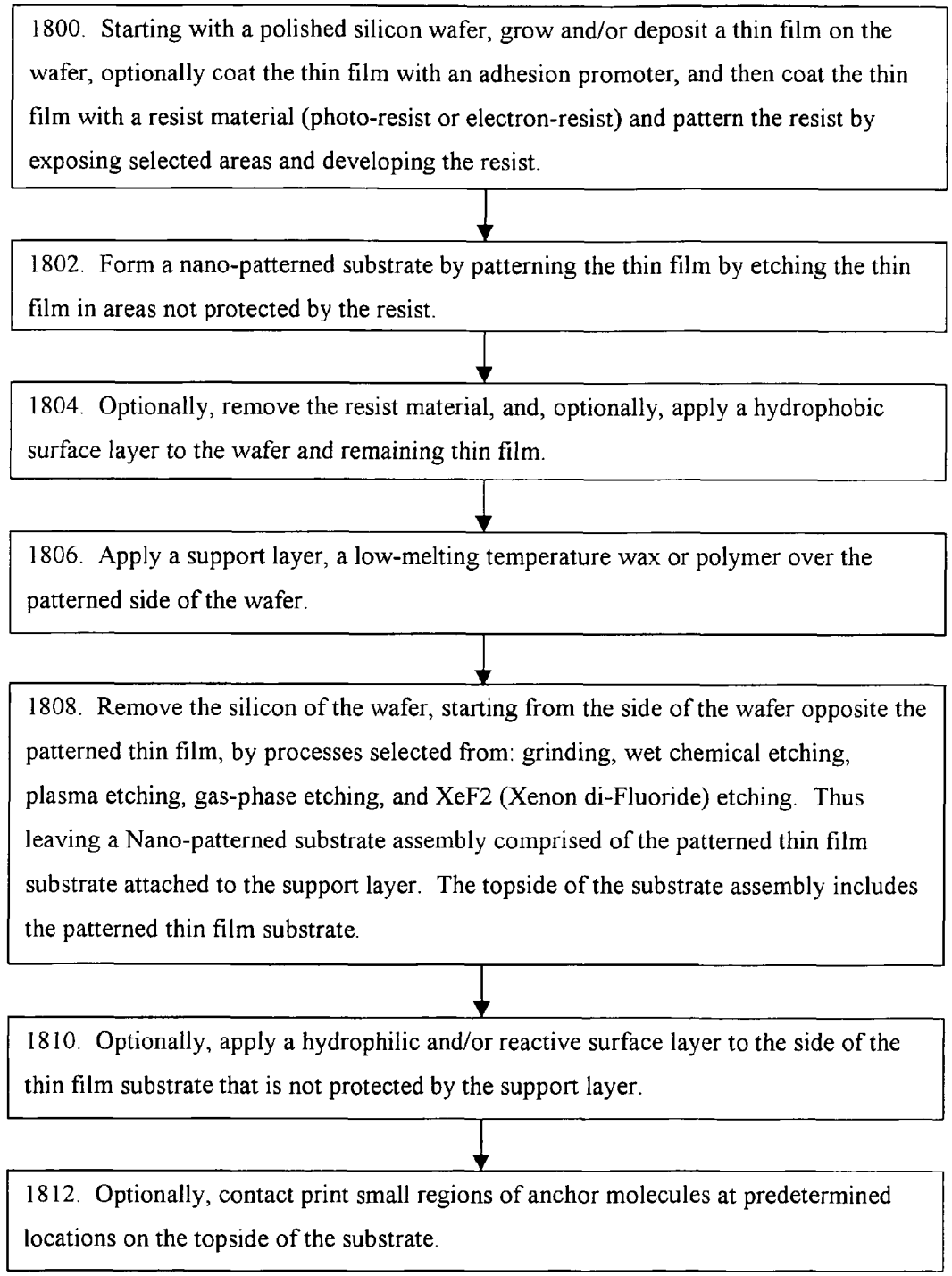

1800. Starting with a polished silicon wafer, grow and/or deposit a thin film on the wafer, optionally coat the thin film with an adhesion promoter, and then coat the thin film with a resist material (photo-resist or electron-resist) and pattern the resist by exposing selected areas and developing the resist.

↓

1802. Form a nano-patterned substrate by patterning the thin film by etching the thin film in areas not protected by the resist.

↓

1804. Optionally, remove the resist material, and, optionally, apply a hydrophobic surface layer to the wafer and remaining thin film.

↓

1806. Apply a support layer, a low-melting temperature wax or polymer over the patterned side of the wafer.

↓

1808. Remove the silicon of the wafer, starting from the side of the wafer opposite the patterned thin film, by processes selected from: grinding, wet chemical etching, plasma etching, gas-phase etching, and XeF2 (Xenon di-Fluoride) etching. Thus leaving a Nano-patterned substrate assembly comprised of the patterned thin film substrate attached to the support layer. The topside of the substrate assembly includes the patterned thin film substrate.

↓

1810. Optionally, apply a hydrophilic and/or reactive surface layer to the side of the thin film substrate that is not protected by the support layer.

↓

1812. Optionally, contact print small regions of anchor molecules at predetermined locations on the topside of the substrate.

Figure 19

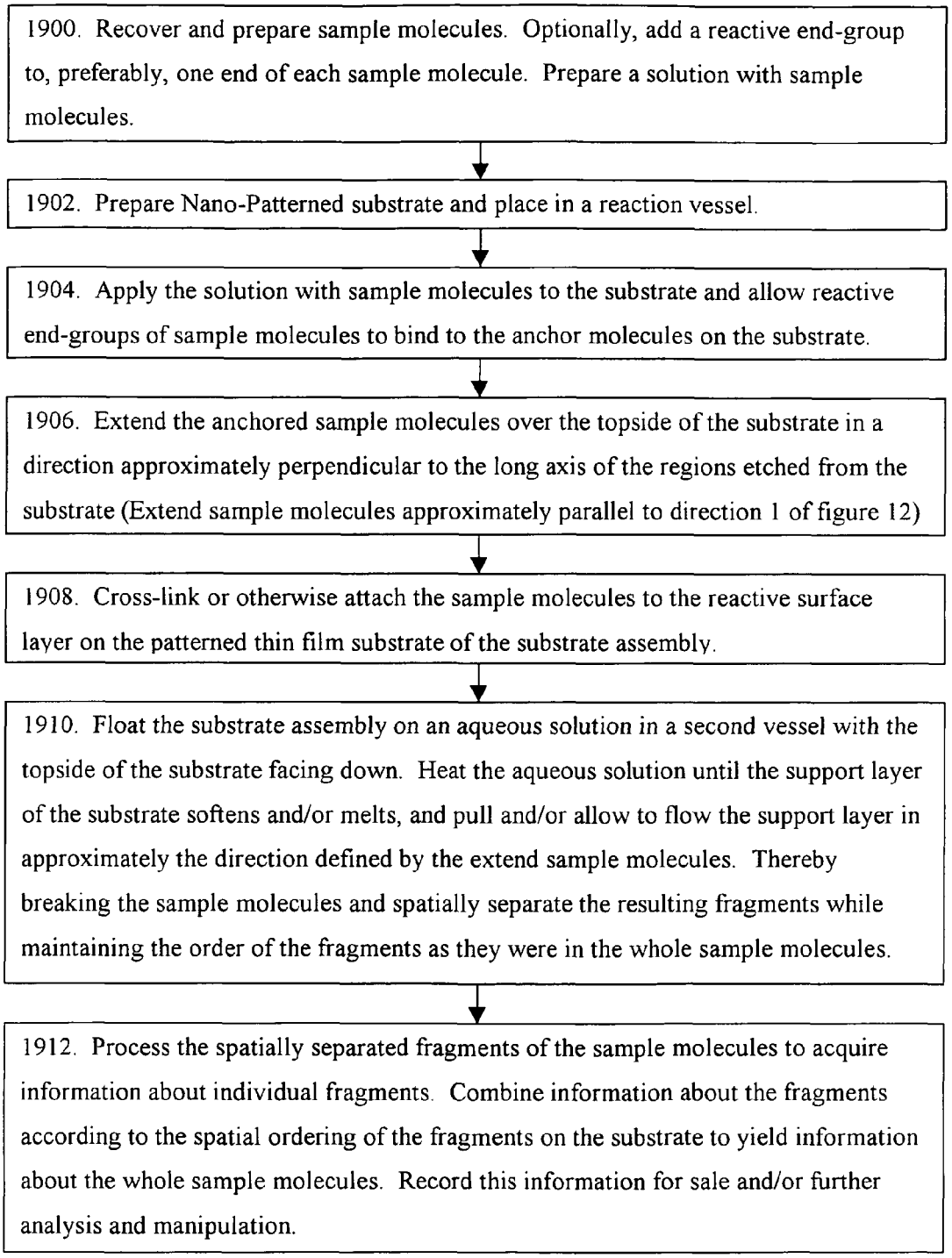

1900. Recover and prepare sample molecules. Optionally, add a reactive end-group to, preferably, one end of each sample molecule. Prepare a solution with sample molecules.

1902. Prepare Nano-Patterned substrate and place in a reaction vessel.

1904. Apply the solution with sample molecules to the substrate and allow reactive end-groups of sample molecules to bind to the anchor molecules on the substrate.

1906. Extend the anchored sample molecules over the topside of the substrate in a direction approximately perpendicular to the long axis of the regions etched from the substrate (Extend sample molecules approximately parallel to direction 1 of figure 12)

1908. Cross-link or otherwise attach the sample molecules to the reactive surface layer on the patterned thin film substrate of the substrate assembly.

1910. Float the substrate assembly on an aqueous solution in a second vessel with the topside of the substrate facing down. Heat the aqueous solution until the support layer of the substrate softens and/or melts, and pull and/or allow to flow the support layer in approximately the direction defined by the extend sample molecules. Thereby breaking the sample molecules and spatially separate the resulting fragments while maintaining the order of the fragments as they were in the whole sample molecules.

1912. Process the spatially separated fragments of the sample molecules to acquire information about individual fragments. Combine information about the fragments according to the spatial ordering of the fragments on the substrate to yield information about the whole sample molecules. Record this information for sale and/or further analysis and manipulation.

Figure 20

| 2000. Starting with a first polished silicon wafer, grow and/or deposit a thin film on the wafer, optionally coat the thin film with an adhesion promoter, and then coat the thin film with a resist material (photo-resist or electron-resist) and pattern the resist by exposing selected areas and developing the resist. |

↓

| 2002. Form a nano-patterned substrate by patterning the thin film by etching the thin film in areas not protected by the resist. |

↓

| 2004. Optionally, remove the resist material, and, optionally, apply a hydrophobic surface layer to the wafer and remaining thin film. |

↓

| 2006. Apply a thin support layer, a low-melting temperature wax or polymer over the patterned side of the wafer. Bond the first wafer to a second silicon wafer using the support layer as the bonding material. |

↓

| 2008. Remove the silicon of the first wafer, starting from the side of the first wafer opposite the patterned thin film, by processes selected from: grinding, wet chemical etching, plasma etching, gas-phase etching, and XeF2 (Xenon di-Fluoride) etching. Thus leaving a Nano-patterned substrate assembly comprised of the patterned thin film substrate attached to the support layer that is attached to the second silicon wafer. The topside of the substrate assembly includes the patterned thin film. |

↓

| 2010. Optionally, apply a hydrophilic and/or reactive surface layer to the side of the thin film that is not protected by the support layer. |

↓

| 2012. Optionally, contact print small regions of anchor molecules at predetermined locations on the topside of the substrate. |

Figure 21

| 2100. Recover and prepare sample molecules. Optionally, add a reactive end-group to, preferably, one end of each sample molecule. Prepare a solution with sample molecules. |

▼

| 2102. Prepare Nano-Patterned substrate and place in a reaction vessel. |

▼

| 2104. Apply the solution with sample molecules to the substrate and allow reactive end-groups of sample molecules to bind to the anchor molecules on the substrate. |

▼

| 2106. Extend the anchored sample molecules over the topside of the substrate in a direction approximately perpendicular to the long axis of the regions etched from the substrate (Extend sample molecules approximately parallel to direction 1 of figure 12) |

▼

| 2108. Cross-link or otherwise attach the sample molecules to the reactive surface layer on the patterned thin film regions of the substrate. |

▼

| 2109. Optionally, form a water-soluble coating over the top of the substrate. Coat over the top of the substrate with resist, expose the resist, develop the resist, etch the areas not protected by resist removing all portions of sample molecule in those locations, and remove the remaining resist. Dissolve any water-soluble coating. |

▼

| 2110. Place the substrate on an aqueous solution in a second vessel. Heat the aqueous solution until the support layer of the substrate assembly softens and/or melts, and pull the ends of the substrate in approximately the direction defined by the extend sample molecules. Thereby spatially separating the fragments while maintaining the order of the fragments as they were in the whole sample molecules. Harden the support layer by cooling the aqueous solution. |

▼

| 2112. Process the spatially separated fragments of the sample molecules to acquire information about individual fragments. Combine information about the fragments according to the spatial ordering of the fragments on the substrate to yield information about the whole sample molecules. Record this information for sale and/or further analysis. |

METHODS AND APPARATUSES FOR SPATIALLY SEPARATING MOLECULES ATTACHED TO A SUPPORT AND USES IN BIOTECHNOLOGY

CROSS-REFERENCE TO RELATED APPLICATIONS

This is a continuation-in-part of application Ser. No. 11/827,588, Filed on Jul. 11, 2007, now U.S. Pat. No. 7,745,129 B1, granted Jun. 29, 2010. This application claims the benefit of provisional patent application Ser. No. 61/004,137, filed Nov. 23, 2007 by the present inventor.

FEDERALLY SPONSORED RESEARCH

Not Applicable

SEQUENCE LISTING OR PROGRAM

Not Applicable

BACKGROUND OF THE INVENTION

1. Field of Invention

The invention generally relates to methods and apparatuses for investigating bio-molecules, and more specifically relates to methods and apparatuses used determining the base sequence of a nucleic acid or amino acid sequence of a protein.

2. Prior Art

The quest for low-cost methods of sequencing nucleic acids has been driven by its recognized importance to biological and medical research, and ultimately by its potential to impact the practice of medicine. Consequently, many techniques have been explored and reviewed, including variations on the classic chain-termination strategy of Sanger et al. PNAS 74:5463 5467 (1977), pyrosequencing, see for example Hyman E. D. Analytical Biochem 174:423 436 (1988), and other sequencing by synthesis or sequencing by incorporation methods, see for example Ronaghi et al. Science 281:363 365 (1998), sequencing by hybridization techniques, for example Strezoska et al. PNAS 88:10089 10093 (1991), including micro-array techniques, for example Chee et al., Science 274:610 614 (1996), and direct imaging of bases by micro-probes, for example Hansma et al. Science 256:1180 1184 (1992). A hybrid sequencing by hybridization and chain-termination technique is presented by Head et al. in U.S. Pat. No. 6,322,968 that employs probes having a short spacer arm. In their method, probes are lengthened by a polymerase and a chain-terminating and labeled nucleotide. The method is an array technique with the added complexity of an enzymatic process. In general, all these sequencing methods suffer from one or more of the following issues: short read lengths on un-correlated fragments, time-consuming cyclic processes conducted in expensive equipment, excessive consumption of expensive reagents, difficult and costly to analyze data sets, and reliance on alternate means for generating a sequence scaffold or map. The present invention is designed to circumvent these issues.

SUMMARY

Analysis of a long sample molecule can be efficiently managed by binding it at multiple locations along its length to a solid support, and then dividing it into multiple shorter pieces, fragments, some or all of which remain bound to the solid support and in the order in which they occurred in the original, whole sample molecule. The ordered fragments are then spatially separated so that each can be analyzed independently. Once the fragments have been analyzed, the data can be combined according to the ordering and spacing of the fragments along the solid support, thus providing a more complete analysis of the whole sample molecule.

The technique is particularly applicable to the sequencing of nucleic acid molecules, such as double-stranded DNA (dsDNA), single-stranded DNA (ssDNA), double-stranded RNA (dsRNA), single-stranded RNA (ssRNA), DNA/RNA heteroduplexes, mRNA, cDNA, snRNA, siRNA, miRNA, high molecular weight nucleic acids, and other nucleic acids. However, the methods and apparatuses are not limited to sequencing of nucleic acids, and they can be utilized with other types of analysis and other classes of sample molecules and molecular assemblies, including proteins. In this document, the terms "fragment", "element", and "biomolecule" are often employed as generic terms referring to fragmentary pieces or portions of a sample molecule or molecular assembly.

Efficiency is gained where the method and apparatus allow for the spatially separated fragments to be analyzed simultaneously. The methods and apparatuses presented here, in combination with inventions such as the sequencing method presented in U.S. patent application Ser. No. 11/827,588, support highly parallel, simultaneous processing and analysis. Novel methods, assemblies, and apparatuses for the spatial separation and processing of ordered fragments are presented herein.

Many alternate methods for spatially separating ordered fragments are presented in the following sections, and from these, many more will become apparent. For the purposes of this summary, a base method, referred to herein as the elastic substrate method, although alternate variations are presented that do not require elastic materials, is presented and summarized and is composed of the following general steps:

A) depositing of one or more sample molecules onto an elastic substrate,

B) temporary binding of the sample molecules to the elastic substrate at multiple locations along the sample molecules, C) cleaving the sample molecules at multiple locations so as to divide each sample molecule into multiple fragments, thus forming ordered sets of fragments wherein each fragment is temporarily bound to the elastic substrate, D) stretching the elastic substrate so as to spatially separate the temporarily bound fragments, and maintaining the elastic substrate in this stretched conformation, E) covering the temporarily bound fragments with an aqueous solution of a water-soluble film-forming material, F) evaporating the water from the aqueous solution, thereby partially encapsulating the temporarily bound fragments in a transfer substrate made of the film-forming material, G) removing the transfer substrate from the stretched elastic substrate such that the fragments remain with the transfer substrate, H) applying a relaxed elastic substrate to the transfer substrate such that the fragments become temporarily bound to the relaxed elastic substrate, I) dissolving the transfer substrate with water, J) repeating processes D) though I) until the desire extent of spatial separation between fragments is achieved, K) measuring the relative location and/or ordering of the fragments along the final elastic substrate, and sequencing the fragments or portions of the fragments, and L) combining the sequence data collected from the individual fragments in the order of the ordering data to generate useful sequence information and a sequence map representative of all or portions of the sample molecules.

The output of this method is set of spatially separated fragments, each fragment temporarily bound to a solid substrate, and the final ordering of the fragments along the substrate is the same as they were in the original sample molecule. The fragments can then be sequenced, (step K), by any sequencing method, including methods that proceed in-situ on the final elastic substrate and methods that require the fragments to be transferred to micro-well plates, beads, capillaries, or other vessels. The sequence data from the fragments is assembled according to the ordering of the fragments to form a more complete sequence for the entire sample molecule (step L). The methods presented can be used beneficially with any sequencing method, including those methods detailed in U.S. patent application Ser. No. 11/827,588, which provide for the simultaneous sequencing of all fragments.

The number of cycles of steps D through I, depends on the desired final amount of spatial separation between fragments, the original spatial separation between fragments, and the amount of stretching of each cycle's elastic substrate. An equation that relates these parameters reads: final spatial separation equals original spatial separation times the product of each cycle's amount of substrate stretching. Hence if the original spacing between fragments was 10 nm, and each elastic substrate is stretched to four times its relaxed length, then after one cycle the separation would be 40 nm, after two cycles it would be 160 nm, 640 nm after three, 2.56 um after four cycles, and so on. In a second example, six cycles of 4× stretching produces a total increase in spatial separation of 4096×, which is sufficient to increase the distance between bases along an extended DNA molecule, originally approximately 3-4 angstroms, to greater than 1 micron. The final amount of separation required such that fragments can be analyzed independently depends on the method of analysis and the apparatus employed. For methods that employ far-field optical data readout, such as detecting photons from fluorescent dye molecules or enzymatic reaction products using a fluorescent microscope, a final separation of 640 nm between fragments could be sufficient and 2.56 um is very likely sufficient. Hence the number of cycles required is moderate and readily achieved.

Note that where the original spacing between fragments is relatively larger and the resolving power of the readout apparatus is sufficient, then only a single substrate stretching operation may be needed. In which case the process flow above can be modified by optionally excluding steps E-J. In addition, the temporary bonding of the sample molecules outlined in steps B can be optionally replaced by a process of permanently bonding of the sample molecules to the elastic substrate.

There are several components to the method of repeated stretching cycles. The first is the methods and materials for the repeated temporary binding of molecular fragments to the elastic substrates. The second is the materials and methods of processing of the elastic substrates and transfer substrates.

One material set and method that allows for the repeated temporary binding of nucleic acid fragments to elastic substrates uses hydrophobic/hydrophilic forces. A particular combination uses elastomeric silicone as the elastic substrate material and 1-octadecanethiol cross-linked to the nucleic acid fragment as the temporary binding agent. This material set benefits from the ability of silicone to absorb hydrocarbon species such as octadecane and the hydrophilic nature of nucleic acid oligomers. Thus, an ambipolar molecule, in this case composed of a nucleic acid fragment (oligomer), a cross-linker, and 1-octadecanethiol, will be held at the interface region of a silicone substrate and an aqueous solution. The hydrocarbon tail of the 1-octadecanethiol will adsorb into the silicone substrate, and the polar nucleic acid oligomer will remain in the aqueous solution. Another benefit of this material set is that elastomeric silicone has excellent release properties, so that the solid transfer substrate can be easily peeled from the elastic substrate. Furthermore, elastomeric silicones that can be stretched to approximately four times their original length are common and varieties that can survive ten-fold elongation are available, thus minimizing the number of transfer cycles required to achieve a given total separation between fragments.

Examples of other molecules that when conjugated, either directly or through a cross-linker, to a nucleic acid oligomer provide for temporary binding to silicone rubber include: linear, branched, and cyclic hydrocarbons, fluorocarbons, or polydimethylsiloxanes (PDMS) with one or more reactive moieties, typically end-groups, to facilitate cross-linking to the oligomer. Examples include: 1-octadecylamine, 1-octadecene, octadecanol, phosphatidylethylamine, and 1-octadecanethiol (ODT). Note, the length or size and number of the non-polar groups effects the stability of the temporary binding to silicone elastomer, and lengths other than those given in these examples may be beneficially employed. Furthermore, the choice of reactive moiety is driven by the cross-linking agent selected and other process considerations.

The next key component is the transfer substrate. Water-soluble film-forming materials that can be beneficially used to form transfer substrates include: partially hydrolyzed polyvinyl alcohol (PVOH) such as Elvanol 51-05 or 52-22 (Dupont, USA), fully hydrolyzed PVOH, polyethylene glycol (PEG), DNA, high molecular weight nucleic acids, polyethyleneoxide (PEO), polyethyleneimine (PEI), polyvinylpyrrolidone (PVP), salt, sugar, glycerol (glycerin or glycerine), and mixtures of these. One or a mixture of these materials is dissolved in a suitable solvent, typically de-ionized water (DI) or buffered DI, such as TE buffer (Tris-EDTA), MES buffer, phosphate buffered saline (PBS), or SSC buffer, to make a film-forming solution. Evaporating the volatile components, typically only water, from the film-forming solution produces the transfer substrate. The time required for evaporation can be reduced by heating of the solution and greatly reduced by using vacuum evaporation in a suitable vacuum chamber system or by blowing dry air or nitrogen over the solution. Alternately, a pre-formed film of the water-soluble film forming materials can be used and laminated over the elastic substrate and fragments to affect their transfer to the transfer substrate.

In an alternate process, freezing the film-forming solution produces the transfer substrate. In this case the transfer substrate is a frozen solid, and no evaporation or dissolution steps are required. Accordingly, the film-forming solution can be pure DI, a suitable buffer, such as TE, MES, PBS, or SSC, or an aqueous solution incorporating glycerol, and/or water-soluble polymers such as DNA or others such as those listed in the preceding paragraph. Thus an alternate to step F) of the base method listed above is as follows: cooling the stretched elastic substrate and covering film-forming solution below the freezing point of the film-forming solution, freezing the film-forming solution, and encapsulating the temporarily bound fragments in a transfer substrate formed by the frozen film-forming solution. In process steps G) and H), the transfer substrate and relaxed elastic substrate must be kept cold such that the transfer substrate remains a frozen solid. Process step I) then becomes: melting the transfer substrate by warming the relaxed elastic substrate and transfer substrate above the melting point of the film-forming solution. The other process steps remain as listed above. This alternate process benefits from the relative rapidity with which the transfer substrate can be formed and later melted.

Several methods are available for establishing temporary bonds to the relaxed substrate on the second and later cycles of the base method (step H of the base method listed above). The simplest method entails laminating the relaxed elastic substrate over the transfer substrate, such that the non-polar groups on the molecules that facilitate the temporary bonding, that are exposed on the surface of the transfer substrate, are brought into intimate contact with the surface of the relaxed elastic substrate. The non-polar groups absorb into the surface of the elastic substrate, thus establishing the temporary bonds. An alternate method is to cast the relaxed elastic substrate directly on the surface of the transfer substrate. In this method, an uncured PDMS liquid is poured or otherwise deposited onto that face of the transfer substrate from which the temporary binding molecules are protruding, and the PDMS is cured to form the relaxed elastic substrate. Suitable uncured PDMS materials include Sylgard 186 and Sylgard 184 (Dow Corning Corp, Midland, Mich.) which can be cured at room temperature or more rapidly with mild heating.

Note that the elastic substrate may be stretch in one or two perpendicular dimensions, and the amount, direction, and number of dimensions in which the elastic substrate is stretched can vary with each cycle through the base method as benefits the process.

An alternate method for spatially separating fragments of a long sample molecule bound at multiple locations along its length to a solid substrate employs a thin substrate that is either pre-cut or readily fractured such that regions of the substrate can be easily moved apart from each other. The optimum width of any pre-cut features is small, hence this method is referred to herein as the nano-patterned substrate method, although in some embodiments no patterning is required. The thin substrate can be mounted on a wax support that holds the substrate together while the wax is solid, but allows the thin substrate to be easily, or even spontaneously, fractured upon melting of the wax. Furthermore, the thin substrate can be specially fabricated such that the substrate will fracture preferentially along predetermined lines. Support materials other than wax can also be employed, such as blow-moldable plastics, thermoplastic materials, moderately low melting temperature materials such as sugar, salt, low melting temperature eutectics such as low melting temperature solders, indium, mercury, gallium, lead, wafer bonding adhesives, such as Protek coating agents (available from Brewer Science, Rolla, Mo.), solvent soluble solid materials, water soluble solids (PVOH, etc.), silicone gel, silicone elastomer, other elastic solids, or the thin substrate can be unsupported.

A further alternate method is detailed that employs an accordion folded or pleated substrate and is referred to herein as the accordion folded substrate method. Such a substrate can be compressed, such that the folds are close together, and the sample molecule extended across the tops of many folds, in a direction approximately perpendicular to the long axis of the folds, and attached to the many folds. The sample molecule is then divided into fragments, by any means, including mechanical stretching, and the substrate is extended in the direction perpendicular to the long axis of the folds, thus unfolding the folds, whereby the fragments are spatially separated.

Furthermore, the various methods can be applied sequentially or simultaneously. For example, a sample molecule may be initially processed using the elastic substrate method to generate fragments and provide an initial amount of spatial separation, and the fragments then transferred to an accordion folded substrate for further spatial separation. Alternately, an accordion folded elastic substrate can be employed, wherein the initial spatial separation occurs as the folds are unfolded, and addition separation added by stretching of the elastic substrate, including stretching of the elastic substrate in the direction of the long axis of the folds. Other combinations of methods are also possible.

For clarity, this Summary has focused on only a few embodiments, and many variations on the base method listed above and of the apparatuses detailed are presented in the Detailed Description section, below. With knowledge of these variations, many further alternate embodiments become apparent to one skilled in the art. Hence this Summary is not to be construed as limiting the scope of the embodiments, but as a summary of a few of the many possible alternate embodiments. Thus the scope of the embodiments should be determined by the claims appended to the patent application and their legal equivalents, rather than by the examples given.

DRAWINGS

In the drawings, closely related figures have the same number but different alphabetic suffixes.

FIG. 5A illustrates a side view of the elastic substrate assembly attached a one end to a support structure.

FIG. 5B illustrates a perspective view of the support structure.

FIG. 12 illustrates a top view of a Nano-Patterned substrate.

FIG. 13 illustrates a cross-section through a portion of the Nano-Patterned substrate of FIG. 12.

FIG. 18 illustrates a process flow for fabricating a Nano-Patterned substrate.

FIG. 19 illustrates a process flow for analyzing sample molecules by using a Nano-Patterned substrate.

FIG. 20 illustrates a process flow for fabricating an alternate Nano-Patterned substrate.

FIG. 21 illustrates an alternate process flow for analyzing sample molecules by using an alternate Nano-Patterned substrate.

DETAILED DESCRIPTION

Detailed Description of Preferred Embodiment

Figure 1:
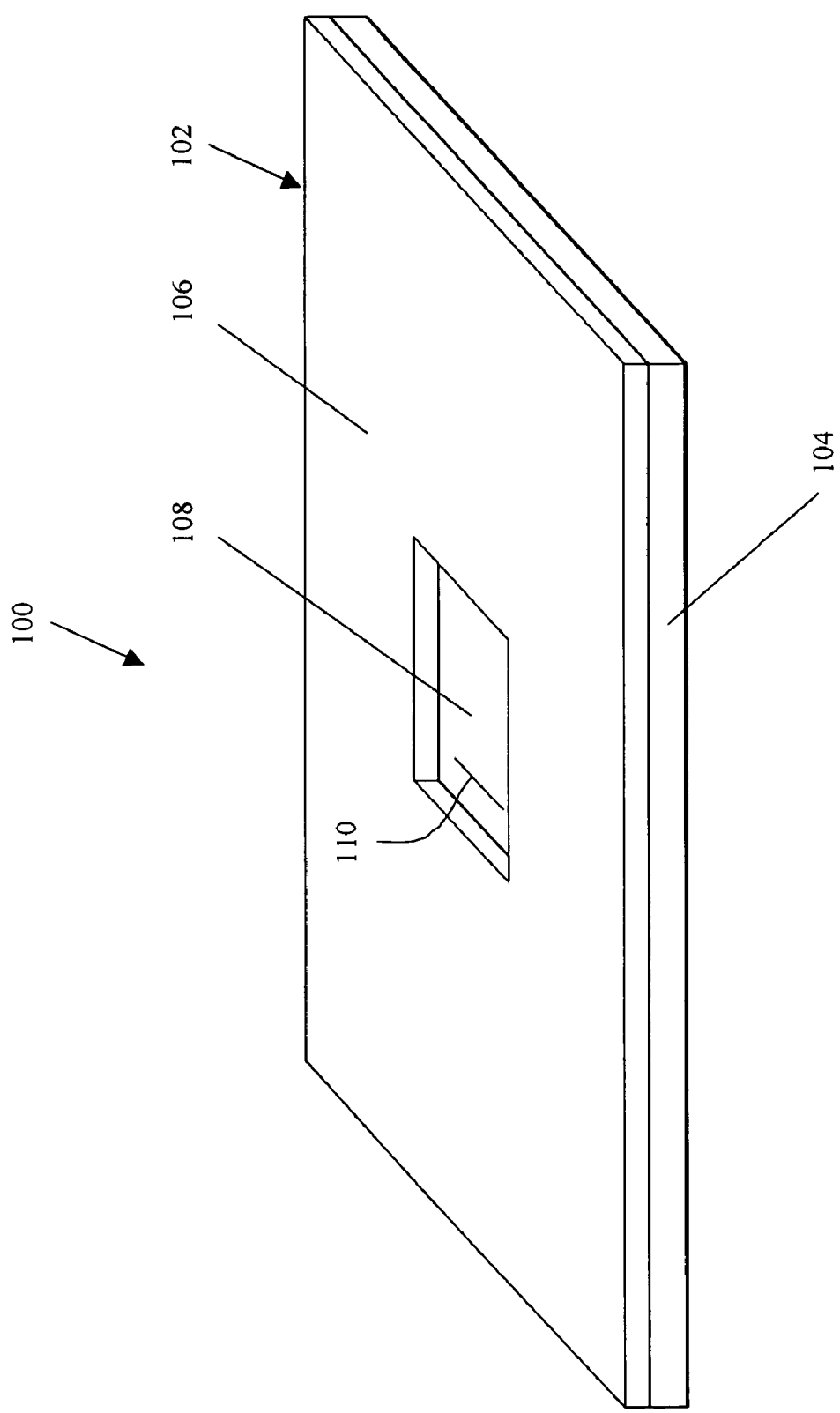
FIG. 1 illustrates a perspective view of an elastic substrate assembly with a sample well.

Features of the preferred embodiment are illustrated in FIGS. 1-10. FIG. 1 illustrates assembly 100, which is composed of a relaxed elastic substrate assembly 102 and a line of anchor molecules 110. Elastic substrate assembly 102 is composed of an elastic substrate 104 and an elastic frame 106. An opening in elastic frame 106 forms sample well 108. The line of anchor molecules 110 are attached to the top surface of elastic substrate 104 in the region exposed within the sample well 108. Elastic frame 106 is in intimate contact with the top surface of elastic substrate 104. Both 104 and 106 are fabricated of silicone rubber of a type which has a low durometer of less than roughly 50 A, and preferably in the range of approximately 5 A to 30 A, and high ultimate elongation, typically greater than roughly 100% and preferably greater than roughly 400%. The relaxed thickness of elastic substrate 104 and elastic frame 106 are typically less that 6 mm each, and preferably in the range of 0.5 mm to 3 mm thick. The length and width of relaxed elastic substrate 104 and elastic frame 106 are typically 10 cm to 40 cm larger that the length and width of sample well 108. The dimensions of sample well 108 of the first relaxed elastic substrate assembly 102 is typically in the range from roughly 5 mm×5 mm to 30 mm×100 mm, and any other dimensions which can be readily handled are acceptable. The line of anchor molecules 110 can be an approximate line or narrow region of streptavidin molecules that are cross-linked or non-specifically bound to the silicone surface of elastic substrate 104. Alternately, the line of anchor molecules 110 can be a line of small dots of anchor molecules.

Figure 2:
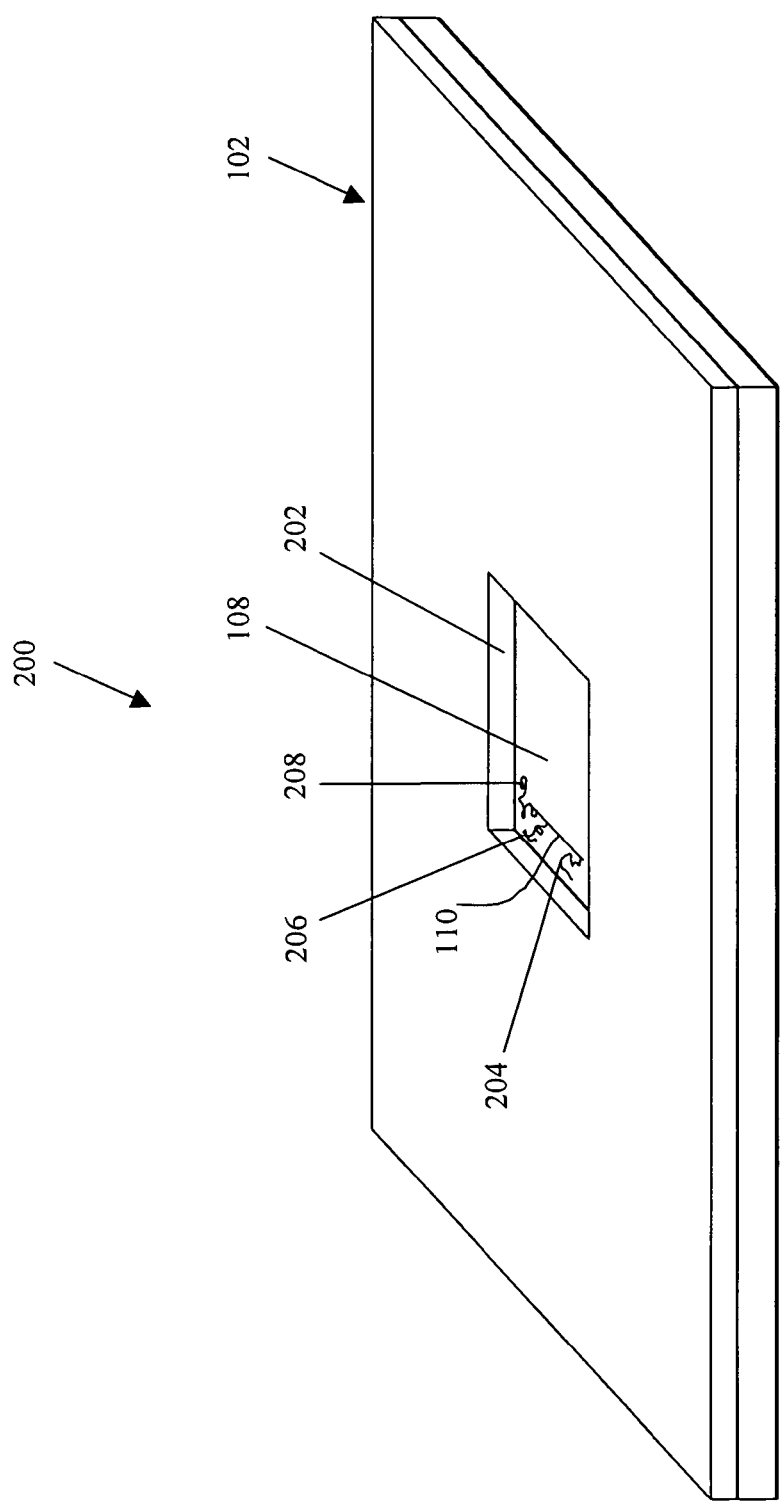
FIG. 2 illustrates a perspective view of the elastic substrate assembly with anchored sample molecules within the sample well.

FIG. 2 illustrates assembly 200, which is composed of elastic substrate assembly 102, line of anchor molecules 110, a volume of aqueous solution 202 filling sample well 108, and sample molecules 204, 206, and 208. Each sample molecule, 204, 206, and 208, is bound to one or more anchor molecules along the line of anchor molecules 110. Three sample molecules 204, 206, and 208 are illustrated in FIG. 2 for clarity, however, it is possible to have fewer or more, including a large plurality of, sample molecules. Sample molecules 204, 206, and 208 may be double-stranded DNA (dsDNA), single-stranded DNA (ssDNA), RNA, mRNA, nucleic acid molecules, and other sample molecules. Each sample molecules 204, 206, and 208 includes one or more biotin molecules conjugated to the sample molecule, preferably at or near to one end of the sample molecule. One or more of these biotin molecules is bound to one or more of the individual streptavidin anchor molecules that comprise the line of anchor molecules 110.

Figure 3:
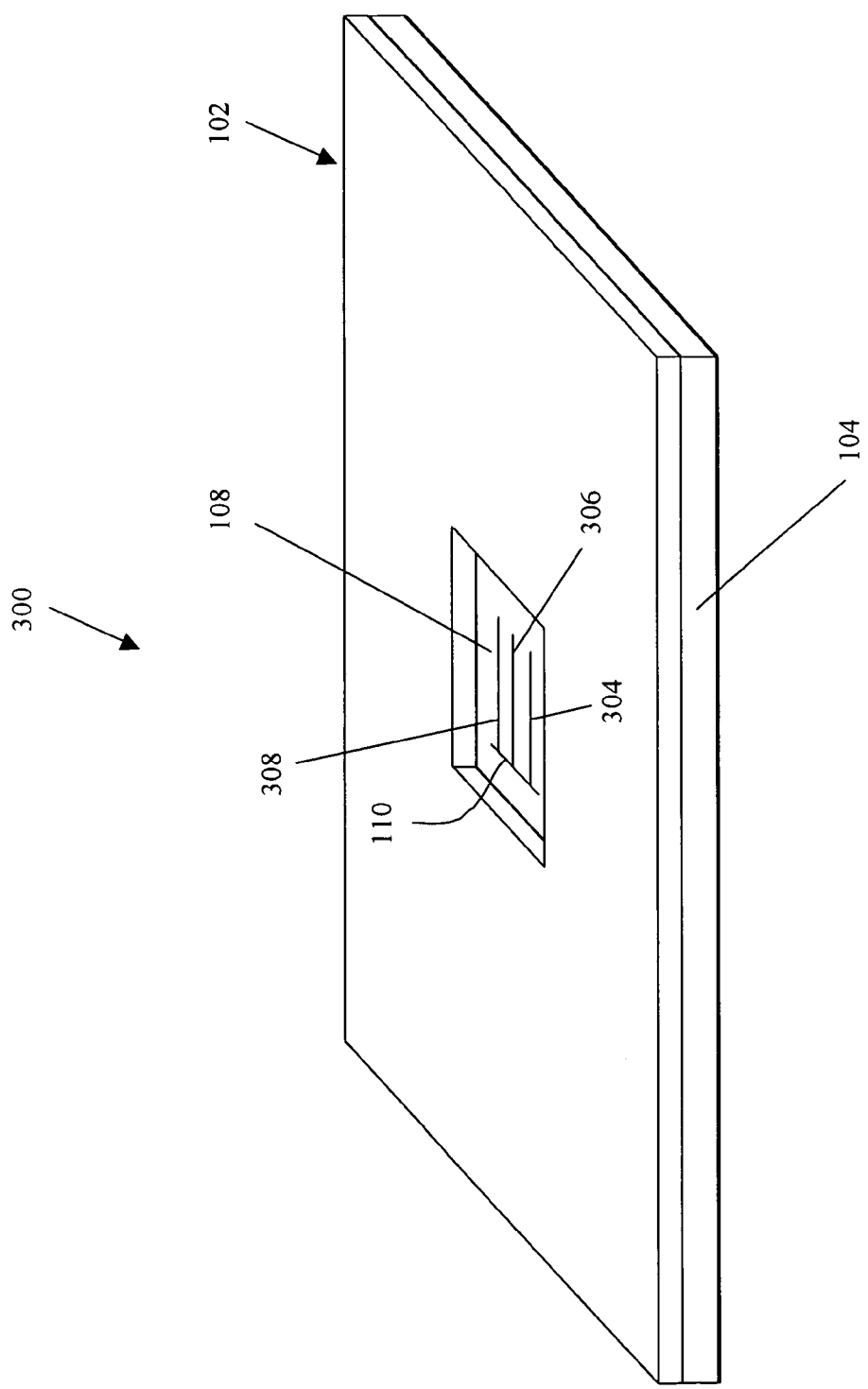
FIG. 3 illustrates a perspective view of the elastic substrate assembly with extended sample molecules within the sample well.

FIG. 3 illustrates assembly 300, which is composed of elastic substrate assembly 102 that includes sample well 108, line of anchor molecules 110, and extended sample molecules 304, 306, and 308. Extended sample molecules 304, 306, and 308 are the same sample molecules 204, 206, and 208, respectively, of FIG. 2, and hence the sample molecules 304, 306, and 308 are bound to anchor molecules along the line of anchor molecules 110. In assembly 300, the sample molecules 204, 206, and 208 have been extended to generate extended sample molecules 304, 306, and 308, which, in addition to being bound to the line of anchor molecules 110, are non-specifically bound at multiple locations along their lengths to the top surface of elastic substrate 104.

Figure 4:
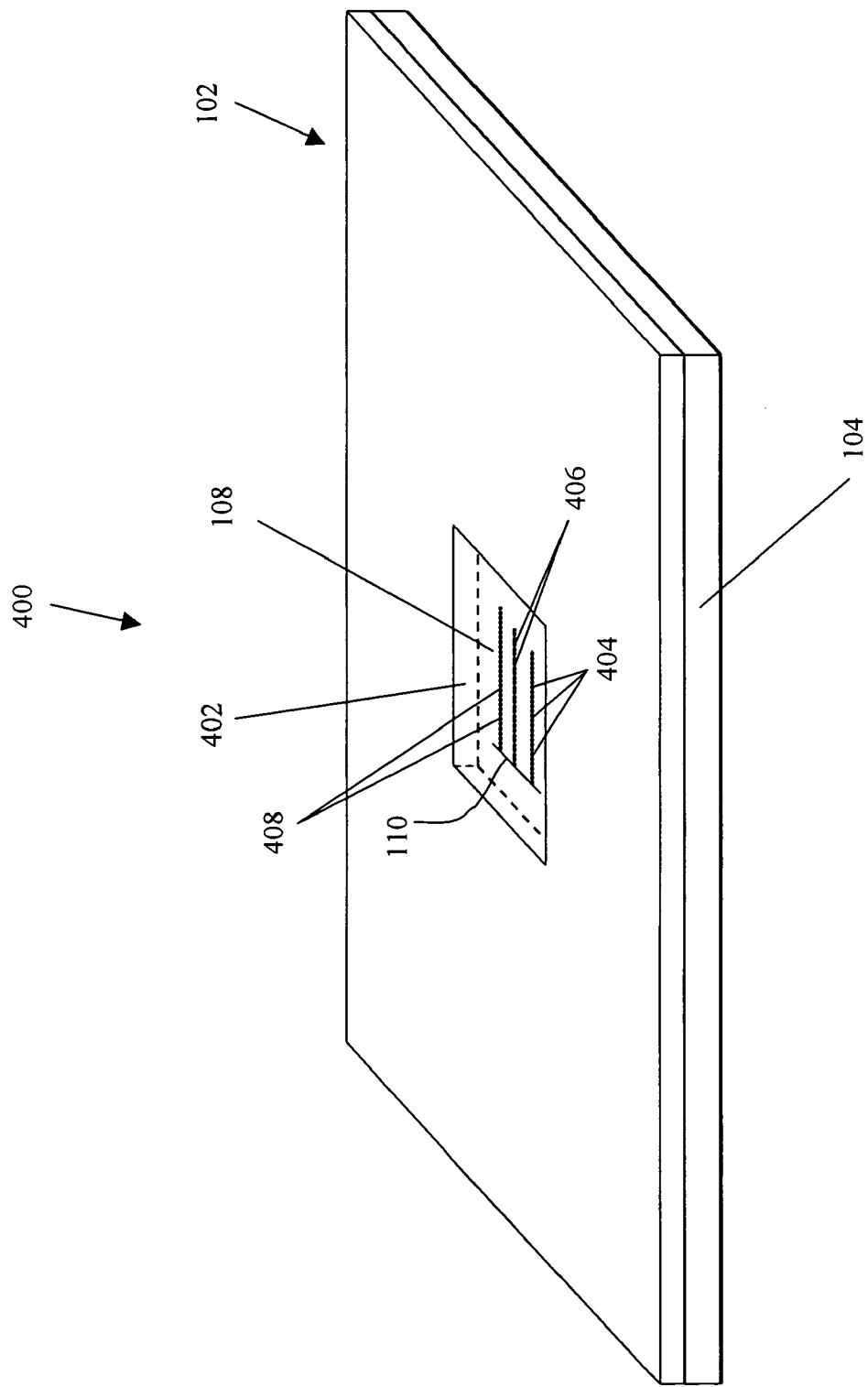
FIG. 4 illustrates a perspective view of the elastic substrate assembly with ordered fragments cross-linked to temporary binding molecules within the sample well.

FIG. 4 illustrates assembly 400, which is composed of elastic substrate assembly 102, line of anchor molecules 110, a volume of aqueous solution 402 filling sample well 108, and three sets of ordered fragments 404, 406, and 408 of the sample molecules 304, 306, and 308, respectively, of FIG. 3. Furthermore, each of the fragments 404, 406, and 408 is temporarily bound to the elastic substrate 104. To avoid confusion in FIG. 4, only two or three of the individual fragments 404, 406, and 408 are labeled, but it is to be understood that each dot along the lines of adjacent dots represents another fragment 404, 406, or 408. As the fragments 404 are ordered fragments cleaved from the extended sample molecule 304 of FIG. 3, the order of the fragments 404 along elastic substrate 104 is the same as their original order within sample molecule 304. Furthermore, the process of forming the fragments 404 and of temporarily bonding them to elastic substrate 104 results in the fragments 404 retaining approximately the same location on the elastic substrate 104 as they had within the extended sample molecule 304 of FIG. 3. The same relations apply between fragments 406 and 408 and extended sample molecules 306 and 308, respectively. The temporary bonds between the fragments 404, 406, and 408 and elastic substrate 104 are through a cross-link or cross-links between each of the fragments 404, 406, and 408 and one or more 1-octadecanethiol molecules adsorbed into the elastic substrate 104.

FIG. 5A illustrates assembly 500, which is comprised of assembly 400, structural support element 502, dowel pins 506, and rods 504 and 508. Two dowel pins 506 are included in assembly 500, however only one is shown in FIG. 5A. The second dowel pin 506 is located near the far end of rod 504 and is thus not visible behind the dowel pin 506 shown. Rods 504 and 508 are longer than elastic substrate assembly 102 is wide when relaxed. Each of rods 504 and 508 include two through-holes that pass through the center of the rods and are aligned perpendicular to the axis of rods, and one through-hole is located near each of the two ends of each of rods 504 and 508. As illustrated in FIG. 5B, structural support element 502 includes four holes 710, two holes 720, and two holes 730 drilled into its top surface. The two holes 720 are designed to accept dowel pins 506, such that the dowel pins 506 can be inserted through the through-holes in rod 504 and into holes 720 in the structural support element 502 so that rod 504 is securely held in place in the location illustrated in FIG. 5A. Two opposing ends of elastic substrate assembly 102 are wrapped around rods 504 and 508, and rod 504 is fixed to the structural support element 502 by means of the dowel pins 506 being inserted through rod 504 and into the two holes 720. Which of the two opposing ends of elastic substrate assembly 102 are wrapped around rods 504 and 508 is selected based on the desired first direction of substrate stretching. Elastic substrate assembly 102 is wrapped around rods 504 and 508 by manually placing each rod, one at a time, on one of the two opposing ends of elastic substrate assembly 102 and rolling the rod, 504 or 508, in towards the center of elastic substrate assembly 102 while holding that end of 102 against the rod with one's fingers. Rod 504 can be done first, and then held in place with dowel pins 506. Rod 508 is held by hand under slight tension so that elastic substrate assembly 102 remains wrapped around rod 508. A volume of aqueous solution 402 is maintained in the sample well within elastic substrate assembly 102.

Structural support element 502, rods 504 and 508, and dowel pins 506 can be made from any suitable material of sufficient strength and rigidity, such as metal, preferably aluminum or stainless steel, rigid plastic, or wood.

Figure 6:
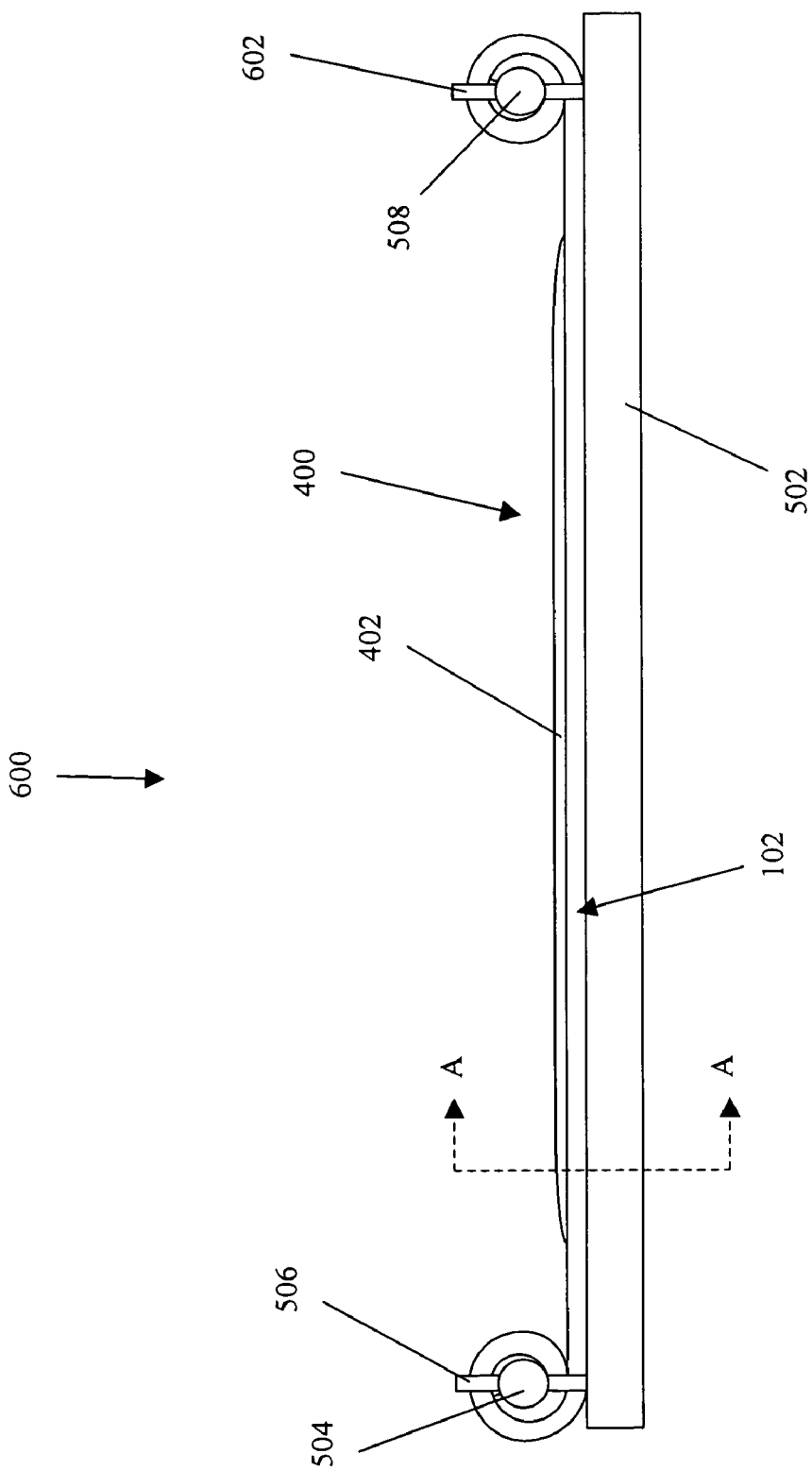
FIG. 6 illustrates a side view of the elastic substrate assembly stretched in a first direction and attached at both ends to the support structure.

FIG. 6 illustrates assembly 600, which includes all of the components of assembly 500, including assembly 400, plus two dowel pins 602. In addition, elastic substrate assembly 102 has been stretched in a first direction, and an additional volume of aqueous solution may have been added to the volume of aqueous solution 402. As explained for FIG. 5, there are two dowel pins 602, however only one can be seen in the side-view of FIG. 6. Dowel pins 602 hold rod 508 in place over structural support element 502. Dowel pins 602 pass through the through-holes in rod 508 and into the two holes 730, illustrated in FIG. 5B, in the top surface of structural support element 502. Elastic support assembly 102 is stretched by pulling on rod 508 while holding structural support element 502 in place. Dowel pins 602 can be fabricated from any suitable material of sufficient strength and rigidity, such as metal, rigid plastics, and wood, and preferably from aluminum or stainless steel.

Figure 7B:
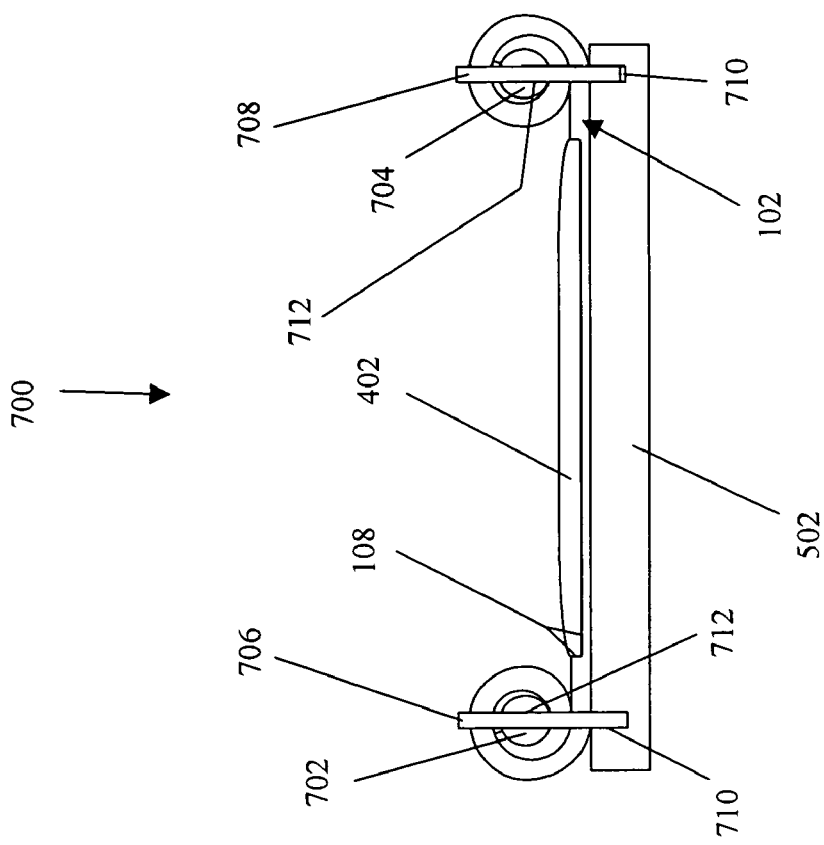
FIG. 7B illustrates a cross-section view at section A-A of FIG. 6 after stretching of the elastic substrate assembly in a second direction, with elements for holding elastic substrate assembly in the stretched conformation.
Figure 7A:
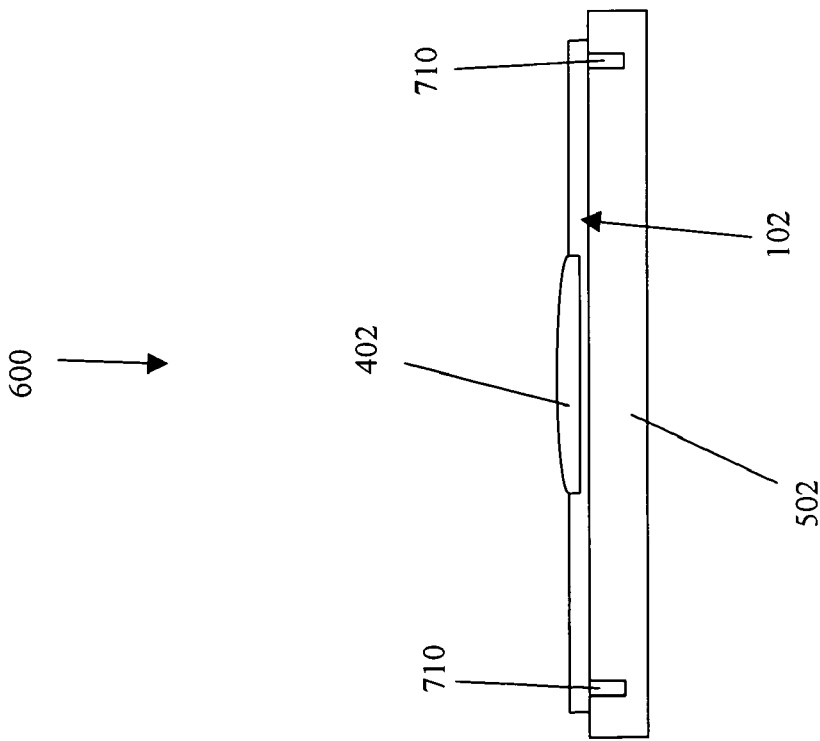
FIG. 7A illustrates a cross-section view at section A-A of FIG. 6 before stretching of the elastic substrate assembly in a second direction.

FIGS. 7A and 7B illustrate end-on views of section A-A of FIG. 6. FIG. 7A illustrates assembly 600 at section A-A of FIG. 6. Included in FIG. 7A are structural support element 502, elastic substrate assembly 102, the volume of aqueous solution 402, and two of the holes 710.

FIG. 7B illustrates assembly 700. In FIG. 7B, elastic substrate assembly 102 has been stretched in a second direction. Referring to FIG. 7B, assembly 700 comprises all of the elements of assembly 600 plus rods 702 and 704, and dowel pins 706 and 708 set in holes 710. There are two dowel pins 706, two dowel pins 708, and four holes 710 in assembly 700, although only one of each dowel pin 706 and 708 and two holes 710 are visible in FIG. 7B. Rods 702 and 704 each include two through-holes 712, one near each end, that extend through the rods, centered along a diameter of the rods and aligned perpendicular to the axis of the rods. Only two of through-holes 712, one in each of rods 702 and 704, are visible in FIG. 7B. The axes of the two through-holes 712 in each rod are parallel. The two opposing ends of elastic substrate assembly 102 that are not wrapped around rods 504 and 508 are wrapped around rods 702 and 704, and the rods 702 and 704 are pulled away from each other such that the elastic substrate assembly 102 is stretched in the second direction. During stretching, an additional volume of aqueous solution may be added to the volume of aqueous solution 402 to keep the sample well 108 filled. Dowel pins 706 and 708 are then used to hold rods 702 and 704 in place. Dowel pins 706 are inserted through the through-holes 712 in rod 702 and into two holes 710, thus fixing rod 702 to structural support element 502. Likewise, rod 704 is held in place to 502 by dowel pins 708 inserted into the other two holes 710. The tension in the stretched elastic substrate assembly 102 holds the portions of 102 that are wrapped around the rods 504, 508, 702, and 704 in place and prevents them from unwrapping as long as the dowel pins are in place and inserted into the holes in the structural support element 502.

Rods 702 and 704 and dowel pins 706 and 708 can be fabricated from any suitable material of sufficient strength and rigidity, including metal, rigid plastics, and wood, and preferably stainless steel or aluminum. Rods 504 and 508 are longer than the relaxed width of the elastic substrate assembly 102, and rods 702 and 704 are typically approximately 4 cm to 20 cm shorter than the distance between holes 720 and 730. All rods have diameters usually in the range of roughly 0.5 cm to 4 cm. Dowel pins can be of any suitable size and are usually 5 cm to 8 cm long and 1 mm to 6 mm in diameter. Holes 710, 720, and 730 are of diameter sufficient to snuggly accept the dowel pins and are typically in the range of roughly 1 cm to 5 cm in depth. Structural support element 502 is at least as thick as the depth of the holes, and is of length and width sufficient to contain all holes 710, 720, and 730. The distance between holes 720 and 730, and between holes 710 is determined by the desire amount of stretching of the elastic substrate assembly.

Figure 8:
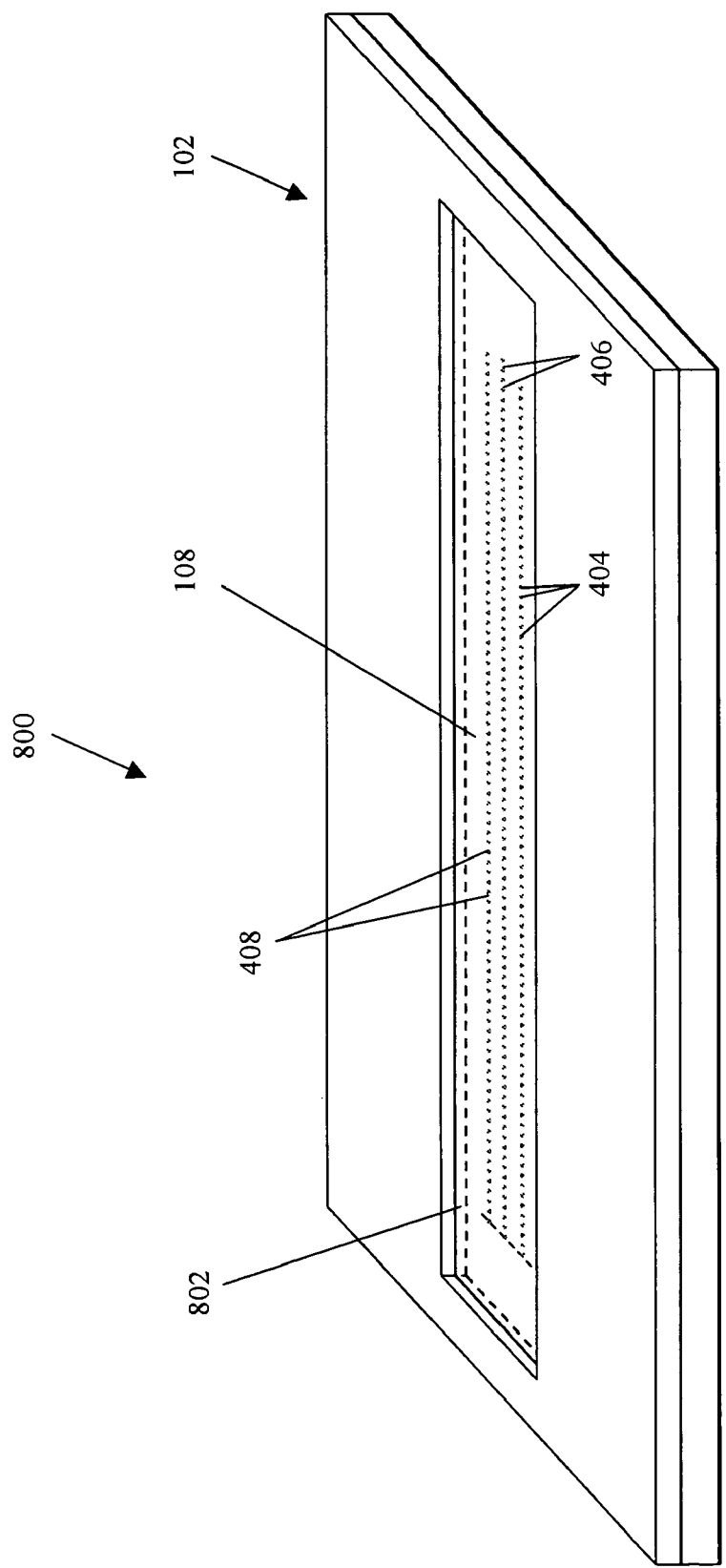
FIG. 8 illustrates a perspective view of a portion of the stretched elastic substrate assembly with ordered fragments cross-linked to temporary binding molecules and a solution for forming a transfer substrate filling the sample well.

FIG. 8 illustrates a perspective view of the central region of the stretched elastic substrate assembly 102. Elastic substrate assembly 102 is held in the stretched geometry by the apparatus of assembly 700 shown in FIG. 7B and FIG. 6. FIG. 8 is designed to show primarily the sample well 108 area and the surrounding region of stretched elastic substrate assembly 102. Not shown in FIG. 8 are the peripheral regions of assembly 700 that exist beyond the portion of the elastic substrate assembly 102 drawn in FIG. 8. In assembly 800, a solid transfer substrate 802 fills the sample well 108. The transfer substrate 802 was formed in-situ within the sample well 108, and sample fragments 404, 406, and 408 are typically completely or partially encased within the transfer substrate 802.

The transfer substrate 802 is made of water-soluble polymers, typically partially hydrolyzed polyvinyl alcohol such as Elvanol 51-05 sold by Dupont. Note that adjacent sample fragments 404, 406, and 408 are farther apart now than in FIG. 4, as the elastic substrate assembly 102 has been stretched, carrying the temporarily bound fragments with it.

Figure 9:
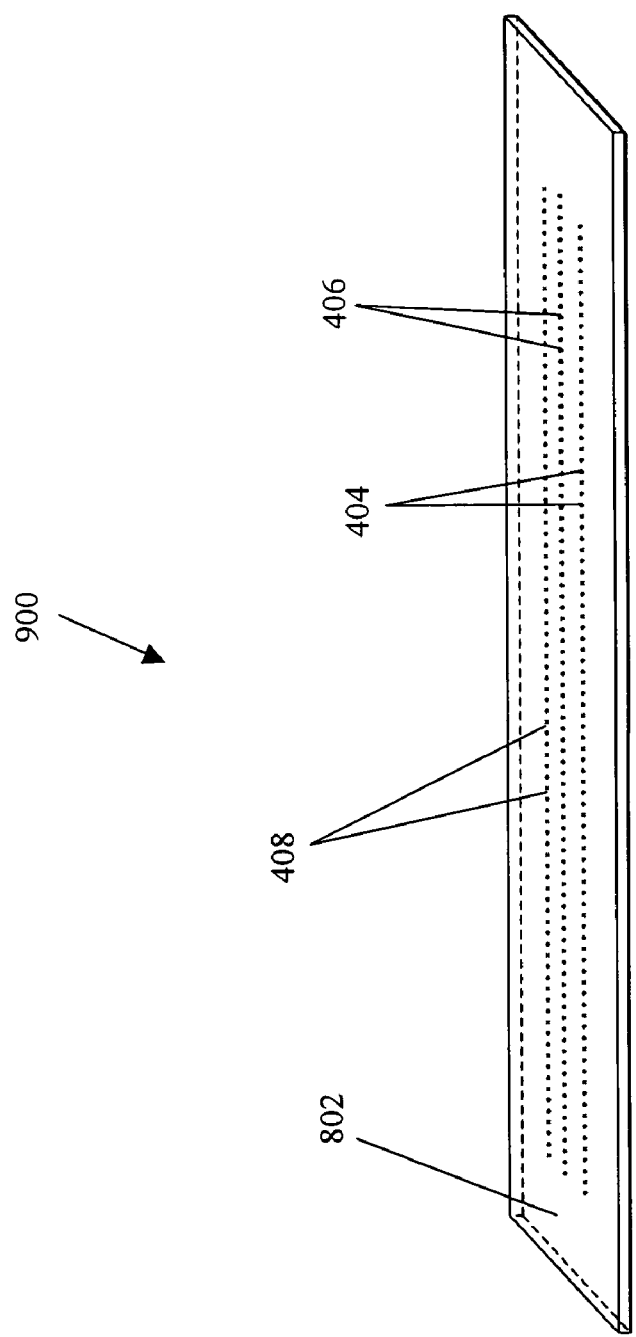
FIG. 9 illustrates a perspective view of the transfer substrate with the fragments embedded within it.

FIG. 9 illustrates assembly 900, which includes the transfer substrate 802 after it has been removed from the sample well 108 of the stretched elastic substrate assembly 102; both 108 and 102 are shown in FIG. 8. Partially or fully encased in the transfer substrate 802 are the sample fragments 404, 406, and 408. As described for FIG. 4, included with each fragment 404, 406, and 408 is one or more cross-linkers and one or more 1-octadecanethiol. The hydrophobic hydrocarbon tail of the 1-octadecanethiol mediated the temporary bonding of the fragments 404, 406, and 408 to the elastic substrate, and now that the temporary bond is broken, these tails are on the surface of transfer substrate 802. For clarity on the figure, only one or two fragments 404, 406, and 408 are labeled, but it is to be understood that each dot is another fragment 404, 406, or 408.

Figure 10:
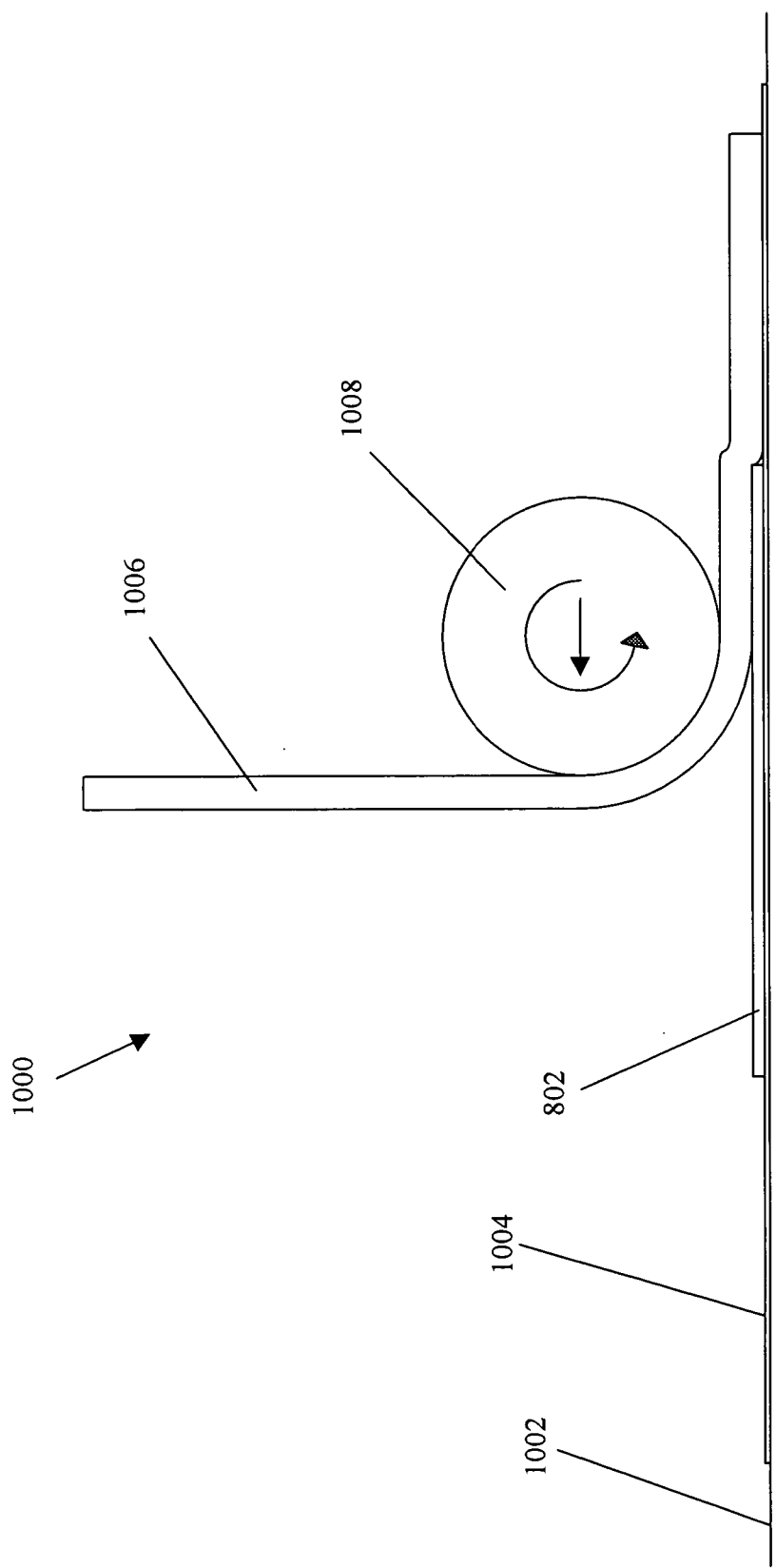
FIG. 10 illustrates a side view of a new elastic substrate being laminated over the transfer substrate.

FIG. 10 illustrates assembly 1000, wherein a relaxed new elastic substrate 1006 is being laminated to transfer substrate 802. The surface of transfer substrate 802 that includes the exposed hydrocarbon tails of the 1-octadecanethiol is up and is the surface against which new elastic substrate 1006 is laminated. The other surface of transfer substrate 802 is supported on release liner 1004, and release liner 1004 is supported on tabletop 1002. New elastic substrate 1006 is laminated over the transfer substrate 802 by the action of rolling pin 1008, which laminates by being rolled by hand in the direction and with the rotation as indicated by the two arrows shown on the rolling pin 1008. Release liner 1004 is a flexible material with a non-stick surface, such as waxed paper, Teflon film, or PET film of thickness roughly 1 mil-7 mil. New elastic substrate 1006 is made of silicone rubber with a durometer of less than roughly 50 A, and preferably in the approximate range of less than 5 A to 30 A, and ultimate elongation preferably greater than 400%, although materials with lessor ultimate elongation capabilities can be used. The length and width of new elastic substrate 1006 when relaxed is typically in the range of roughly 10 cm to 40 cm larger than the length and width of the transfer substrate 802. The thickness of new elastic substrate 1006 is typically less that 6 mm and preferably in the range of 0.5 mm to 3 mm. Rolling pin 1008 can be made of many rigid materials including rigid plastic, metal, or wood, and is typically longer than new elastic substrate 1006 is wide, and its diameter is usually in the range of roughly 1 cm to 10 cm.

All dimensions listed above are given to provide specificity to a typical layout. There is a great deal of allowable latitude in the dimension and none are critical.

Operation of Preferred Embodiment

Figure 11:
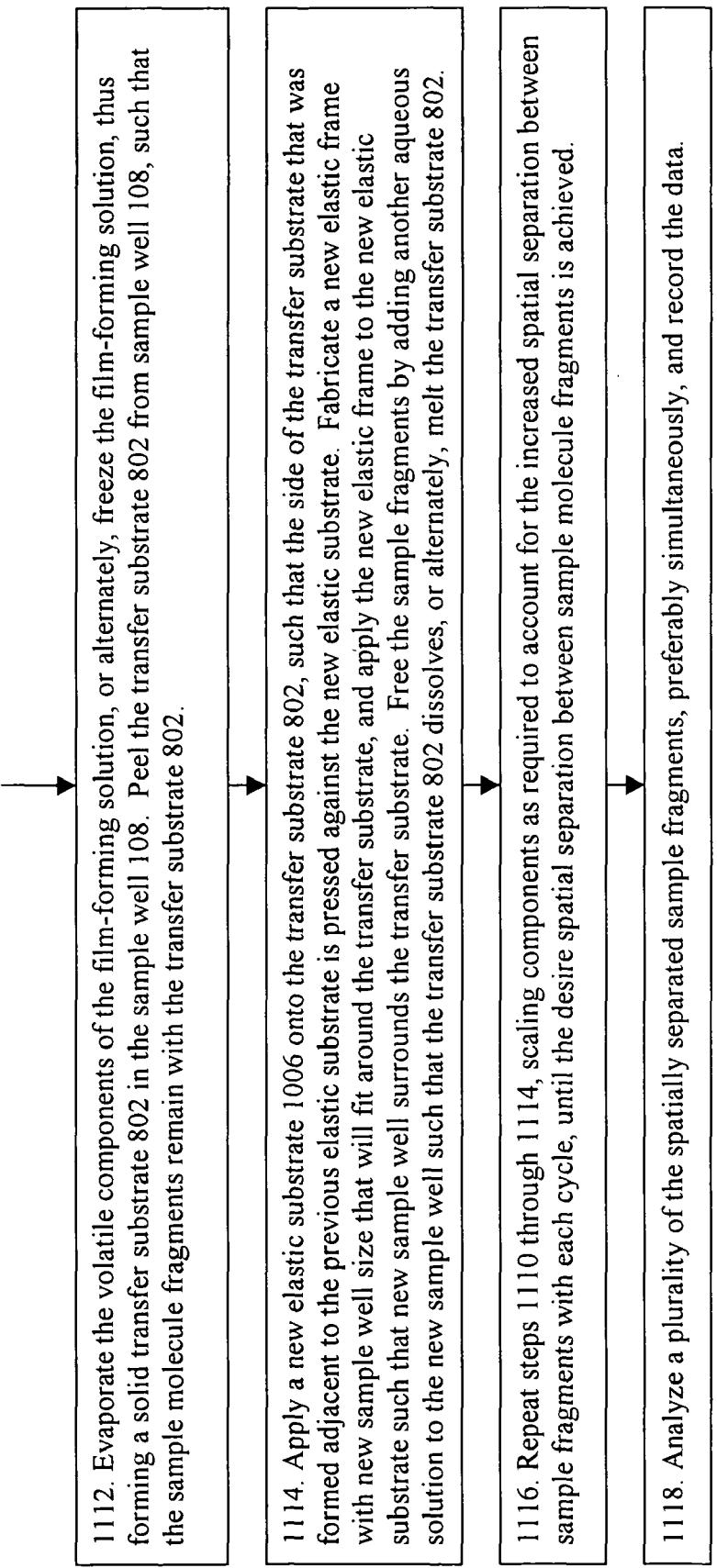
FIG. 11 illustrates a process flow for analyzing sample molecules.

Operation of the preferred embodiment follows the method presented in FIG. 11 and uses the assemblies and apparatuses illustrated in FIGS. 1-10. Note, in FIG. 11, the numbers within the sentences refer to components illustrated in FIGS. 1-10. The method begins in FIG. 11 box 1100 with the assembly of the elastic substrate assembly 102, illustrated in FIG. 1. This is simply done by cutting silicone rubber sheet to the desired dimensions for the elastic substrate 104 and the elastic frame 106. 104 and 106 need not be cut from stock of the same thickness. Scissors or razor blades are effective. Once cut, the parts are manually laminated together so that there are as few air bubble as possible between 104 and 106. Preferably, sample well 108 will be approximately centered in elastic frame 106 and over elastic substrate 104.

Either before or after assembly of elastic substrate assembly 102, the surface of elastic substrate 104 that shows through sample well 108 is impregnated with 1-octadecanethiol (ODT). This is done by applying a solution of roughly 30 mM ODT in ethanol for roughly one hour at room temperature. The solution should be covered to prevent evaporation of the ethanol. After soaking with the ODT solution, the area should be gently rinsed with pure ethanol and air or N2 dried. The ODT will diffuse into the silicone rubber, and when later covered with an aqueous solution, the polar thiol groups will preferentially stay at the interface between aqueous solution and silicone, and the hydrophobic hydrocarbon tails with preferentially remain in the hydrophobic silicone rubber polymer matrix. In the presence of a covering aqueous solution, ODT molecules cross-linked to sample fragments will function to temporarily bond the fragments to the silicone. These temporary bonds are not covalent, mediated instead by hydrophobic/hydrophilic surface-energy derived forces, and become particularly weak if the aqueous solution is replaced by a non-aqueous medium, such as a solid.

Next the line of anchor molecules 110 is deposited on elastic substrate 104. This can be accomplished by many different techniques, such as the preferred method described in U.S. patent application Ser. No. 11/827,588. Briefly, the process entails forming an "ink" of streptavidin conjugated with a thiol-reactive cross-linking agent, such as a cross-linking agent having a terminal maleimide group, and printing this ink onto the elastic substrate 104 using a silicone rubber stamp having a line pattern or a linear pattern of dots. The thiol-reactive group attached to the straptavidin bonds to the terminal thiol of an ODT molecule previously impregnated into the elastic substrate 104, thus forming the line of anchor molecules 110.

Next, per box 1102 of FIG. 11, the sample dsDNA is isolated and prepared by conjugating one or more biotin molecules to, preferably, one end of each sample molecule. Several published protocols and commercial reaction kits and reagents are available for forming biotin end-labeled dsDNA, and any of these methods can be used. Typically these processes proceed by adding a reactive amine, thiol, or sulfhydryl group to the end of the sample molecules and then cross-linking these to biotin that has been functionalized with reactive maleimide, iodoacetamide, or succinimide groups. Alternately, the procedure directly labels with biotin using biotin-14-dATP or another biotin-nucleotide conjugate. The final product is biotin end-labeled dsDNA in an aqueous biotin-straptavidin reaction solution, such as water or phosphate buffered saline (PBS).

Referring to FIG. 11 box 1104, once prepared, the solution containing the biotin end-labeled sample molecules is added to sample well 108, and sufficient time is provided to allow biotin end-labeled sample molecules to bind at a desirable density along the line of anchor molecules 110. Typically this is done at room temperature or below.

From FIG. 11 box 1106, following anchoring of the sample molecules, 204, 206, and 208 in FIG. 2, the elastic substrate assembly 102 is tilted up so that the aqueous solution in sample well 108 drains out and the sample molecules are extended over the surface of the elastic substrate 104. The final configuration is illustrated in FIG. 3 with extended sample molecules 304, 306, and 308. The elastic substrate assembly 102 is then thoroughly dried, preferably with flowing dry air or nitrogen at room temperature. Once fully dry, the extended sample molecules become non-specifically bound to the surface of elastic substrate 104 at multiple locations along their lengths.

Note that for clarity of the illustrations, only three sample molecules, 204, 206, and 208, and subsequently 304, 306, and 308, and 404, 406, and 408 are shown in FIG. 2-4 and others. In practice, one or more, and beneficially many more, sample molecules can be processed on a single elastic substrate assembly.

Referring to FIG. 11 box 1108. An aqueous solution is added to sample well 108, and the extended sample molecules, 304, 306, and 308 in FIG. 3, are fragmented, and the fragments are cross-linked to ODT molecules residing at the surface of elastic substrate 104. This generates sample fragments, illustrated as 404, 406, and 408 in FIG. 4, that are temporarily bound to the elastic substrate 104. The fragmenting and cross-linking can be accomplished by many different methods. Methods available for labeling DNA, such as random primer extension, psoralen photo-cross-linking, and nick translation, can be employed to cleave one or both strands of the sample DNA and add reactive amine groups along the sample DNA molecules. Cross-linking agents, such as sulfo-SMCC (4-(N-Maleimidomethyl)cyclohexane-1-carboxylic acid 3-sulfo-N-hydroxysuccinimide ester sodium salt from Sigma-aldrich and sulfosuccinimidyl 4-[N-maleimidomethyl]cyclohexane-1-carboxylate from Pierce, Rockford, Ill.), can then be used to cross-link these amine groups to the thiol groups of the ODT. For the preferred embodiment, the nick translation technique is employed. Standard nick translation protocols and kits are available (such as the Nick Translation System, catalog number 18160-010 from Invitrogen) and are modified to incorporate reactive amine conjugated nucleotides and chain terminators such as dideoxy-nucleotides to limit the extent of the nick translation products. For example, a nick translation protocol can be applied using a commercial or standard lab protocol (Current Protocols in Molecular Biology, etc.) nick translation reaction buffer, DNA Polymerase I, DNase I, unmodified dTTP, amine-modified dATP, dCTP, and dGTP (such as N6-(6-amino)hexyl-dATP, Y-[(6-aminohexyl)-imido]-dCTP, and Y-[(6-aminohexyl)-imido]-dGTP, catalog numbers NU-835L, NU-846L, and NU-849L, respectively, from Jena Bioscience) and a complete set of ddNTPs, catalog number NU-1019L from Jena Bioscience. These modified and unmodified nucleotides are mixed in a predetermined ratio designed to typically yield at least one amine-modified nucleotide per nick translation and to terminate on a dideoxy-nucleotide before extending more than roughly 6 to 20 bases. The reaction is stopped by standard means, including adding EDTA or a protein kinase, and repeated cycles of buffer exchange. The cross-linking reaction is also initiated by a buffer exchange, adding the cross-linking reagent in suitable buffer, and terminated by repeated buffer exchanges of water, PBS, or TE buffer. Note, sample well 108 is typically not drained during the buffer exchanges, rather the new buffer is added to excess, and either the buffer is allowed to overflow out of the sample well 108, or two pipettes are employed, one to add the exchange buffer and one to extract excess buffer from the sample well 108.

To achieve a higher yield of shorter fragments, it can be beneficial to perform multiple cycles of back-to-back fragmentation and cross-linking, rather than one fragmentation step followed by a single cross-linking step. This is because smaller fragments are more frequently lost into the surrounding solution, unless already cross-linked to ODT. The predetermined optimum length of the fragments is determined by the specifics of the processing to be done after the spatial separation steps are completed, as outlined in box 1118 of FIG. 11.

Now the elastic substrate assembly 102 is stretched in one or more directions, as outlined in FIG. 11 box 1110. The amount of stretching depends on the initial spatial separation of the fragments and the desired final spatial separation and on the physical properties and capabilities of the silicone elastomer. The rate of stretching is limited to allow the hydrophobic tail of the fragment-cross-linker-ODT conjugate to maintain an approximately equilibrium position near the surface of the elastic substrate 104, determined by the balance between hydrophobic and hydrophilic forces and not by the dynamics of the stretching. It is also desirable to limit the effect of shear flows on the DNA. To maintain the hydrophobic/hydrophilic forces, aqueous solution should be added to sample well 108 to maintain coverage of the elastic substrate 104 as the elastic substrate assembly 102 is stretched. Solution can be added manually from a pipette. Once stretched, the elastic substrate assembly 102 is held in this stretched conformation.

The stretching apparatus and process follow FIGS. 5-7. Referring to FIG. 5, elastic substrate assembly 102 is placed on structural support element 502, and rod 504 is placed onto one predetermined end of substrate assembly 102. Rod 504 is rolled with the hands toward the center of elastic substrate assembly 102 while holding the elastic substrate assembly 102 to the rod 504 with one's fingers. Rod 504 is rolled until elastic substrate assembly 102 is wound around the rod 504 at least one and a half revolutions. Dowel pins 506 are then inserted through both through-holes in rod 504 and further inserted into both holes 720, so that rod 504 and the elastic substrate assembly 102 are prevented from moving in the plane of structural support element 502. Rod 508 is now placed on the oppose end of the elastic substrate assembly 102 and rolled by hand toward the rod 504. Using one's fingers to hold the elastic substrate assembly 102 to rod 508 as it is rolled, the elastic substrate assembly 102 is wound at least one and a half times around the rod 508. The elastic substrate assembly 102 is now stretched by pulling or urging with the hands on rod 508 in the direction of holes 730. As the elastic substrate assembly 102 is stretched, additional aqueous solution may be added to the sample well 108 by means of a pipette, for example, so that all temporarily bound fragments remain covered with solution, as illustrated by volume of solution 402. The through-holes in rod 508 are aligned over holes 730 and dowel pins 602 are inserted through these through-holes and into holes 730. Dowel pins 506 and 602 hold the elastic substrate assembly 102 in a first stretched conformation, as illustrated in FIGS. 6 and 7A.

Stretching of the elastic substrate assembly 102 in a second, approximately perpendicular, direction, is accomplished by placing one of rods 702 and 704 on each of the two exposed ends of elastic substrate assembly 102, and rolling the rods toward each other while holding the elastic substrate assembly 102 against the rods. This is done manually, by hand with manual forcing or urging of the substrate. Each rod 702 and 704 is rolled until at least one and a half turns of elastic substrate assembly 102 are wound around each rod. Rods 702 and 704 are then pulled away from each other, by hand, until the two through-holes 712 in each of rods 702 and 704 are aligned over holes 710. As the elastic substrate assembly 102 is stretched, additional aqueous solution may be added into sample well 108 to keep all the temporarily bound fragments, 402, 404, and 406, covered. The pairs of dowel pins 706 and 708 are then inserted through the through-holes 712 in the rods 702 and 704 and into holes 710. The elastic substrate assembly 102 is now held in it final stretched conformation, as illustrated in FIG. 7B.

The transfer substrate 802 is now formed within sample well 108, as illustrated in FIG. 8 and outlined in box 1112 of FIG. 11. This is accomplished by exchanging aqueous solution 402 with an aqueous solution that includes a water-soluble film-forming material, box 1111 of FIG. 11. In the preferred embodiment, a solution of approximately 1 to 20 wt % polyvinyl alcohol (PVOH) dissolved in water (the PVOH is preferably Elvanol 51-05 or 52-22) is added by pipette to sample well 108 as another pipette is used to extract the existing solution 402. Once the PVOH solution is in the sample well 108, the water is evaporated leaving the solid PVOH transfer substrate 802. The solid transfer substrate 802 is water-soluble. Encased in the transfer substrate 802 are the hydrophilic portions of the temporarily bound sample fragments 404, 406, and 408. The hydrophobic portions of the temporarily bound sample fragments 404, 406, and 408, primarily the hydrocarbon tails of the cross-linked ODT, mostly still reside in the silicone elastic substrate 104.

Once the transfer substrate 802 is formed, it can be peeled, by hand, from the sample well 108. The sample fragments 404, 406, and 408, including the cross-linker molecules and cross-linked ODT, remain with the transfer substrate 802, as illustrated in FIG. 9. The hydrocarbon tails of the cross-linked ODT sit on the top surface of the transfer substrate 802.

A new elastic substrate 1006, as illustrated in FIG. 10 and outlined in box 1114 of FIG. 11, is now applied over the top surface of transfer substrate 802. As indicated in FIG. 10, this is accomplished by laminating the new elastic substrate 1006 over the top surface of transfer substrate 802. The side into which the fragments 404, 406, and 408 are encased is the top surface of transfer substrate 802. The lamination process can be done by hand by placing rolling pin 1008 on one end of new elastic substrate 1006 and rolling the rolling pin 1008 over the new elastic substrate 1006.

Once the lamination is complete, the stack of new elastic substrate 1006, transfer substrate 802, and release film 1004 is lifted from tabletop 1002 and inverted onto a work surface. Release film 1004 is then peeled from new elastic substrate 1006 and transfer substrate 802. A new elastic frame is cut from silicone rubber, with properties typically similar to those of new elastic substrate 1006, and placed onto the new elastic substrate 1006 such that the transfer substrate 802 fits within the new sample well of the new elastic frame. The new elastic frame is pressed firmly onto the new elastic substrate 1006 using ones gloved fingers and any air bubbles between these parts are worked out. An aqueous solution, pure water or a buffer such as PBS or TE (TRIS-EDTA buffer, pH ~8.0, from Sigma-Aldrich), is then added to the new sample well so that the transfer substrate 802 is dissolved, leaving the sample fragments 404, 406, and 408 temporarily bound to the new elastic substrate 1006.

This new assembly is comprised of new elastic substrate 1006, the new elastic frame, the aqueous solution filling the new sample well, and the spatially separated fragments 404, 406, and 408. It appears similar to the assembly 400 illustrated in FIG. 4, except that, due to the previous substrate having been stretched, the lateral dimensions are larger and the fragments 404, 406, and 408 are farther apart. Also, there is no line of anchor molecules 110 in the new assembly.

Referring to box 1116 of FIG. 11, this new assembly can be processed in the same way as described above for the elastic substrate assembly 102, leading to further spatial separation between fragments 404, 406, and 408. Of course, certain components must be scaled by predetermined amounts, approximately in proportion to the stretching of the previous elastic substrate assembly, and in particular the distances between sets of holes 720 and 730 and between holes 710 are increased and the lengths of rods 504, 508, 702, and 704 are increased. Hence a cyclical process of substrate stretching followed by transferring of the sample fragments to a new elastic substrate assembly can be repeated until the desired total spatial separation between fragments 404, 406, and 408 is achieved. For example, if in each cycle the stretching process increases spatial separation between adjacent fragments by 4× (400%), then a total increase in spatial separation of 256× can be accomplished in just four stretching cycles. The amount of stretching per cycle and the number of cycles can be varied to achieve any degree of increase in spatial separation between fragments. Typically, the desired total spatial separation between fragments is that which allows subsequent processing to be conducted simultaneously on adjacent fragments without resulting in interference in processing of the fragments or reading out and recording data generated by action of the process on the fragments.

Note that the process parameters and material properties of any of the components, including the elastic parts and the aqueous solutions, can be varied as is beneficial with each new cycle, such as the durometer of the elastic parts or the depth of the sample well. In particular, to better support subsequent processing of the sample fragments, the final elastic substrate can be made from a high durometer or hard silicone or a composite assembly composed of a thin layer of silicone deposited over a flat and rigid substrate (such as polished plate glass) or other material, and the elastic frame can be left off or removed. A flat and rigid final substrate is beneficial when the subsequent processing includes viewing the sample fragments and substrate with a microscope.

Key to this cyclic process are: 1) the temporary bonding, and re-bonding, of sample fragments to successive generations of elastic substrates, and 2) the formation and dissolution of transfer substrates that allow sample fragments, including the added cross-linkers and cross-linked temporary binding molecules (ODT in the preferred embodiment), to be moved from a stretched elastic substrate to a relaxed elastic substrate while maintaining the relative positions of the fragments. The methods, assemblies, and apparatuses presented herein uniquely provide for these key attributes.

Referring to box 1118 of FIG. 11, once the sample fragments have been spatially separated by the desire amount, they are subsequently processed, preferably simultaneously. Typically, the final result of the processing will be the determination of the base sequence of all or part of the sample molecules, 204, 206, and 208 of FIG. 2, but other beneficial processes can be conducted. The significant advantage of the method detailed above, is that the sample molecules, 204, 206, and 208 of FIG. 2, are reduced to more easily managed and processed fragments, 404, 406, and 408 of FIG. 4, and the order of the fragments, 404, 406, and 408, remains the same as in the original sample molecules, 204, 206, and 208. Hence, any data recovered from individual fragments during subsequent processing can be easily placed in the correct order and approximate location along the original, whole, sample molecules. For the preferred embodiment, subsequent processing would follow the method of labeled-probe-assemblies for determining the base sequence of all or part of the sample molecules, as detailed in U.S. patent application Ser. No. 11/827,588.

Alternate Materials and Methods for Fabricating and Operating the Preferred Embodiment Many alternate materials and variations in the method of the preferred embodiment are available. The following details some of these alternates and variations.

Alternate Materials:

Elastic substrate 104, elastic frame 106, new elastic substrate 1006, and new elastic frame Any elastomeric material, particularly hydrophobic elastomeric materials, and preferably those with ultimate elongation of at least 400%

Silicone rubber, Fluorosilicone rubber, Polyurethane rubber, Sorbothane, EPDM rubber, Neoprene rubber, latex, natural rubber, nitrile rubber, butyl rubber, thermoplastic elastomers Cast silicone rubber, such as Sylgard 186 and Sylgard 184, where the material is either first cast into sheets and then cut, or cast into the final shape of elastic substrate assembly 102

Silicone gel, other hydrophobic gels and putties, silicone putty, silicone dilatent compound (Dow Corning, Midland, Mich.)

Plastically deformable materials, including low-temperature blow moldable plastics, low Tg (glass transition temperature) polymers, ethylene-vinyl acetate with ethylene acetate plasticizer, Parafilm M (American National Can, Menasha, Wis., USA), Teflon skived film, polyethylene film, polypropylene film, stretch film for food processing and wrapping pallets, Duco Cement (Ted Pella Inc., Redding, Calif.), modified nitrocellulose solutions, and B' loonies (Ja-Ru Inc., Jacksonville, Fla.). With these materials, the "elastic" substrate assembly is plastically deformed during the stretching process of box 1110 of FIG. 11. In an alternate process, a plastically deformable material, such as listed here, is used as the elastic substrate. The sample molecule can be processed into fragments on this substrate, or fragments can be generated on another substrate and transferred to the plastically deformable substrate. This transfer can be done by direct contact-transfer from a silicone substrate, or using any of the other transfer substrate means described. Once the fragments are on the plastically deformable substrate, it can be stretched along one direction until if contracts laterally to form a fiber, with the fragments separated along a length of the fiber. No additional stretching cycles may be needed. Further processing of the fiber substrate can follow the method detailed below in the section titled "Further Variations on the Nano-Patterned Substrate" for the fully extended fiber-like nano-patterned substrate.

Low melting temperature hydrophobic materials, waxes, paraffin wax, synthetic waxes, Tissue-Tek VIP 4005 (Sakura Finetek USA Inc, Torrance, Calif., USA), in which case the "elastic" substrate assembly is heated until soft and plastically deformed and flowed during the stretching process of box 1110 of FIG. 11.

The final new elastic substrate can be a rigid substrate, optimized for subsequent processing and data collection from the spatially separated fragments. Where 18:1-12:0 Biotin PE or another biotin terminal temporary binding molecule is employed, the final new elastic substrate can be coated with streptavidin, avidin, or other biotin binding molecule to more permanently bond the fragments to the final substrate. The final new elastic substrate can be a layered structure having a rigid support layer, such as a glass plate, covered with a thin silicone layer, such as a spin-coating formed layer of Sylgard 184 or other pourable and castable PDMS. A primer may be applied to the rigid substrate prior to the PDMS, if enhanced adhesion between the layers is desired.

Molecules for mediating the temporary binding of sample fragments to elastic substrates Ambipolar molecules with reactive, cross-linkable, polar groups 1-Octadecanethiol (ODT), Octadecylamine, 1-Octadecanol, Octadecanoic acid, 1-Eicosene, 1-Docosene, Eicosanoic acid, 1-Eicosanol, 1-Docosanol Linear hydrocarbons of length between roughly 8 to 100 carbons with a terminal thiol group Branched or, preferably, linear hydrocarbons of length between roughly 8 to 100 carbons with a terminal amine, carboxyl, vinyl, carbonyl, hydroxyl, sulfhydryl, thiol, DNA, RNA, PNA, succinimide, maleimide, psoralen, biotin, streptavidin, or other reactive group or DNA intercalating group. Suitable branched or, preferably, linear hydrocarbons include polyethylene, polypropylene, polystyrene, and linear chains of cyclic hydrocarbons. In addition, branched or, preferably, linear fluorocarbons, chlorocarbons, and fluoro-chlorocarbons can be substituted for the hydrocarbons.

Triglycerides, phopholipids, phosphatidylethanolamine (PE), N-MCC-PE (Avanti Polar Lipids, cat. no. 780200 or 780201), N-Succinyl-PE (Avanti Polar Lipids, cat. No. 870225 or 870222), 18:1-12:0 Biotin PE (1-olcoyl-2-(12-biotinyl(aminododecanoyl))-sn-glycero-3-phosphoethanolamine) (Avanti Polar Lipids, cat no 860562), and other hydrocarbons and lipids with one or more polar end-groups and one or more biotin end-groups.

Linear or branched PDMS having less than roughly 100 siloxane groups, with one or more reactive terminal groups to facilitate cross-linking to, such as a silicone oil with an un-reacted vinyl end-group.

Mixtures of these, such as a mixture of ODT and 1-Eicosene.

No added molecules. Many biomolecules, including nucleic acids and proteins have hydrophobic regions and hydrophilic regions and other moieties that facilitate substrate binding. Temporary binding of DNA, RNA, and proteins to solid substrates can be accomplished by thorough drying of the substrate in contact with the biomolecule.

Cross-linkers for cross-linking sample fragments to the molecules for mediating the temporary binding of sample fragments to elastic substrates Sulfo-SMCC (Pierce), SMCC (Pierce), SPB (Succinimidyl-(4-psoralen-8-yloxy)butyrate, from Pierce, for photo-cross-linking to DNA and succinimide cross-linking to 1-octadecylamine impregnated into the elastic substrate), streptavidin as a cross-linker with biotin-conjugated nucleotides used to label the sample fragments and biotin conjugated to long linear hydrocarbons used as the temporary binding molecules impregnated into the elastic substrate, EDC (Pierce) for cross-linking from terminal 5'-P of nucleic acids to reactive amine containing temporary binding molecules such as Octadecylamine, any suitable homo- or hetero-bifunctional cross-linking agent (see for example the many available cross-linking agents from Pierce and Sigma-Aldrich) The choice of cross-linker depends on the identity of the temporary binding molecule impregnated into the elastic substrate and the identity of the reactive groups added to the sample fragments.

No added cross-linker. Nucleic acids and proteins can be cross-linked to other molecules without added cross-linkers by using heat, light, UV-light, and/or thorough drying.

Line of anchor molecules 110, in FIG. 1

Streptavidin-maleimide conjugate, avidin-maleimide conjugate, biotin-maleimide conjugate (Invitrogen), Octadecylamine and/or longer chain amine-terminal hydrocarbons, or other linkers designed for attaching nucleic acids to solid supports No line of anchor molecules. The line of anchor molecules 110 is not needed for certain sample molecule extending processes, such as molecular combing or rapid draining of the sample well. Note, for sample molecule extending processes that do not require a line of anchor molecules 110, one can be used to better specify where on the elastic substrate the sample molecules will be located.

End-label of sample molecules amine-conjugated nucleotide, biotin-conjugated nucleotide, modify 5'P end with a carbodiimide, such as EDC (Pierce cat no 22980), cross-linker chemistry, other reactive groups for cross-linking to biotin or directly to the line of anchor molecules 110 on elastic substrate 104

No end-label. End labeling is not need for anchor molecules that can directly bind to end-groups of sample molecules, or for sample molecule extending processes that do not require a line of anchor molecules.

Sample molecules dsDNA, ssDNA, RNA, mRNA, cDNA, miRNA, snRNA, siRNA, nucleic acids, PNA (protein nucleic acid polymer), And any of these can be of high molecular weight, but they are not required to be.

Proteins, Denatured proteins

Aqueous solutions

Any aqueous solution compatible with the sample molecules, and for certain steps, compatible with streptavidin to biotin binding, and sulfo-SMCC cross-linking to amine, and sulfo-SMCC cross-linking to thiol groups (i.e. solutions with the correct ranges of pH and salt).

Common DNA or RNA buffers such as water, de-ionized water, DEPC-treated water (Ambion, cat. No. 4387937), TE, PBS, SSC, MES (Pierce cat no 28390), Good buffers, etc. Mixtures of these buffers. Mixtures of these buffers and the water-soluble solid transfer substrate forming materials listed below.

Water-soluble solid transfer substrate forming materials (film-forming materials to form transfer substrate 802 of FIG. 9)

PVOH, particularly partially hydrolyzed varieties such as Elvanol 51-05 and 52-22 from Dupont, alternately or in combination, fully hydrolyzed PVOH grades DNA, Herring sperm DNA, Salmon sperm DNA, Lambda DNA, other natural or synthetic DNA molecules, poly-N DNA, RNA, poly-N RNA, poly-N PNA (peptide or protein nucleic acid), PNA PEG (polyethylene glycol), PEG of sufficient polymer length so as to be a solid at room temperature, for example, PEG having a molecular weight greater than approximately 1000 Da. Particularly PEG grades purified for molecular biology use (for example PEG 6000, Cat. No. 81253-1KG, Sigma-Aldrich)

PEO (poly(ethyleneoxide)) of sufficient molecule weight to be a solid at room temperature, for example Polyox WSR-301 from Amerchol Corp, Edison, N.J., USA PVP (Polyvinylpyrrolidone), for example Sigma-Aldrich cat. no. P5288-1KG Glycerol PEI (Poly(ethyleneimine)), for example Sigma-Aldrich cat. no. P3141-1L Water soluble sugars and salts Mixtures of the above materials Alternate transfer substrate materials and solvents Non-aqueous solvents can be used in film forming solutions and to dissolve transfer substrates, including non-aqueous polar and non-polar solvents, such as acetone, methyl ethyl ketone (MEK), other ketones, isopropyl alcohol, other alcohols, ethyl lactate, other non-polar solvents, and mixtures of these.

Film forming solutes compatible with non-aqueous solvents include, novalak resins, such as used in commercially available photo resists, photo resists, polystyrene, polyvinyl acetate, ethyl acetate, Protek coating agents, waxes, and mixtures of these.

Alternate Methods:

Fabrication of elastic substrate assembly

Cut from sheet silicone rubber stock

Cast curable silicone rubber in an appropriately shaped mold, (for example Sylgard 186 or Sylgard 184)

The elastic frame 106 may be bonded to the elastic substrate 104, and similarly the new elastic frame may be bonded to the new elastic substrate 1006, using a suitable adhesive, such as a thin layer of RTV silicone rubber, Sylgard 186, Sylgard 184, silicone putty, and/or silicone dilatant compound.

Extension of sample molecules over elastic substrate (box 1106 of FIG. 11)

DNA combing, molecular combing, rapid fluid flow and draining of sample well, electric field mediated molecular alignment followed by rapid draining of the sample well or molecular combing, or other techniques detailed in the open literature. Some of these methods may alleviate the need for the line of anchor molecules 110.

Alignment of the sample molecules by means of an electric field, followed by passage of liquid Mercury over the surface of the elastic substrate. This is accomplished by placing a rectangular glass plate over the elastic frame 106, see FIG. 1, after completing the steps of FIG. 11 through box 1104. The glass plate covers the whole of the sample well 108 except along two opposing ends, a first open end and a second open end, where the sample well 108 is open (not covered) at both the first and second open ends. The edges of the glass plate along the two open ends are aligned approximately parallel to the line of anchor molecules 110, see FIG. 1, and the first open end is nearest to the line of anchor molecules 110. The sample molecules 204, 206, and 208, see FIG. 2, will be extended along the direction between these two open ends, approximately perpendicular to the edges of the glass plate at the open ends. The width of the glass plate along this direction is preferentially longer than the longest sample molecule to be extended and covers the line of anchor molecules 110. Sample molecules are attached by their ends to the line of anchor molecules 110, and the sample well 108 is filled with an aqueous solution to overflowing. A first conducting electrode is placed in the overflowing aqueous solution near the second open end of the sample well, that is farthest from the anchor line 110, and a conducting Mercury electrode is applied along the first open end of the sample well. A DC power supply is connected between the Mercury electrode and the first electrode, and a voltage is maintained between the two electrodes such that the sample molecules are aligned between the two electrodes and preferentially forced away from the Mercury electrode. Additional Mercury is added to the Mercury electrode so that Mercury flows into the first open end, under the glass plate, and through the sample well. The elastic substrate assembly 102 may be tilted to assist in the flow of the Mercury across the sample well 108 from the first open end toward the second open end. Preferably, the leading edge of the flowing Mercury electrode is maintained approximately parallel to the line of anchor molecules 110. Once the sample well 108 is filled with Mercury, the power supply is switched off and the elastic substrate assembly 102 is tilted to drain out all of the Mercury from the sample well 108. In this way, the sample molecules 204, 206, and 208 are aligned by the applied electric field generated between the first electrode and the Mercury electrode, and the sample molecules 204, 206, and 208 are forced against the elastic substrate 104 by the Mercury as it moves across the sample well 108. Upon removal of the Mercury and glass plate, the configuration of FIG. 3 is achieved with extended sample molecules 304, 306, and 308 being the extended conformations of sample molecules 204, 206, and 208 of FIG. 2.

In addition to Mercury, other electrically conducting liquids with minimal solubility in water can be used as the flowing electrode. Other suitable flowing electrode materials include Gallium, low melting temperature solders, and other low-melting-temperature electrically-conducting eutectic mixtures.

In an alternate arrangement, within a suitable vessel, the aqueous solution is floated on top of a pool of liquid Mercury, which forms the Mercury electrode. An electrically conducting wire, screen, or mesh is held within the aqueous solution, and the power supply is connected between this wire and the Mercury electrode. The power supply is energized to maintain a voltage between the Mercury electrode and the wire such that the sample molecules are repelled from the Mercury electrode. The voltage is limited such that sample molecules are not generally broken by the action of the voltage on the sample molecules and aqueous solution. The elastic substrate assembly 102 is oriented roughly vertically (in other words, a line normal to the surface of the elastic substrate 104 is roughly horizontal) and lowered through the aqueous solution and into the Mercury electrode. Once the elastic substrate assembly 102 has been lowered sufficiently into the pool of Mercury to extend the sample molecules along the surface of the elastic substrate 104, the elastic substrate assembly 102 is removed from the Mercury.

Generation of sample fragments (for example, fragments 404, 406, and 408 of FIG. 4) with cross-linkable groups, box 1108 of FIG. 11

As defined in this document, sample fragments refers to any of the following: pieces of the original sample molecules, pieces of amplification products of the original sample molecules or portions thereof, short length amplification products generated on portions of the sample molecules, pieces of nucleic acid strands which are complementary to at least a portion of the original sample molecules, and oligomers that are either complementary to or have the same sequence as a portion of the original sample molecules.

Nick translation with insertion of amine, thiol, or sulfhydryl labeled nucleotides and limiting the length of the translations by including a fraction of chain terminating nucleotides, such as dideoxynucleotides (ddNTPs), or amine or thiol modified chain terminating nucleotides.

Nick translation with a mixture of un-modified dNTPs and ddNTPs, and subsequent modification with a carbodiimide chemistry (such as EDC (Pierce cat no 22980)) and cross-linking to amine containing temporary binding molecules, such as PE or 1-Octadecylamine.

Physical breaking of the sample molecules as the elastic substrate assembly is stretched and the ultimate elongation of the sample molecules is exceeded. This can be done with substrate covered with a liquid or dry.

Focused electron-beam cutting, focused ion-beam (FIB) cutting, or UV-light inducted cleaving.

Photo-cross-linking of amine-modified-psoralen, or other amine containing photo-cross-linking compounds, to the sample molecules followed by cross-linking between the reactive amine of the amine-modified-psoralen to the thiol of the ODT with sulfo-SMCC, or other cross-linker, and finally, nicking or cleaving with DNase I in a Manganese or Magnesium salt containing reaction buffer.

Cross-linking of cross-linking compounds, including photo-cross-linking compounds (see for example Pierce), to sample molecule, followed by cross-linking of cross-linking compounds to temporary binding molecules, optionally followed by nicking or cutting, and optionally followed by single strand digestion. For example, single strand digestion with Exonuclease III from *E. coli*, T7 Exo, or Lambda Exo (New England Biolabs, Beverly, Mass.). Alternately, changing the order in with cross-linking compounds are applied and cross-linked.

Impregnating the first elastic substrate with a temporary binding molecule that is also a cross-linking compound, extending the sample molecules over the substrate, and cross-linking the sample molecules directly to the temporary binding molecules. The dividing the sample molecule into fragments and optionally forming single strands.

Denature sample molecules with heat and/or alkaline (potassium hydroxide (KOH) or sodium hydroxide (NaOH) solution, etc.) and/or other means, and fix to elastic substrate 104 by rapid and complete drying or rapid drying followed by methanol:acetic acid fixation or other fixation process, per standard protocols. The sample molecules may be subjected to one or more cycles of denaturing, fixing, and amplification prior to the fragmentation process. In one case, the fragmentation process proceeds by hybridizing amine-terminal (at and/or near either the 3'- or 5'-end, but preferably not both) random oligomers of the desired length to the sample molecules. Alternately, use thiol or sulfhydryl terminal oligomers.

Or, following denaturing and fixing of the sample molecules, use a random primer process with added nucleotides and modified nucleotides as detailed above for the preferred embodiment nick translation process.

Alternately, following denaturing and fixing of the sample molecules, pairs of random oligomers of predetermined length are ligated together along the sample molecules and then cross-linked to the ODT in the elastic substrate. The random oligomers are provided as two types, those with one dideoxy 3'-end and one 5'-P end, and those with a 3'-OH end and a 5'-OH end, and either the first type is labeled with a reactive amine at and/or near its dideoxy 3'-end or the second type is labeled with a reactive amine at and/or near is 5'-OH end. Pairs of random oligomers will only ligate 5'-P to 3'-OH, and hence trimers and longer sections cannot be formed.

Alternate Apparatuses for Stretching of Elastic Substrate Assemblies

A simple and primarily manual means for stretching and holding elastic substrate assemblies is detailed herein. A more automated apparatus is detailed in U.S. patent application Ser. No. 11/827,588 (previously cited), and many other variations can be readily envisioned. The method and apparatus for stretching and holding the elastic substrate assembly are not critical to the success of the overall spatial separation process.

Stretching can be done while fragments are covered with a liquid or dry, depending on the specific process. This is generally true for any of the spatial separation methods described herein.

Formation and dissolution of the transfer substrate and alternate transfer substrates and methods Film forming solution can be a solution, suspension, or combination of the two, and dissolution of solid transfer substrate can be by either dissolving back into a solution, re-suspending as a suspension, or etching away by physical and/or chemical attack.

Where the film-forming solution is a mixture of water-soluble solids in water or suspended solids in water, the formation method is to evaporate the volatile components, primarily water, from the film-forming solution, and the dissolution method is to add water or aqueous buffer, such as TE buffer, SSC buffer, or PBS.

To increase the rate of evaporation, and hence minimize the time required to form the transfer substrate, the film-forming solution can be heated, and/or blow dry air or nitrogen (N2) over the film-forming solution, and/or the assembly 700 can be placed into a vacuum drier and vacuum dried, and/or the film-forming solution can be freeze-dried in a freeze-drier.

Alternately, the formation process can be to freeze the transfer substrate forming solution, and the dissolution process replaced by the melting of the transfer substrate. In this case, the processes covered in boxes 1112 and most of 1114 of FIG. 11 must be conducted at sufficiently low temperature to keep the transfer substrate frozen solid. This can be done by moving the assembly 700 of FIG. 7B into a freezer, including a walk-in freezer and glove-box freezer, and performing the processes outlined in boxes 1112 and most of 1114 of FIG. 11 in the freezer. The advantage of this process is the minimal time required to form, by freezing, and dissolve, by melting, the transfer substrate.

In this alternate freezing process, suitable transfer substrate forming solutions include:
Pure water
Standard buffers, such as TE, SSC, MES, PBS, and Good buffers
Mixtures of water and glycerol (typically 5-20% glycerol), or mixtures of standard buffers and glycerol
Mixtures of water or one of the standard buffers and any of the water-soluble solid transfer substrate forming materials listed above.

Alternately, non-aqueous solution and suspensions can be used. In general these include a solvent and a solute. In which case formation of the transfer substrate is by evaporating the solvent, and dissolution of the transfer substrate is by dissolving or re-suspending the dry solute compound in a suitable solvent, which may not be the same solvent used in the film forming solution. Alternately, the transfer substrate may be etched away. For example, the transfer substrate is composed of a novalak resin based photo resist. The transfer substrate may be removed by dissolving in acetone, or it may be exposed to UV-light and then etched away with an aqueous solution of high pH, such as a TMAH or KOH and water solution.

Additional layers may be added over or within the transfer substrate to aid in subsequent processing. For example, a water permeable paper or fabric piece may be applied over the film forming solution as it dries in the sample well, or a layer of adhesive tape may be applied to the backside of the transfer substrate.

Alternately, the transfer substrate may be formed of a compound with a moderate sublimation temperature. This method follows the standard method except as follows: after stretching the elastic substrate, removing any solution from the sample well, and either condensing a vapor of the compound onto the elastic substrate and fragments in the sample well or spreading a melt of the compound over the sample well. Dissolution of the transfer substrate then follows by evaporating the transfer substrate through sublimation. Suitable compounds include material with thin-film sublimation rates measuring greater than 1 micron per 24 hours at temperatures below 300 C, such as cyclododecane, camphor, and mixtures of these.

In a further alternate, the transfer substrate is not formed in-situ in the sample well. In this alternate, the transfer substrate maybe formed of any of the materials listed or following from this document. An alternate method follows that of the preferred embodiment, with the following modifications. The transfer substrate is formed separately from the sample well and elastic substrate, for example by casting the transfer substrate on a release liner and peeling the transfer substrate from the liner. The sample well may be optionally drained and dried. Then the transfer substrate is contacted to the fragments and surrounding elastic substrate areas. Processing then continues as presented herein by removing the transfer substrate from the sample well, wherein the fragments remain attached to the transfer substrate, a new elastic substrate is applied over the transfer substrate, and the transfer substrate is dissolved with a suitable solvent or sublimed or etched away. In further alternates to this method, the surface of the transfer substrate may be moistened with a solvent (e.g. water, alcohol, etc.) prior to being contacted to the fragments and elastic substrate. Further, the transfer substrate may include a supporting layer to aid in subsequent processing. For example, a water permeable paper backing may be used to support a thin water-soluble layer, in a structure resembling water-based carton sealing tape or a postage stamp with water-soluble adhesive. The thin water-soluble layer may be applied to the fragments and elastic substrate regions dry or first moistened.

Note, if the transfer substrate and/or elastic substrate assembly become too long to be easily processed, the transfer substrate can be cut into one or more pieces, and each piece then processed separately during the following cycles.

Alternate to lamination of new elastic substrate 1006 over transfer substrate 802, part of process in box 1114 of FIG. 11

Referring to FIG. 10, rather than laminating a sheet of silicone over the transfer substrate 802, uncured liquid silicone can be poured or spread over the transfer substrate 802 and part of the surrounding release liner 1004 and cured in place. Suitable silicones include Sygard 184 and Sylgard 186, which are two part silicones that cure at room temperature in approximately 24 hours after mixing. Curing time can be decreased to several hours or less with moderate heating to roughly 40 C to 60 C. Sylgard 186 has two advantages over Sylgard 184, first it is very viscous and will flow very little during curing from where it is initially spread, and second, the cured silicone rubber has significantly greater ultimate elongation. Hence the process is to form part of the stack-up shown in FIG. 10, starting from table top 1002, release liner 1004, and transfer substrate 802, wherein the side of the transfer substrate 802 that was adjacent to the last elastic substrate is away from release liner 1004. The two parts of the silicone are mixed and then degassed for roughly 30 minutes in a vacuum degas apparatus at or below room temperature. The silicone is then spread to the desired thickness (roughly 2 mm-5 mm) over the transfer substrate 802 and for 10 cm to 40 cm laterally beyond the transfer substrate onto the release liner 1004. If a silicone with lower uncured viscosity is used, a dam can be formed to contain the silicone, and made of wax or modeling clay 10 cm to 40 cm beyond and around the transfer substrate 802 on the release liner 1004. The silicone is then poured over the transfer substrate, filling the dammed area to the desired thickness. The silicone is cured at room temperature for 24 hours, or shorter time if mild heating is applied. In this way, the new elastic substrate 1006 is cast in place. In addition, the new elastic frame is formed simultaneously, as a new sample well is formed with the thickness of the transfer substrate 802. Note, if desired, additional material can be added to the bottom side of the transfer substrate to form a deeper new sample well.

Further process variations—Amplification of sample molecules and/or sample fragments Amplification of sample molecules and/or fragments by nick translation, primer extension, ligation of oligomers, ligase chain reaction (LCR), polymerase chain reaction (PCR), emulsion PCR, and other techniques, particularly methods designed for amplifying DNA or RNA molecules bound to a solid support.

Amplification of sample molecules and/or fragments by random primer extension.

After the sample molecules have been extended over the surface of the elastic substrate 104, as illustrated in FIG. 3, a random primer extension process can be used in sample well 108 to both generate the fragments and amplify both the fragments and the sample molecule. The sample molecules may be denatured and fixed to the elastic substrate as single stranded molecules prior to the amplification process.

In one process, the sample molecules are amplified and fixed in place by repeated cycles of random or non-random primer extension and fixing to the elastic substrate, prior to forming fragments.

In another process, a standard random primer extension process is modified by substituting the unmodified dNTPs (the four nucleotides dATP, dTTP, dCTP, and dGTP) with amine-labeled nucleotides and a lessor fraction of chain terminating nucleotides such as ddNTPs (the four dideoxynucleotides), as detailed above for the nick translation process. And as detailed above, the resulting amine-labeled primer extension produces are cross-linked to the temporary binding molecules that are impregnated in the elastic substrate.

Alternately, the process can proceed using random primers that have been modified to have one or more amine, thiol, sulfhydryl, or other reactive groups conjugated at or near their 5' ends, and extended with a mixture of unmodified dNTPs and chain terminating ddNTPs. In both process variations, the fragments generated are cross-linked to the temporary binding molecules impregnated into the elastic substrate 104. One or more cycles of random primer extension and cross-linking can be used, and the elastic substrate assembly 102 can be stretched in one or more directions between cycles. Stretching the elastic substrate assembly 102 after cross-linking and before the next random primer extension step can improve yield by hindering the annealing of complementary fragments that are already cross-linked to the elastic substrate.

Amplification by repeated cycles of annealing random oligomers to the sample molecule and to temporarily bound oligomers.

In this process, oligomers with reactive (cross-linkable) end-groups on either the 3'- or 5'-ends are annealed to the sample molecule and then cross-linked to the temporary binding molecules that are impregnated into the elastic substrate 104. This process can be repeated as desired to amplify the number of fragments (oligomers in this process) bound to the elastic substrate. Note that the elastic substrate assembly 102 can be beneficially stretched before any or all of the anneal/cross-link cycles, and thus limit the proportion of those fragments that are already bound to the elastic substrate bound that can rapidly anneal with complementary strands and thus prevent additional, free in solution, oligomers from annealing to the sample molecule and elastic substrate bound fragments. In a variation on this process, two sets of shorter random primers can be employed, one set having non-ligatable 3' ends and 5'-P ends and the other set having ends of 3'-OH and non-ligatable 5' ends, and a cross-linkable reactive group at or near either the non-ligatable 3' ends or the non-ligatable 5' ends. Both sets of random oligomers are added to the sample well 108 along with ligase and a standard ligation buffer, such as are available in commercial ligation kits or from Current Protocols in Molecular Biology, or other standard text. The process then proceeds as above with repeated cycles of annealing and ligation followed by buffer exchange and then cross-linking of the annealed random primer dimers to the temporary binding molecules. The annealing and ligation steps are typically done simultaneously and at a temperature near or above the melting temperature of all of the un-ligated random primers.

Alternate methods of subsequent processing of sample fragments—box 1118 of FIG. 11

Following completion of the spatial separation of the sample fragments, subsequent processing of the sample fragments is employed to obtain useful information from the fragments, including determination of some or all of the base sequence information of the fragments, determination of which of the fragments includes a particular run of bases or range of base sequences, determination of which fragments contain a recognition sequence of a predetermined nucleic acid binding protein, and any other useful information. Processes that are designed for analyzing molecules, including DNA, that are bound to a solid support are particularly applicable.

The fragments can be amplified by a suitable means after the spatial separation process and prior to the subsequent processing.

Subsequent processing for the determination of all or a portion of the base sequence of nucleic acid sample fragments include, but are not limited to: the method of labeled-probe-assemblies detailed in U.S. patent application Ser. No. 11/827,588, pyro-sequenceing, sequencing by synthesis, sequencing by incorporation, sequencing by ligation, highly parallel sequential ligation, sequential ligation with dye-labeled oligonucleotides, mass-spectroscopy of laser desorbed oligomers, chain termination sequencing, and other sequencing methods.

Sequencing of nucleic acid fragments can proceed by covering the fragments with a solution of labeled-probe-assemblies and hybridizing the complementary pairs of fragments and labeled-probe-assemblies. Those labeled-probe-assemblies that hybridized to fragments are extended in a direction approximately perpendicular to the direction in which the fragments were spatially separated. Attach the extended labeled-probe-assembles to the substrate, by a process such as drying. Place the substrate in a readout device, and collect the information encoded along the labeled-probe-assemblies, the ordering of the fragments and/or labeled-probe-assemblies, and optionally, the distance between fragments and/or labeled-probe-assemblies. The collected information is then analyzed and combined according to the ordering and distance data to generate sequence information about the whole original sample molecule.

Processing of the sample molecules and fragments to determine information about their physical structure can be done during and/or between the process steps of preparing the sample molecules, generating the sample fragments, and spatially separating the sample fragments, as well as after completion of the spatial separation process. In other words, the processes outlined in box 1118 of FIG. 11 can be moved to earlier in the process flow of FIG. 11 or spread throughout the process flow. For instance, labeled-probe-assemblies may be beneficially hybridized to the sample molecules and then temporarily bound to the elastic substrate as a means of generating sample fragments, and alternately, labeled-probe-assemblies may be hybridized to the sample fragments and further processed prior to the last stretching cycle of the spatial separation process. As a further alternate, the sample fragments are amplified prior to or after the final stretching cycle of the spatial separation process by repeated cycles of hybridization of random oligomers followed by temporary binding to the elastic substrate, by PCR with temporarily anchored primers, by ligation of primer sequences to the fragments and PCR with temporarily anchored primers, or by another method.

A method of using labeled-probe-assemblies to determine sequence data from the sample molecules can include: hybridizing labeled-probe-assemblies to the spatially separated sample fragments, extending the hybridized labeled-probe-assemblies over the elastic substrate in a second direction, approximately perpendicular to the direction in which the sample molecules were previously extended as outlined in box 11 of FIG. 1106, and fixing them to the elastic substrate. Additional stretching of the elastic substrate assembly in the second direction may be beneficial to allow the information encoded along the labeled-probe-assemblies to be further spatially separated and thus made individually resolvable by the data readout device, and one or more cycles of the stretching method described above can be utilized.

With sufficient spatial separation, individual fragments or islands of amplified fragments can be removed from the final elastic substrate and transferred to other vessels, such as a well of a micro-well plate, centrifuge tube, capillary tube, electrophoresis gel, solid supports, or support beads. The most benefit is typically gained when information about the ordering of the fragments on the final elastic substrate is not lost in the transfer process or subsequent processing. Once transferred, fragments can then be processed using any protocol for any means, such as amplification, sequencing, cloning, drug production, medical diagnostics, and mapping. For example, the fragments can be sequenced by standard chain-termination processes, including capillary electrophoresis separation processes, or sequencing by synthesis techniques such as those developed 454 Life Sciences, Branford, Conn., and Pacific Biosciences, Menlo Park, Calif., or by nano-pore sequencing techniques in which the passage of a nucleic acid molecule through a small orifice is monitored to determine information about the base sequence of the molecule. Methods for removing fragments from the final elastic substrate include dividing the substrate into pieces or cutting pieces from the substrate, wherein each piece holds at most a limited number of fragments. Any method of dividing the substrate into small pieces can be used including microtome cutting, scribe and break, laser dicing, mechanical sawing, FIB cutting, and methods used in the semiconductor processing industry such as lithographic patterning and etching. Each excised piece is then manually moved to the desired vessel. Alternately, individual fragments or small islands of amplified fragments can be removed from the final substrate by contacting the desired fragments, and region surrounding the desired fragments, with a small capillary tube filled with a suitable solvent, such as ethyl alcohol, isopropyl alcohol, water with surfactant, hot water, or non-polar solvents. After collecting a fragment, the capillary is then emptied into the desired vessel. Other methods based on micro-manipulator tools, micro and nano-contact printing and pad inking techniques, laser desorption, and matrix-assisted laser desorption can be used. Any of these processes can be run serially or in parallel, with multiple manipulators or capillaries moving simultaneously, and robotic means can be employed. Determining where to cut or place a capillary can be done actively or blindly using a predetermined pattern. Fragments can be labeled, stained, on the final elastic substrate, and a detection device used to locate the fragments and guide the cutting or capillary placement. Blind cutting or capillary placement can be optimized by using information about the sample molecule, processing (to estimate sample molecule placement, direction of extension, fragment size, and original distance between fragments), and total amount of spatial separation (to estimate final distance between fragments).

Additional alternate materials and methods are detailed for the nano-patterned substrate method and the accordion folded substrate method, and it is clear that most of these alternates and variations can also be applied to the elastic substrate method.

Description of a Nano-Patterned Substrate Assembly and Method

The description of an alternate apparatus providing for the spatial separation of ordered fragments that are generated from long sample molecules is illustrated in FIGS. 12 and 13. FIG. 12 is a top-view illustration and FIG. 13 illustrates a cross-section through a portion of the assembly along the direction 1 defined in FIG. 12. In a first variation of this alternate embodiment, a specially fabricated substrate assembly is employed. As illustrate in FIG. 12, the substrate assembly 1200 is composed of a support layer 1202 and a patterned substrate 1204 illustrated in cross-hatch. In this embodiment, the substrate 1204 is a single continuous element in the form of a long wire, of nominally rectangular cross-section, that is folded back and forth upon itself in a plurality of zig-zags or compressed S-turns and the whole form being approximately in a single plane. Many other substrate layouts are possible. The substrate 1204 is typically fabricated of silicon dioxide, silicon nitride, a layered structure of silicon dioxide and silicon nitride, silicon oxy-nitride, thin diamond film, diamond-like carbon, graphite, a metal such as gold or platinum or titanium, an alloy, an organic polymer material, such as a photo-resist material or an electron-resist material, plasma enhanced chemical vapor deposition (PECVD) deposited hydrocarbon or fluorocarbon, or a layered structure of an organic polymer and one of the other materials listed. One or more regions of anchor molecules 1205 are located on the substrate 1204 and provide for attaching one or both ends of the sample molecules to the substrate assembly 1200. The top-view of the substrate assembly 1200 is aligned along two directions labeled as 1 and 2 in FIG. 12. The length of the substrate 1204 along direction 1 can range from roughly 1 mm to 300 mm or shorter or longer, and is typically in the range of 5 mm to 10 cm. The width of the substrate 1204 along the direction 2 can range from roughly 0.01 mm to 300 mm, and is typically in the range of 0.1 mm to 50 mm. The line-and-space pitch between adjacent S-turns of the substrate 1204 is generally less than 300.nm (nanometers), and typically in the range of roughly less than 10 nm to 100 nm, and preferably less than roughly 50 nm. The lines and spaces need not be of equal width. For clarity, FIG. 12 illustrate substrate 1204 with relatively small numbers of S-turns. In most applications, the substrate will have at least thousands of S-turns, and often millions, tens of millions, or more S-turns. Likewise, in FIG. 27, patterned substrate 2604 is illustrated for clarity with relative few nano-patterned features.

As illustrated in FIG. 13, substrate 1204 has an active surface 1206 that does not contact the support layer 1202, and the surfaces of substrate 1204 other than the active surface 1206 have a hydrophobic surface layer 1208. The active surface 1206 includes functional groups 1210, such as molecules including one or more available hydroxyl, amine, thiol, sulfhydryl, vinyl, carboxyl, carbonyl, psoralen, tetrafluorophenyl azide, maleimide, succinimide, and/or avidin group to facilitate the attaching of a sample molecule(s) to the substrate 1204. Hydrophobic surface layer 1208 can be a self-aligned monolayer of ODT or OTS (octadecyltrichlorosilane), a layer of vapor deposited HMDS (hexamethyldisilazane), or other hydrophobic silane coupling agent. For clarity, a limited number of features 1206, 1208, 1210, and 1212 are indicated in FIG. 13. The support layer 1202 is typically made from a low melting temperature wax, paraffin wax, synthetic wax, a low melting temperature polymer, a low melting temperature hydrophobic polymer, polyethylene, polypropylene, polystyrene, silicone rubber, other elastomer, or a silicone gel. The support layer 1202 contacts most of hydrophobic surface layer 1208 and hence securely holds the substrate 1204. The support layer 1202 has an exposed surface 1212 that is roughly co-planar with the active surface 1206. The width along direction 1 of each cross-section of substrate 1204, as illustrated in FIG. 13, is typically less than 100.nm, often less than 35.nm, and preferably less than 10.nm. Often it is beneficial to employ the minimum width that can be processed and handled. The distance along direction 1 between adjacent portions of substrate 1204, as illustrated in FIG. 13, is typically less than 300.nm, and can beneficially vary over the substrate assembly. For instance, in an alternate embodiment illustrated in FIG. 17, every other distance is minimized, and the remaining distances are optimized to the information acquisition process outlined in box 1912 of FIG. 19.

Fabrication of the Nano-Patterned Substrate Assembly

One method for fabricating of the nano-patterned substrate assembly is presented in FIG. 18. Many alternate methods can be envisioned using the techniques of thin-film processing developed for semiconductor processing and MEMs (micro-electro-mechanical system) fabrication. Standard lithography and nano-lithography patterning techniques can be employed, such as: electron-beam lithography, elastomer stamp micro- and nano-contact printing, X-ray and/or DUV (Deep ultra-violet) lithography, 1-line lithography, X-ray and/or DUV standing wave interference patterns, and any other lithography and/or patterning technique having the desired resolution. Patterning techniques can include; plasma etching, reactive ion etching (RIE), anisotropic plasma etching, ion milling, sputtering, focused ion beam (FIB) etching, ashing, wet chemical etching, gas phase etching, laser ablation, micro-embossing, electron-beam cross-linking or decomposition, and other patterning processes. Regions of anchor molecules 1205 can be contacted printed onto the substrate by standard means such as described above and in the open literature.

Operation of the Nano-Patterned Substrate to Analyze Sample Molecules

Operation of the Nano-Patterned substrate is presented in FIG. 19. Techniques for performing tasks such as those outlined in boxes 1904, 1906, 1908, and 1912 of FIG. 19 can use the same methods as presented above and/or techniques available in the literature. In addition, other standard cross-linking protocols and reagents can be used to more permanently cross-link the sample molecules to the substrate (see for example cross-linking protocols in literature by Pierce Biotechnology Inc and Sigma-Aldrich Inc, references therein, and protocols in the open literature), and alternately, the sample molecules can be bound to the substrate after extension by thorough drying and/or standard methanol/acetic acid fixation and/or UV-cross-linking.

Figure 14:
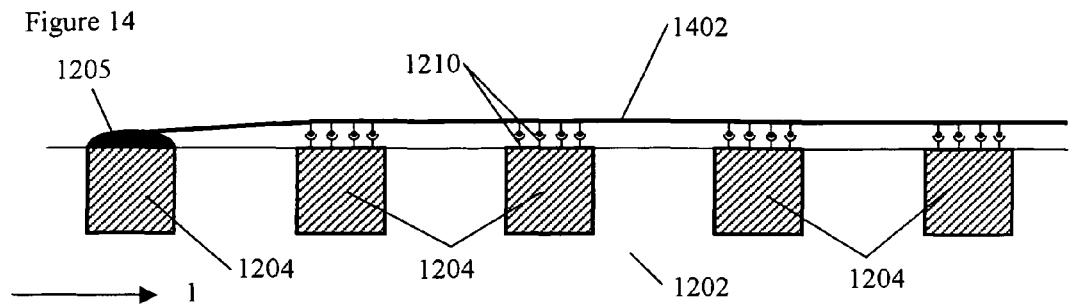
FIG. 14 illustrates a cross-section through a portion of the Nano-Patterned substrate of FIG. 12 with an attached sample molecule.

Starting in box 1900 of FIG. 19, the sample molecules, typically DNA and/or RNA, are recovered and prepared into a solution. Optionally, reactive end-groups are conjugated to, preferably, one end of each sample molecule. In box 1902, the substrate assembly is prepared and placed in a reaction vessel, a dish of approximately the same size as the substrate assembly so as to minimize solution volumes required. Alternately, a silicone rubber frame can be placed over the top of the substrate to confine the solutions applied. In box 1904, the solution containing the sample molecules is applied to the top of the substrate, and the reactive end-groups on the sample molecules are allowed to bind to the anchor molecules on the substrate. In box 1906, the sample molecules are extended over the surface of the substrate assembly approximately along direction 1, as defined in FIG. 12. Any suitable method of extension can be employed, including tilting the substrate assembly up such that the solution runs off the substrate assembly along direction 1. FIG. 14 illustrates a cross-section along direction 1, defined in FIG. 12, that includes support layer 1202, anchor molecules 1205 and a portion of an extended sample molecule 1402 cross-linked to functional molecules 1210. For clarity, not all instances of functional molecules 1210 are indicated. In FIG. 1908, and referring to FIGS. 12 and 13, the sample molecules are attached to the substrate 1204. This can be done in one of more stages, and include processes of drying, heating, UV cross-linking, UV-cross-linking to substrate bound psoralen or other UV-cross-linker, sample molecule modification to provide reactive groups and forming cross-links between these reactive groups and functional groups 1210 on the substrate 1204. Note that function groups 1210 are optional, as thorough drying and/or mild heating is sufficient to attach the sample molecules to certain substrates, such as substrates 1204 made of silicon dioxide.

Figure 15:
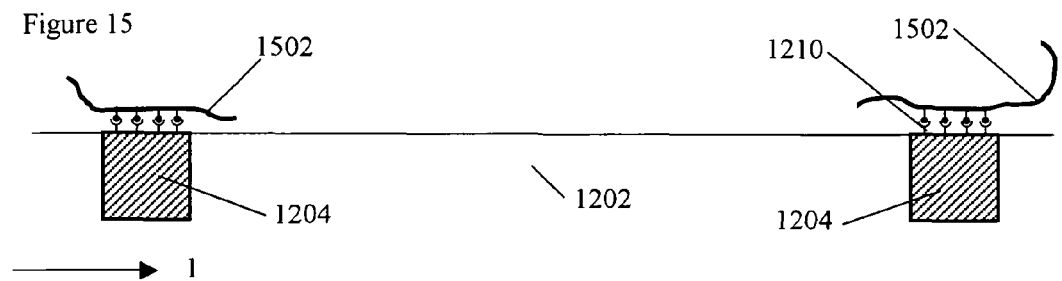
FIG. 15 illustrates a cross-section through a lesser portion of the Nano-Patterned substrate of FIG. 14 with attached fragments of sample molecule after elongation of the Nano-Patterned substrate along a direction roughly parallel to the plane of the illustration.
Figure 16:
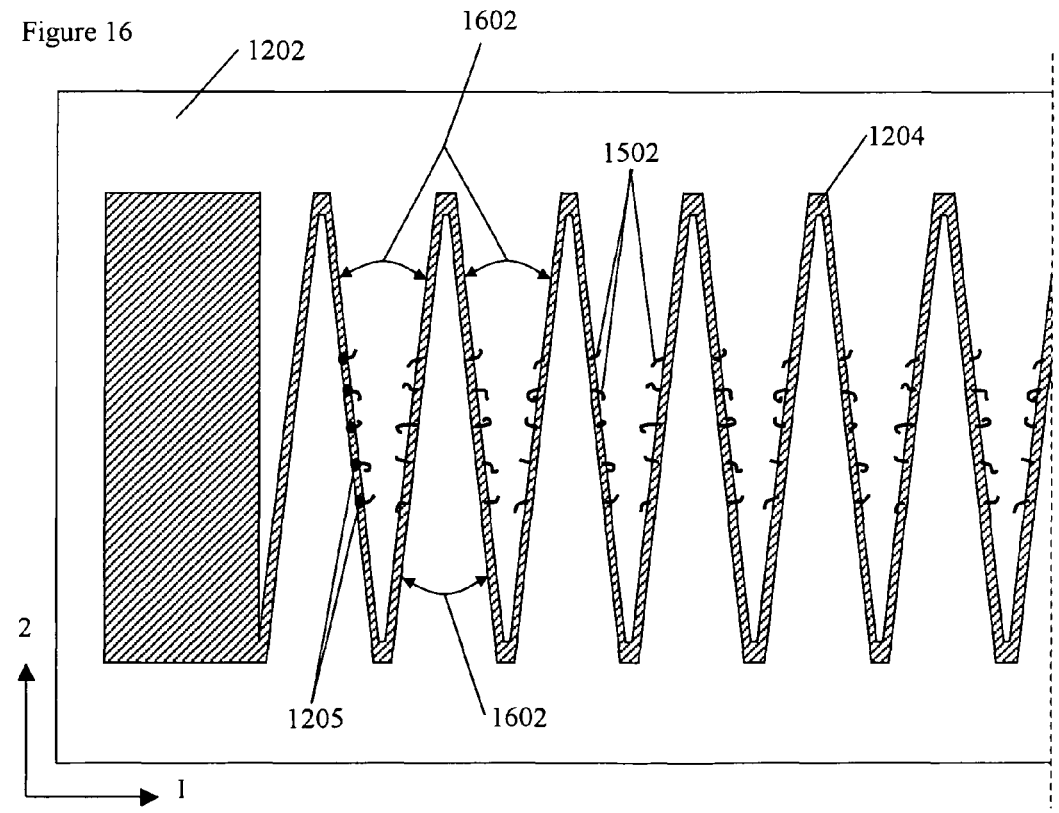
FIG. 16 illustrates a top-view of a portion of the Nano-Patterned substrate of FIG. 15 with attached sample molecules after elongation of the Nano-Patterned substrate roughly along direction 1 as illustrated in the figure.

In box 1910, the substrate assembly is placed in a vessel containing an aqueous solution. This vessel is of sufficient size such that the substrate assembly can be expanded to its final size within the vessel. The substrate assembly is placed in the aqueous solution such that the top surface of the substrate is contacting the solution. The aqueous solution is then heated until the support layer 1202 is softened and/or melted, and then the two opposite ends of the substrate 1204 along direction 1 are pulled along the direction of direction 1 until the desired final extension is reached. The aqueous solution is then cooled below the melting and/or softening temperature of the support layer 1202, making the support layer a structural support layer. In the process of extension, the ultimate elongation of the sample molecules is exceeded and they break into fragments, each fragment being attached to the substrate 1204. FIGS. 15 and 16 illustrate the configuration of the extended substrate assembly with sample molecule fragments. FIG. 15 illustrates a cross-section along direction 1 of a portion of the extended substrate assembly, and FIG. 16 illustrates a top-view of a portion of the extended substrate assembly. FIG. 15 includes regions of substrate 1204, functional molecules 1210, support layer 1202, and fragments 1502. For clarity, not all instances of functional molecules 1210 are indicated. FIG. 16 includes a portion of substrate 1204, support layer 1202, and fragments 1502, and the angle between adjacent legs of the S-turns 1602, which are the angles between adjacent zig-zags. Note, the extension is along direction 1 as defined in FIGS. 12 and 16. A final extension ratio is defined as the final distance between adjacent fragments divided by the initial distance, and substrate assemblies can be designed to achieve final extension ratios of tens of millions. However more typical final extension ratios are of order ten thousand and less, and can beneficially be ten or less depending on the subsequent processing to be conducted. The amount of extension illustrated in FIGS. 15 and 16 is limited so as to make the illustrations clear and understandable. In real applications, the relative separation between adjacent fragments can be much greater, and the acute angle between adjacent legs of each S-turn 1602 can be much greater than that illustrated in FIG. 16. The angle between adjacent legs of the S-turns 1602, shown in FIG. 16, can be as large as 180 degrees at maximum extension, such that the S-turns are completely straightened.

An alternate method for extending a nano-patterned substrate employs the elastic substrate method detailed above and in FIG. 11. In this alternate method, the substrate 1204 is either fabricated on the elastic substrate 104, see FIG. 1, or transferred to and temporarily attached to elastic substrate 104 at any point prior to its extension. Temporarily bonding the substrate 1204 to elastic substrate 104 typically only requires contact the two substrates together, preferably with both surfaces dry. Typically, the substrates are temporarily joined such that surface 1206 is away from elastic substrate 104 or new elastic substrate 1006. The processes detailed in FIG. 11, boxes 1110 through 1116 are then used to extend the substrate 1204.

Figure 27:
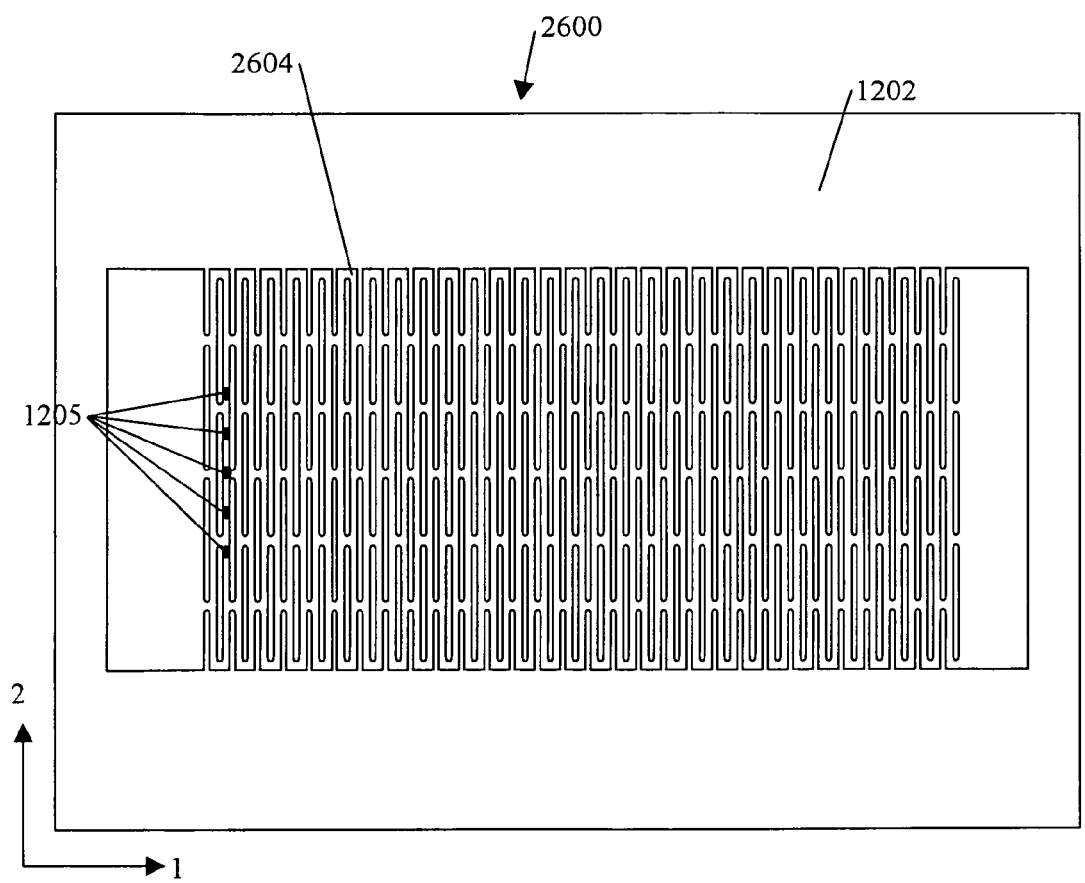
FIG. 27 illustrates a top view of a further alternate nano-patterned substrate.

A further alternate method of extending a nano-patterned substrate employ a pair of micro-manipulators connected to precision linear actuators to urge or pull the ends of the substrate such that it is extended. Including oversized ends, on either sides of the nano-patterned central region, as illustrated in FIG. 27 on substrates 1204 and 2604, respectively, can be used as attachment points for the micro-manipulator tools.

Before or after extension of the substrate, the sample molecules and/or fragments can be amplified, as is beneficial to the subsequence processing. Any suitable amplification method can be employed. For example the sample fragments can be amplified, by repeated cycles of hybridization of random oligomers followed by binding to the substrate, by PCR with anchored primers, by ligating on primer sequences to the fragments followed by PCR with anchored primers, by emulsion PCR, by any of the processes presented above, or by another process, particularly those designed for amplifying DNA and/or RNA molecules bound to a solid support.

As outlined in box 1912 of FIG. 19, the next step is to analyze the spatially separated fragments. For DNA and RNA samples, typically this means determining the base sequence of all or a portion of each of the individual fragments. Any suitable method can be employed, and methods designed for use with surface bound fragments are readily applied. Subsequent processing for the determination of all or a portion of the base sequence of DNA sample fragments include, but are not limited to: the method of labeled-probe-assemblies detailed in U.S. patent application Ser. No. 11/827,588, pyrosequencing, sequencing by synthesis, sequencing by incorporation, sequencing by ligation, highly parallel sequential ligation, sequential ligation with dye-labeled oligonucleotides, mass-spectroscopy of laser desorbed oligomers, chain termination sequencing, and other sequencing methods. Data collected from individual fragments are then combined in the order in which the fragments appear along the extended substrate to provide information about the whole of the sample molecule(s).

Alternate Embodiments of the Nano-Patterned Substrate and Methods of Operation

Figure 17:
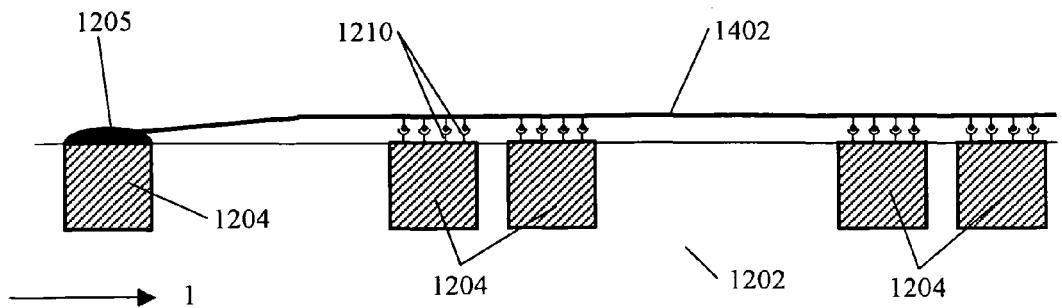
FIG. 17 illustrates a cross-section through a portion of an alternate Nano-Patterned substrate with an attached sample molecule.
Figure 22:
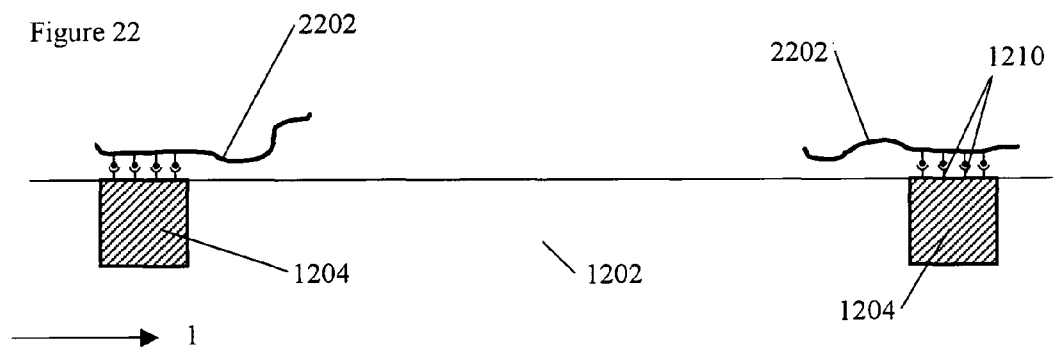
FIG. 22 illustrates a cross-section through a lesser portion of an alternate Nano-Patterned substrate with attached fragments of sample molecule after elongation of the Nano-Patterned substrate along a direction roughly parallel to the plane of the illustration.
Figure 23:
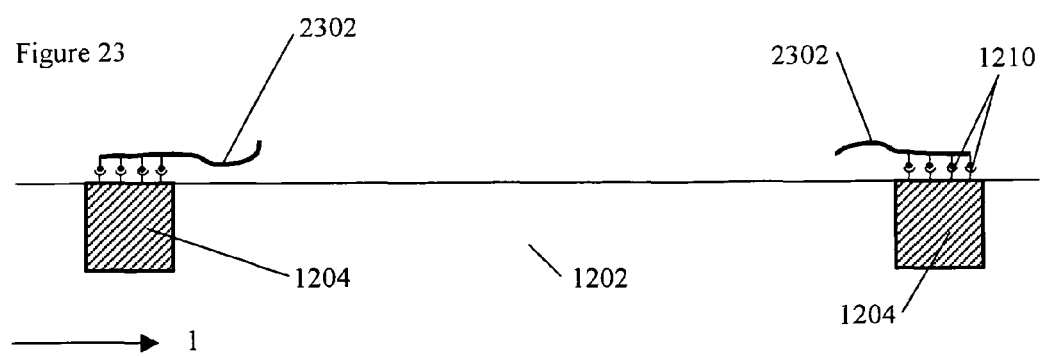
FIG. 23 illustrates the cross-section of FIG. 22 after a portion from each end of each fragment of sample molecule has been consumed.

As discussed above, FIG. 17 illustrates a cross-section view along direction 1 through a portion of an alternate substrate layout in which the spacing between adjacent portions of the substrate 1204 alternate between short (minimal) and longer. Portions of support 1202, regions of substrate 1204, anchor molecules 1205, a portion of an extended sample molecule 1402, and functional molecules 1210 are indicated in FIG. 17. For clarity, not all instances of features 1210 are indicated. In top view, this alternate patterned substrate would be similar to that illustrated in FIG. 12, but with alternating wider and narrower cutouts, void spaces, between zig-zags. The substrate assembly can be made by the method of FIG. 18. Using such a substrate can follow the process provided in FIG. 19. After the extension of the substrate per box 1910 of FIG. 19, FIG. 22 illustrates a cross-section along direction 1 through a portion of the extended substrate 1204, showing the space between two adjacent portions of substrate 1204 that were the longer distance apart. Portions of support 1202, regions of substrate 1204, fragments 2202, and functional molecules 1210 are indicated in FIG. 22. For clarity, not all instances of features 1210 are indicated. In general, each fragment 2202 of sample molecule 1402 (of FIG. 17) is attached to a portion of substrate 1204 and has two dangling ends, one long and one short, as predetermined by the alternating spaces in the un-extended substrate. An additional beneficial step can be applied between steps outlined in boxes 1910 and 1912, in which the sample molecule fragments are treated with a nuclease for a limited time. The function of the nuclease treatment is to consume all fragments inward from each dangling end by an approximately equal amount, such that the shorter dangling ends are completely consumed, as illustrated in FIG. 23. FIG. 23 illustrates a cross-section along direction 1 through a portion of the extended substrate 1204, after nuclease treatment. Portions of support 1202, regions of substrate 1204, nuclease digested fragments 2302, and functional molecules 1210 are indicated in FIG. 23. For clarity, not all instances of features 1210 are indicated. This only leaves one dangling end of fragment per portion of substrate to subsequently analyze. Nucleases particularly beneficial to this process are single-strand or double-strand specific exonucleases with low processivity.

Another alternate embodiment is presented in FIGS. 20, 21, and 24-26. In this embodiment, the extended sample molecules are patterned using lithography and/or micro-contact printing techniques to form fragments, and in this case, the fragments have only one dangling end per portion of substrate. To allow for the alignment of a second patterning step to the first patterning step (in which the Nano-patterned substrate is defined), the support layer is backed-up by a rigid silicon wafer. This is done by forming the patterned thin film substrate on a first silicon wafer and bonding this to a second silicon wafer using a wafer bonding tool. As before, a low melting and/or softening temperature support layer is employed and in this case doubles as the bonding agent, as detailed in box 2006 of FIG. 20. A general fabrication process is detailed in even numbered boxes 2000 through 2012 of FIG. 20.

In FIG. 21, the method of use is detailed. Boxes 2100, 2102, 2104, 2106, and 2108 of FIG. 21 detail the standard processes for generation a substrate and placing sample molecules over the substrate. Box 2109 of FIG. 21 covers the unique steps, including the optional formation of a water-soluble layer to protect the extended sample molecules.

Figure 24:
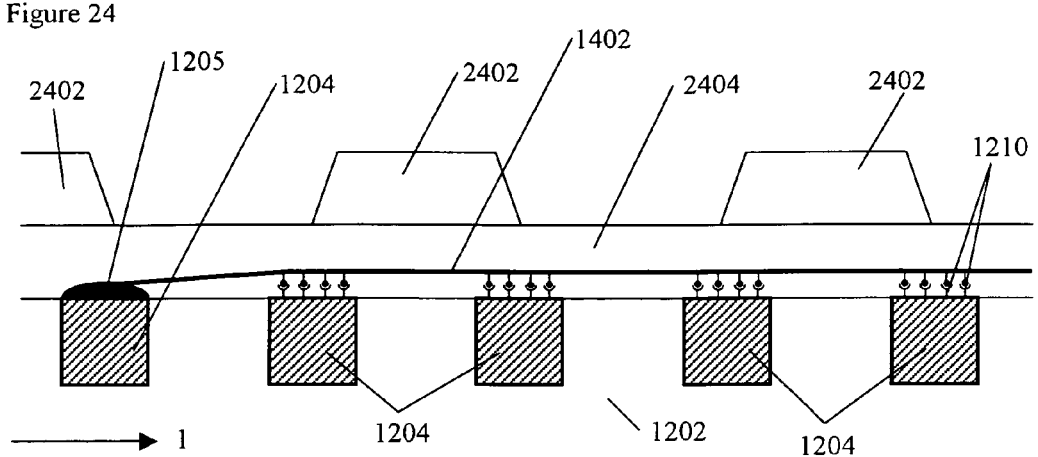
FIG. 24 illustrates a cross-section through a portion of an alternate Nano-Patterned substrate with an attached sample molecule, encapsulating layer, and patterned resist material.

Such a layer can be formed of PVOH (for example Elvanol 51-05) or any of the other film forming materials listed above. Whether or not this water-soluble layer is employed, a layer of resist (often a photo-resist or electron-resist) is applied, exposed, and developed. As an alternate, a resist material can be applied pre-patterned by micro- or nano-contact printing methods. FIG. 24 illustrates a cross-section of a portion of the substrate assembly, as in FIG. 14, with patterned resist 2402 and optional water-soluble layer 2404. FIG. 24 also illustrates support layer 1202, anchor molecules 1205 and a portion of an extended sample molecule 1402 cross-linked to functional molecules 1210. For clarity, no all instances of functional molecules 1210 are indicated.

Figure 25:
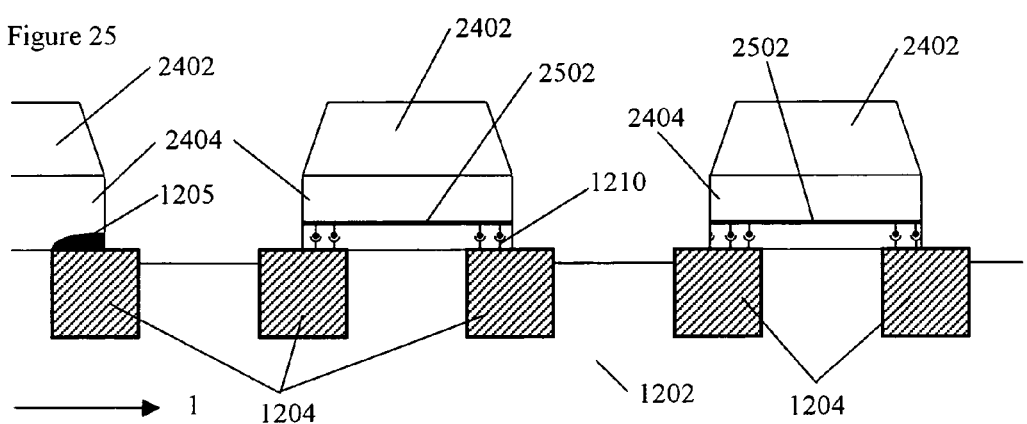
FIG. 25 illustrates the cross-section of FIG. 24 after exposed portions of the encapsulating layer and attached sample molecule have been etched away.
Figure 26:
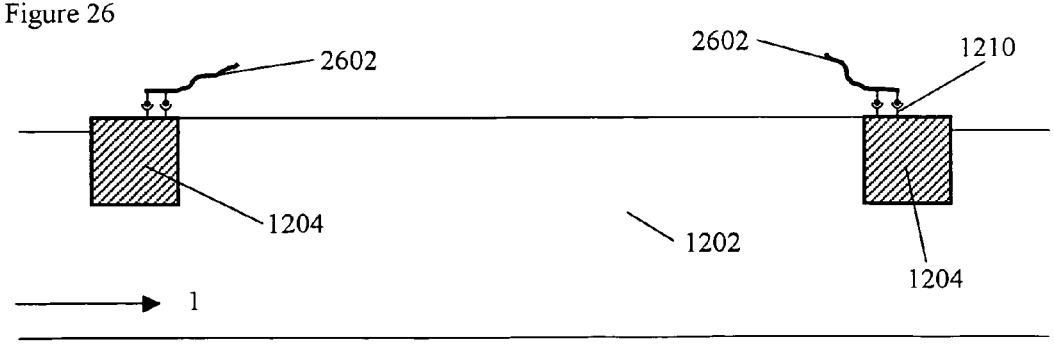
FIG. 26 illustrates a cross-section through a lesser portion of the Nano-Patterned substrate of FIG. 25 with attached fragments of sample molecule after elongation of the Nano-Patterned substrate along a direction roughly parallel to the plane of the illustration.

An etching method is then used to etch any portions of sample molecules not protected by resist, as illustrated in FIG. 25, wherein etched fragments 2502 are created by the etching process. FIG. 25 also illustrates support layer 1202, anchor molecules 1205 and etched fragments 2502 of sample molecule 1402 (FIG. 24) cross-linked to functional molecules 1210. For clarity, no all instances of functional molecules 1210 are indicated. Any suitable etching method can be used, such as those listed above. Following etching, the remaining resist is removed and any water-soluble layer is dissolved and removed. Optionally, mechanical support elements are attached to the two opposite ends of the substrate along direction 1. These optional support elements can be made of pieces of silicon wafer and can be glued to the substrate with a room temperature curing epoxy, RTV silicone adhesive, or double-sided tape. In box 2110 of FIG. 21, the substrate assembly is placed in a vessel that is large enough to contain the extended substrate. An aqueous solution is added over the substrate and is heated to soften and/or melt the support layer. The opposite ends of the substrate along direction 1, or the optional support elements bonded to these ends, are pulled apart to extend the substrate to it final length. FIG. 26 illustrates a portion of a cross-section along direction 1 showing two portions of substrate, each with an attached fragment 2602 of sample molecule 1402 (FIG. 24). Each fragment 2602 having one dangling end for subsequent processing as outlined in box 2112 of FIG. 21. FIG. 26 also illustrates support layer 1202 and fragments 2602 of sample molecule 1402 (FIG. 24) cross-linked to functional molecules 1210. For clarity, no all instances of functional molecules 1210 are indicated.

Further alternate patterned substrates use recesses, instead of cutout regions. For example, alternates to the patterned substrates illustrated in FIGS. 12 and 27 use variations in thickness of patterned substrate rather than void spaces. Where there are void spaces in patterned substrates 1204 and 2604, the alternate substrates would have thinned regions. The function of the thinned regions is to concentrate any mechanical stresses in those regions, relative to the thicker regions. In operation, mechanical forces are applied to extend the patterned substrate along direction 1, see FIGS. 12 and 27, and the stresses generated in the patterned substrate cause the thinned regions to fracture and/or tear, after which point the patterned substrate will extend by deforming the intact thick regions. Furthermore, the patterned substrate can be constructed of two of more stacked layers, and the recessed regions formed by etching through upper layers and stopping on (not etching) layers lower down in the stack. For certain manufacturing and sample processing methods, patterned substrates having recessed regions instead of cutout regions can be more easily processed and handled. Patterned substrates can have both cutouts and recesses.

In patterned substrate which include cutouts and recesses, any cross-section view along the whole patterned substrate looking into the plane normal to direction 2, as indicated in FIGS. 12 and 27, will have either a plurality of cutout regions (void spaces) and/or a plurality of recesses (thinned regions). The plane of such a cross-section includes the direction in which the patterned substrate is to be extended. FIG. 13 illustrates a portion of such a cross-section. A patterned substrate that does not include a plurality of cutouts or recesses in such a cross-section will either be limited in maximum extension to the ultimate elongation potential of the material used to construct the patterned substrate or will fracture in a poorly controlled manor.

Further Variations on the Nano-Patterned Substrate

Many variations on the Nano-Patterned apparatus, assembly, and method are readily envisioned, and most of the methods and materials detailed for the elastic substrate method and accordion folded substrate method and their alternates and variations can also be applied to the nano-patterned substrate method. Likewise, methods and materials detailed for the nano-patterned substrate technique are applicable to the other techniques. Specific further variations include the following:

- A thin substrate that will spontaneously crack into small pieces upon softening, melting, or stretching of the support layer, thus etched features within the substrate are optional.
- Alternate patterns of etching such as a multitude of pairs of etched lines extending in from opposing sides but not meeting in the middle and all being approximately parallel, and between adjacent pairs of pairs, an etched line running parallel to the pairs of etched lines and extending across the middle of the substrate but not extending to the sides of the substrate.
- A substrate patterned as illustrated in FIG. 27, and variations on this pattern. FIG. 27 illustrates alternate substrate assembly 2600 composed of substrate 2604 connected to support layer 1202 and, optionally, one or more regions of anchor molecules 1205.
- Nano-patterned substrates fabricated of electron-beam resist, photo-resist, or micro-contact printed or nano-contact printed inks and other compounds, such as substrate 1204 illustrated in FIG. 12, or substrate 2604 illustrated in FIG. 27. Sample molecules can be extended over the patterned materials, and processed as detailed above. Alternately, sample molecules extended onto a surface, and then any of the above material applied over the sample molecules and patterned.

Etch the substrate layer to form multiple pieces of substrate, such as: parallel strips, tiled rectangles, squares, rounds, etc.

Etch only partially through the substrate layer such that the substrate spontaneously cracks along the etched tracks upon softening, melting, or stretching of the support layer.

A substrate formed by a layer of closely packed particles or nano-particles embedded in a low melting temperature wax, or other material, such as those used to form the support layer.

More or fewer regions of anchor molecules 1205, including no regions 1205.

Transferring already formed fragments to a nano-patterned substrate, such as from an elastic substrate, prior to extending the nano-patterned substrate.

Where fragments are nucleic acids, use a patterned substrate that can be extended into a long continuous wire or fiber-like structure, such as the patterned substrate illustrated in FIG. 12. Attach fragments over the patterned substrate per processes detailed previously. Sequence the fragments, or portions of each fragment, using the method of labeled probe assemblies detailed in U.S. patent application Ser. No. 11/827,588. Hybridize labeled probe assemblies to the fragments. Extend the patterned substrate and draw the extended patterned substrate, in a fiber-like conformation, from solution, allowing the hybridized labeled probe assemblies to extend along the long axis of the fiber-like structure and adhere to it. Pass the fiber-like structure through a readout device and collect a continuous, time varying signal correlated with the information encoded along the labeled probe assemblies. Furthermore, record the distance between fragments and/or labeled probe assemblies along the fiber-like structure. Alternately, fix one or more of the fiber-like structures to a flat substrate and collect data from whole regions of the flat substrate substantially simultaneously in an alternate readout device.

Description of an Alternate Embodiment—Accordion Folded Substrate Assembly

A further alternate embodiment employs an approximately planar substrate that is folded into an accordion folded or pleated structure and is referred to herein as the accordion folded substrate method. Such a substrate can be compressed, such that the folds are close together, and the sample molecule extended across the tops of many folds, in a direction approximately perpendicular to the long axis of the folds, and attached to the many folds. The sample molecule is then divided into fragments, by any means, including mechanical stretching. Forces or urging applied to the substrate then extended the substrate in the direction perpendicular to the long axis of the folds, thus unfolding the folds, whereby the fragments are spatially separated.

Figure 28:
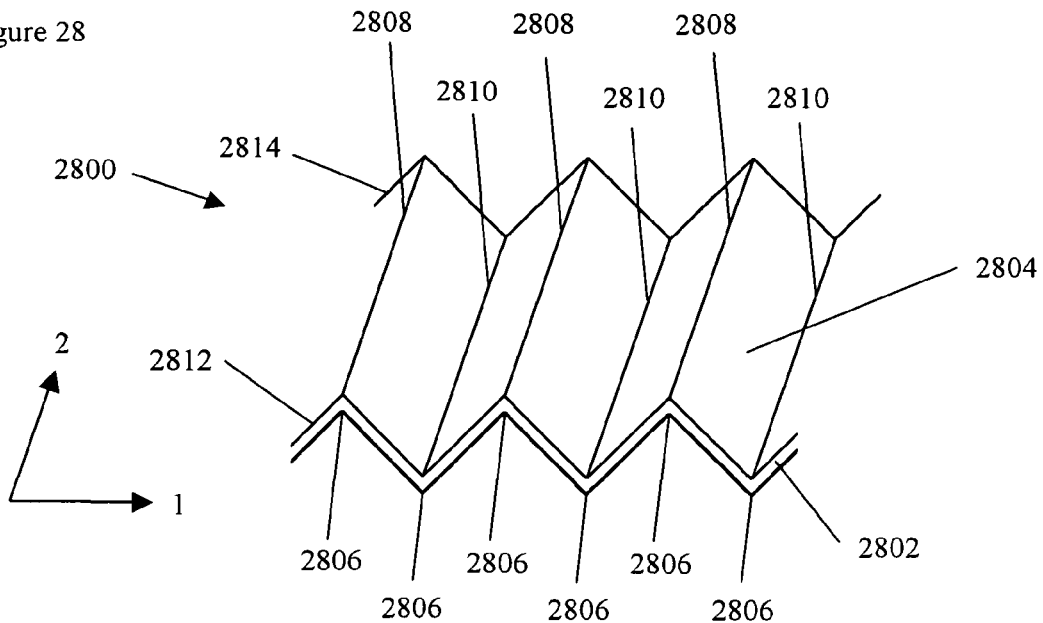
FIG. 28 illustrates a perspective view of a portion of an accordion folded substrate.
Figure 29:
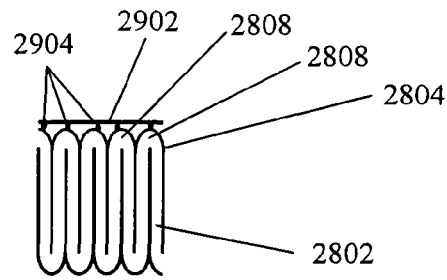
FIG. 29 illustrates a cross-section through a portion of a fully compressed accordion folded substrate with attached sample molecule.
Figure 30:
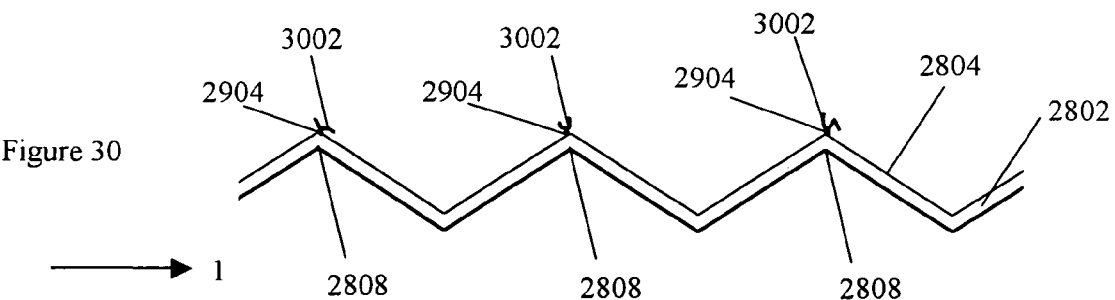
FIG. 30 illustrates a cross-section through a portion of a mostly open accordion folded substrate with attached fragments of a sample molecule.

FIG. 28 illustrates a limited region of an exemplary accordion folded substrate 2800. Features include layer 2802 and top surface 2804 of layer 2802. Folds 2806 can be further defined as convex folds 2808 and concave folds 2810 relative to top surface 2804. Folds 2806 are aligned approximately along direction 2, and convex folds 2808 and concave folds 2810 alternate along direction 1. Edges 2812 and 2814 are also illustrated but the ratio of width along direction 2 to pitch of the folds along direction 1 is not illustrated to scale. FIG. 29 illustrates a cross-section perpendicular to direction 2 of a limited portion of a fully compressed folded substrate 2800. Layer 2802 is indicated. A sample molecule 2902 is extended over top surface 2804 and attachment points 2904 show where sample molecule 2902 is attached to top surface 2804. For clarity, only three of five attachment points 2904 are specifically indicated, and only two of five convex folds 2808 are indicated in FIG. 29. FIG. 30 illustrates the same view as FIG. 29 but with folded substrate 2800 nearly fully open. Fragments 3002 of sample molecule 2902 are attached to top surface 2804 of layer 2802 at attachment points 2904. FIG. 30 also indicates several convex folds 2808. In a complete accordion folded substrate, there are a plurality of folds 2806. The thickness of layer 2802 is typically less than 1 micron, and beneficially less than 10 nanometers, with the minimum thickness set by mechanical robustness and handling limitations. The minimum distance between adjacent convex and concave folds is typically in the range of approximately 1 millimeter to 1 micron, and other distances are acceptable. The total number of folds can range from less than 100 to greater than 1 million, and the optimum number depends primarily on the length of the sample molecule and the thickness of layer 2802. The width between edges 2812 and 2814 is typically in the range of 100 microns to 10 centimeters.

In an alternate embodiment, extensions of layer 2802 at both ends along direction 1, are provided and used to attach the folded substrate 2800 to a mechanical actuator. The mechanical actuator provides forces or urging to compress and open the folded substrate 2800. Variations not shown in the illustrations include optional additional layers connected to layer 2802, wherein layer 2802 and any additional layers can be discontinuous, and optional supporting members connected to folded substrate 2800.

Methods and materials for fabricating an accordion folded substrate include methods and materials commonly used in the semiconductor processing industry and MEMs fabrication. These methods include vee-groove etching of oriented single crystal silicon using micro-lithography and anisotropic etching processes, such as KOH etching. Vee-groove etching is used to fabricate a mold for the folded substrate. Thin film growth and deposition processes and micro-lithography and etching process are then used to form the substrate on the mold. The completed folded substrate is removed from the silicon mold by either etching away the silicon, for example with XeF2, KOH, or nitric acid—hydrofluoric acid mixtures, or by depositing a release layer on the mold prior to forming the folded substrate and undercutting or lifting off the completed folded substrate. Materials suitable for fabricating a folded substrate include inorganic materials such as silicon dioxide, silicon nitride, silicon oxy-nitride, gold, platinum, palladium, graphite, carbon, diamond film, diamond-like carbon, and combinations of these. Suitable organic materials include PECVD deposited hydrocarbon films, PECVD deposited fluorocarbon films, and other PECVD organic films, electron-beam or UV-light cross-linked thin organic layers, electron-beam or UV-light cross-linked membranes, and electron-beam or UV-light cross-linked lipid bilayers. Combinations of patterned materials can be beneficial, for example folds can be made of flexible PECVD deposited hydrocarbon film, and portions between folds made of stiffer silicon nitride. Alternately, the folded substrate can be made of a stack of two or more thin layers; the stack including flexible materials and rigid materials. The flexible materials serving to hold the structural rigid materials together when they are cracked as the folds are compressed and opened.

Note that it is acceptable and expected that substrates fabricated of rigid materials will form cracks at the folds when fully compressed or opened. Furthermore, a folded substrate need not fully compressed or completely opened to be functional. Additional layers or treatments can be added to the top surface to facilitate attaching of the sample molecule and fragments, such as corona treatment, reacting with a silane coupling agent, or depositing avidin from solution and fixing the avidin by drying. Other standard surface modifications are available in the literature.

One method of operating the folded substrate illustrated in FIGS. 28-30 proceeds as follows: (1) Fabricate the folded substrate by depositing thin film layers on a silicon mold, wherein the mold is patterned with a predetermined number of adjoining, parallel vee-grooves of predetermined width and depth. Press the exposed surface of the folded substrate onto a stretched silicone rubber elastic substrate. Etch away the mold with XeF2, leaving the partially compressed accordion folded substrate temporarily attach to the stretched elastic substrate. (2) Compress the accordion folded substrate by relaxing the elastic substrate. If addition compression is desired, repeatedly transfer the accordion folded substrate to additional stretched elastic substrates and allow the elastic substrates to relax before transferring again. This is the elastic substrate method described above but run in reverse. The transfer process can be the same as any described for the elastic substrate method. For example, the folded substrate is coated with an aqueous solution of partially hydrolyzed PVOH or other film forming material, the water is evaporated, the folded substrate is peeled from the relaxed elastic substrate and pressed onto a stretched elastic substrate, and the PVOH is dissolved away with water. The compressed folded substrate is left on the final elastic substrate, and the top surface is away from the elastic substrate. (3) A sample molecule is extended by any means over the top surface of the folded substrate in a direction perpendicular to the axis of the folds, and attached to the top surface at or near convex folds. (4) The compressed folded substrate is opened, wherein the sample molecule is broken into fragments which are attached to the top surface at or near the convex folds. Expanding and opening of the compressed folded substrate can be accomplished by any suitable means, including the standard elastic substrate method described above. (5) The fragments can then be processed or analyzed by any suitable means. Where the fragments are nucleic acids, they may be sequenced, either on the folded substrate or in other vessels after being removed from the folded substrate.

Alternative accordion folded substrate materials, assemblies, and methods follow directly from the alternates and variations detailed elsewhere in this document for the nano-patterned substrate method and the elastic substrate method. For example, the compressed folded substrate can be opened using the methods present for a nano-patterned substrate. These include mounting the compressed fold substrate on a wax covered rigid support, and melting the wax and allowing it to flow whereby the folds are opened. In addition, the various methods can be applied sequentially or simultaneously. For example, a sample molecule may be initially processed using the elastic substrate method to generate fragments and provide an initial amount of spatial separation, and the fragments then transferred to an accordion folded substrate for further spatial separation.

CONCLUSIONS, RAMIFICATIONS, AND SCOPE

The embodiments, alternates, and variations presented are illustrations of beneficial embodiments. Although the descriptions are specific, these should not be construed as limiting the scope of the embodiments. Based on the descriptions provided herein, many other embodiments will be apparent to skilled practitioners of the techniques of molecular biology, biotechnology, DNA sequencing, semiconductor processing, thin-film processing, and MEMs technology. Thus the scope of the embodiments should be determined by the claims appended to the patent application and their legal equivalents, rather than by the examples given.

I claim:

1. A method for increasing the spatial separation in a first direction between members of a plurality of elements attached to a first substrate, said elements having an initial ordering along said first direction and said initial ordering maintained comprising,
    (a) providing said first substrate, said first substrate including at least one first surfaces, said first surfaces including a plurality of non-intersecting first regions, said first regions having a first ordering along said first direction, and said first substrate including a first means for increasing shortest distances between all pairs of said first regions and maintaining said first ordering along said first direction when acted upon by a first urging,
    (b) providing said elements, said elements attached to said first regions with at most one of said elements attached to each member of said first regions, said elements having initial spatial separations along said first direction between adjacent members of said elements of less than approximately 50 microns, said elements containing materials selected from the group consisting of nucleic acid, protein, DNA, double stranded DNA (dsDNA), single stranded DNA (ssDNA), RNA, double stranded RNA (dsRNA), single stranded RNA (ssRNA), DNA/RNA heteroduplexes, mRNA, cDNA, snRNA, siRNA, miRNA, nucleic acid oligomers, labeled-probe-assemblies, nucleic acids with at least one dye-labeled nucleotide, nucleic acid oligomers with at least one dye-labeled nucleotide, nucleic acids with at least one modified nucleotide, nucleic acid oligomers with at least one modified nucleotide, fragments of at least one nucleic acid molecule, islands of amplified nucleic acids, fragments of proteins, denatured proteins, fragments of denatured proteins, protein complexes, and fragments of protein complexes and
    (c) applying said first urging to said first means, whereby said elements have increased spatial separations and said initial ordering along said first direction.

2. The method of claim 1 further including,
    (d) providing a second substrate, said second substrate including at least one second surfaces, said second surfaces including a plurality of non-intersecting second regions, said second regions having a second ordering along a second direction, and said second substrate including a second means for increasing shortest distances between all pairs of said second regions and maintaining said second ordering along said second direction when acted upon by a second urging,
    (e) transferring said elements from said first regions to said second regions and attaching said elements to said second regions, wherein at most one of said elements is attached to each of said second regions and said elements have said initial ordering along said second direction, and
    (f) applying said second urging to said second means, whereby said elements have further increased spatial separations and said initial ordering along said second direction.

3. The method of claim 2 further including, repeating the method of claim 2 for a predetermined number of cycles, said cycles ordered consecutively from cycle number (l) to cycle number (n), and wherein cycle number (m) is an arbitrary member of said cycles, and wherein said second substrate, said second surfaces, said second regions, said second ordering, said second direction, said second means, and said second urging of cycle number (m) are redefined in cycle number (m+1) as said first substrate, said first surfaces, said first regions, said first ordering, said first direction, said first means, and said first urging, respectively, and a new member of said second substrate is provided in step (d) of each member of said cycles.

4. The method of claim 2 wherein transferring said elements from said first regions to said second regions comprises,
  (a) providing a film forming solution composed of at least one first solvent and at least one film forming solute, said solute dissolved and/or suspended in said solvent,
  (b) covering said elements with a contiguous volume of said solution,
  (c) forming a transfer substrate by evaporating said solvent or freezing said solution, wherein said elements are attached to said transfer substrate and have said initial ordering along said first direction,
  (d) removing said elements from said first regions, wherein said elements remain attached to said transfer substrate,
  (e) contacting and attaching said elements to said second regions, and releasing said elements from said transfer substrate by either, providing a second solvent and dissolving said transfer substrate in said second solvent, or melting said transfer substrate, wherein said elements have said initial ordering in said second direction.

5. The method of claim 2 wherein transferring said elements from said first regions to said second regions comprises,
  (a) providing a transfer substrate, said transfer substrate includes a first layer having at least one third surface and said first layer is composed of either, a soluble solid, said soluble solid being soluble in a solvent, a frozen liquid, or a volatile solid compound with sublimation rate measuring greater than 1 micron per 24 hours at temperatures below 300° C.,
  (b) contacting said third surface to said elements such that said elements are attached to said third surface and have said initial ordering along said first direction,
  (c) removing said elements from said first regions, wherein said elements remain attached to said third surface,
  (d) contacting and attaching said elements to said second regions wherein said elements have said initial ordering along said second direction and,
  (e) releasing said elements from said third surface by either, providing said solvent and dissolving said first layer in said solvent, melting said first layer, or sublimating said first layer.

6. The method of claim 5 further including moistening said third surface prior to step (b) with a liquid selected from the group consisting of an aqueous solution, water, buffered water, isopropyl alcohol, ethyl alcohol, said third solvent, polar solvents, non-polar solvents.

7. The method of claim 2 wherein transferring said elements from said first regions to said second regions comprises,
  (a) providing a film forming compound composed of materials selected from cyclododecane, camphor, solid compounds with sublimation rates measuring greater than 1 micron per 24 hours at temperatures below 300° C., and mixtures of these,
  (b) forming a transfer substrate, said transfer substrate including at least one layer of said compound and said layer covering and attached to said elements, by either, melting said compound and spreading a melt of said compound over said elements and freezing said melt, or condensing to solid a vapor of said compound over said elements, wherein said elements have said initial ordering along said first direction,
  (c) removing said elements from said first regions, wherein said elements remain attached to said transfer substrate,
  (d) contacting and attaching said elements to said second regions, and releasing said elements from said transfer substrate by sublimating said layer, wherein said elements have said initial ordering in said second direction.

8. The method of claim 1 further including providing a readout and recording device, processing said elements wherein signals are generated that are correlated with at least one physical property of said elements, and using said readout and recording device to monitor and record said signals.

9. The method of claim 1 wherein multiple independent groups of said elements are processed substantially simultaneously on said substrate.

10. The method of claim 1 further including providing a sample molecule, extending said sample molecule over said first regions approximately along said first direction, attaching said sample molecule to said first regions at multiple locations along said sample molecule, dividing said sample molecule into multiple fragments, wherein said fragments are attached to said first regions with at most one of said fragments attached to each member of said first regions, and said elements comprise said fragments.

11. The method of claim 1 wherein said first substrate is frabricated with stretchable materials selected from the group consisting of elastomeric compounds, plastically deformable compounds, thermoplastic compounds, gels, silicone rubber, fluorosilicone rubber, polyurethane rubber, Sorbothane, EPDM rubber, neoprene rubber, latex, natural rubber, nitrile rubber, butyl rubber, thermoplastic elastomers, sylgard 186, sylgard 184, silicone gel, hydrophobic gels and putties, silicone putty, silicone dilatent compound, blow moldable plastics, low glass transition temperature polymers, mixtures of ethylene-vinyl acetate and ethylene acetate plasticizer and acetone, parafilm M, teflon skived film, polyethylene film, polypropylene film, duco cement, modified nitrocellulose solutions, and mixtures of these.

12. The method of claim 1 wherein at least a portion of said first substrate resembles an approximately planar assembly folded into an accordion folded or pleated structure, and said portion of said substrate has said first surface and a bottom surface and said first surfaces and said bottom surface are approximately parallel and separated by less than one micron and said portion has said accordion folded structure with a plurality of folds wherein each of said folds is aligned approximately parallel to other members of said folds and said folds are aligned approximately perpendicular to said first direction, and wherein said first surface covers convex members of said folds and concave members of said folds and said first regions include the areas of said first surface proximate to said convex members of said folds, and wherein the distances measured along said first direction between said convex members of said folds are increased by applying of said first urging.

13. A method for increasing the spatial separation along a first direction between members of a plurality of elements attached to a first substrate, said elements having an initial ordering along said first direction and said initial ordering maintained comprising,
- (a) providing said first substrate, said first substrate including two first end regions, and said first end regions separated from each other along said first direction,
- (b) providing said elements, said elements attached to said first substrate between said first end regions, said elements having initial spatial separations along said first direction between adjacent members of said elements less than approximately 50 microns, said elements containing materials selected from the group consisting of nucleic acid, protein, DNA, double stranded DNA (dsDNA), single stranded DNA (ssDNA), RNA, double stranded RNA (dsRNA), single stranded RNA (ssRNA), DNA/RNA heteroduplexes, mRNA, cDNA, snRNA, siRNA, miRNA, nucleic acid oligomers, labeled-probe-assemblies, nucleic acids with at least one dye-labeled nucleotide, nucleic acid oligomers with at least one dye-labeled nucleotide, nucleic acids with at least one modified nucleotide, nucleic acid oligomers with at least one modified nucleotide, fragments of at least one nucleic acid molecule, islands of amplified nucleic acids, fragments of proteins, denatured proteins, fragments of denatured proteins, protein complexes, and fragments of protein complexes and
- (c) providing a first means for stretching said first substrate between said first end regions along said first direction,
- (d) applying said first means to said first substrate,
whereby said elements have increased spatial separations along said first direction and said initial ordering along said first direction.

14. The method of claim 13 further including,
- (e) providing a second substrate, said second substrate including two second end regions, and said second end regions separated from each other along a second direction,
- (f) providing a second means for stretching said second substrate between said second end regions along said second direction,
- (g) providing a transfer means for transferring said elements from said first substrate to said second substrate between said second end regions and maintaining said initial ordering along said second direction,
- (h) applying said transfer means to said elements, and
- (i) applying said second means to said second substrate,
whereby said elements have further increased spatial separations and said initial ordering along said second direction.

15. The method of claim 14 further including, repeating the method of claim 14 for a predetermined number of cycles, said cycles ordered consecutively from cycle number (1) to cycle number (n), and wherein cycle number (m) is an arbitrary member of said cycles, and wherein said second substrate, said second end regions, said second direction, and said second means of cycle number (m) are redefined in cycle number (m+1) as said first substrate, said first end regions, said first direction, and said first means, respectively, and a new member of said second substrate is provided in step (e) of each member of said cycles.

16. The method of claim 14 wherein said transfer means comprises,
- (a) providing a film forming solution composed of at least one first solvent and at least one film forming solute, said solute dissolved and/or suspended in said first solvent,
- (b) covering said elements with a contiguous volume of said solution,
- (c) forming a transfer substrate by evaporating said first solvent or freezing said solution, wherein said elements are attached to said transfer substrate and have said initial ordering along said first direction,
- (d) removing said elements from said first substrate, wherein said elements remain attached to said transfer substrate,
- (e) contacting and attaching said elements to said second substrate between said second end regions and having said initial ordering along said second direction, and releasing said elements from said transfer substrate by either, providing a second solvent and dissolving said transfer substrate in said second solvent, or melting said transfer substrate, wherein said elements have said initial ordering in said second direction.

17. The method of claim 11 wherein said transfer means comprises,
- (a) providing a transfer substrate, said transfer substrate including a first layer having at least one surface which first layer is composed of either, a soluble solid, said soluble solid being soluble in a solvent, a frozen liquid, or a volatile solid compound with sublimation rate measuring greater than 1 micron per 24 hours at temperatures below 300° C.,
- (b) contacting said surface to said elements such that said elements are attached to said surface and have said initial ordering along said first direction,
- (c) removing said elements from said first substrate, wherein said elements remain attached to said surface,
- (d) contacting and attaching said elements to said second substrate between said second end regions wherein said elements have said initial ordering along said second direction, and
- (e) releasing said elements from said surface by providing said solvent and dissolving said first layer in said solvent, melting said first layer, or sublimating said first layer.

18. The method of claim 13 wherein said first substrate is fabricated with stretchable materials including elastic materials, elastomeric compounds, plastically deformable compounds, thermoplastic compounds, gels, silicone rubber, fluorosilicone rubber, polyurethane rubber, Sorbothane, EPDM rubber, neoprene rubber, latex, natural rubber, nitrile rubber, butyl rubber, thermoplastic elastomers, Sylgard 186, Sylgard 184, silicone gel, hydrophobic gels and putties, silicone putty, silicone dilatent compound, low-temperature blow moldable plastics, low glass transition temperature polymers, mixtures of ethylene-vinyl acetate and ethylene acetate plasticizer and acetone, Parafilm M, Teflon skived film, polyethylene film, polypropylene film, Duco Cement, modified nitrocellulose solutions, and mixtures of these.

19. The method of claim 13 further including providing a readout and recording device, processing said elements wherein signals are generated that are correlated with at least one physical property of said elements, and using said readout and recording device to monitor and record said signals.

20. The method of claim 13 wherein multiple independent groups of said elements are processed substantially simultaneously on said first substrate.

21. The method of claim 13 further including providing a sample molecule, extending said sample molecule over said first substrate between said first end regions approximately along said first direction, attaching said sample molecule to said first substrate at multiple locations along said sample molecule, dividing said sample molecule into multiple fragments, and said elements comprise said fragments.

22. A method for increasing the spatial separation along a first direction between members of a plurality of elements attached to a first substrate, said elements having an initial ordering along said first direction and said initial ordering maintained comprising,
(a) providing said first substrate, said first substrate including two first end regions, and said first end regions separated from each other along said first direction,
(b) providing said elements, said elements attached to said first substrate between said first end regions,
(c) providing a first means for stretching said first substrate between said first end regions along said first direction,
(d) applying said first means to said first substrate,
(e) providing a second substrate, said second substrate including two second end regions, and said second end regions separated from each other along a second direction,
(f) providing a second means for stretching said second substrate between said second end regions along said second direction,
(g) providing a film forming solution composed of at least one first solvent and at least one film forming solute, said solute dissolved and/or suspended in said first solvent,
(h) covering said elements with a contiguous volume of said solution,
(i) forming a transfer substrate by evaporating said first solvent or freezing said solution, wherein said elements are attached to said transfer substrate and have said initial ordering along said first direction,
(j) removing said elements from said first substrate, wherein said elements remain attached to said transfer substrate,
(k) contacting and attaching said elements to said second substrate between said second end regions and said elements having said initial ordering along said second direction,
(l) releasing said elements from said transfer substrate by either, providing a second solvent and dissolving said transfer substrate in said second solvent, or melting said transfer substrate,
(m) applying said second means to said second substrate, whereby said elements have increased spatial separations and said initial ordering along said second direction, said elements containing materials selected from the group consisting of nucleic acid, protein, DNA, double stranded DNA (dsDNA), single stranded DNA (ssDNA), RNA, double stranded RNA (dsRNA), single stranded RNA (ssRNA), DNA/RNA heteroduplexes, mRNA, cDNA, snRNA, siRNA, miRNA, nucleic acid oligomers, labeled-probe-assemblies, nucleic acids with at least one dye-labeled nucleotide, nucleic acid oligomers with at least one dye-labeled nucleotide, nucleic acids with at least one modified nucleotide, nucleic acid oligomers with at least one modified nucleotide, fragments of at least one nucleic acid molecule, islands of amplified nucleic acids, fragments of proteins, denatured proteins, fragments of denatured proteins, protein complexes, and fragments of protein complexes.

23. The method of claim 22 further including, repeating the method of claim 22 for a predetermined number of cycles, said cycles ordered consecutively from cycle number (l) to cycle number (n), and wherein cycle number (m) is an arbitrary member of said cycles, and wherein said second substrate, said second end regions, said second direction, and said second means of cycle number (m) are redefined in cycle number (m+1) as said first substrate, said first end regions, said first direction, and said first means, respectively, and a new member of said second substrate is provided in step (e) of each member of said cycles.

24. The method of claim 22 wherein said first substrate is frabricated with stretchable materials selected from the group consisting of elastomeric compounds, plastically deformable compounds, thermoplastic compounds, gels, silicone rubber, fluorosilicone rubber, polyurethane rubber, sorbothane, EPDM rubber, neoprene rubber, latex, natural rubber, nitrile rubber, butyl rubber, thermoplastic elastomers, sylgard 186, sylgard 184, silicone gel, hydrophobic gels and putties, silicone putty, silicone dilatent compound, blow moldable plastics, low glass transition temperature polymers, mixtures of ethylene-vinyl acetate and ethylene acetate plasticizer and acetone, parafilm M, teflon skived film, polyethylene film, polypropylene film, duco cement, modified nitrocellulose solutions, and mixtures of these.

25. The method of claim 22 further including providing a readout and recording device, processing said elements wherein signals are generated that are correlated with at least one physical property of said elements, and using said readout and recording device to monitor and record said signals.

26. The method of claim 22 wherein multiple independent groups of said elements are processed substantially simultaneously on said first substrate.

27. The method of claim 22 further including providing a sample molecule, extending said sample molecule over said first substrate between said first end regions approximately along said first direction, attaching said sample molecule to said first substrate at multiple locations along said sample molecule, dividing said sample molecule into multiple fragments, and said elements comprise said fragments.

28. The method of claim 22 wherein said first substrate and said second substrate are fabricated of different materials.

* * * * *